US012618059B2

(12) United States Patent
Eliyahu et al.

(10) Patent No.: US 12,618,059 B2
(45) Date of Patent: May 5, 2026

(54) Anc80 ENCODING SPHINGOLIPID-METABOLIZING PROTEINS

(71) Applicant: ICAHN SCHOOL OF MEDICINE AT MOUNT SINAI, New York, NY (US)

(72) Inventors: Efrat Eliyahu, New York, NY (US); Adam Vincek, New York, NY (US); Michael Katz, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 1226 days.

(21) Appl. No.: 17/256,812

(22) PCT Filed: Mar. 7, 2019

(86) PCT No.: PCT/US2019/021201
§ 371 (c)(1),
(2) Date: Dec. 29, 2020

(87) PCT Pub. No.: WO2020/005341
PCT Pub. Date: Jan. 2, 2020

(65) Prior Publication Data
US 2021/0244827 A1 Aug. 12, 2021

Related U.S. Application Data

(60) Provisional application No. 62/692,185, filed on Jun. 29, 2018.

(51) Int. Cl.
| | |
|---|---|
| *C12N 15/864* | (2006.01) |
| *A61K 35/76* | (2015.01) |
| *A61K 48/00* | (2006.01) |
| *A61P 9/00* | (2006.01) |
| *C12N 9/80* | (2006.01) |
| *C12N 15/52* | (2006.01) |
| *C12N 15/86* | (2006.01) |

(52) U.S. Cl.
CPC .............. *C12N 9/80* (2013.01); *A61K 48/005* (2013.01); *C12N 15/52* (2013.01); *C12N 15/86* (2013.01); *C12N 2750/14143* (2013.01); *C12Y 305/01023* (2013.01)

(58) Field of Classification Search
None
See application file for complete search history.

(56) References Cited

U.S. PATENT DOCUMENTS

| | | | |
|---|---|---|---|
| 8,697,359 B1 | 4/2014 | Zhang | |
| 8,961,962 B2 | 2/2015 | Schuchman et al. | |
| 9,695,220 B2 | 7/2017 | Vandenberghe et al. | |
| 2002/0099029 A1 | 7/2002 | Liau et al. | |
| 2007/0111306 A1* | 5/2007 | Salli ..................... | C12N 5/0606 |
| | | | 435/325 |
| 2008/0199450 A1 | 8/2008 | Schuchman et al. | |
| 2011/0104130 A1* | 5/2011 | Medin .................. | C12N 9/1229 |
| | | | 435/235.1 |
| 2012/0039812 A1 | 2/2012 | Holsboer et al. | |
| 2013/0259924 A1 | 10/2013 | Bancel et al. | |
| 2014/0287015 A1 | 9/2014 | Schuchman et al. | |
| 2016/0038574 A1 | 2/2016 | Schuchman | |
| 2017/0044516 A1 | 2/2017 | Tsai et al. | |
| 2017/0332610 A1 | 11/2017 | Voronina et al. | |
| 2017/0356060 A1 | 12/2017 | Murillo Sauca et al. | |
| 2018/0008679 A1 | 1/2018 | Niklason et al. | |
| 2018/0066252 A1 | 3/2018 | Patel et al. | |
| 2019/0117733 A1 | 4/2019 | Chien et al. | |
| 2019/0216730 A1 | 7/2019 | Heartlein et al. | |
| 2020/0399623 A1* | 12/2020 | Baik .................. | A61K 47/6849 |
| 2021/0155956 A1* | 5/2021 | Stedman ................ | C12N 15/86 |
| 2021/0322472 A1* | 10/2021 | Medin .................. | A61K 48/005 |

FOREIGN PATENT DOCUMENTS

| | | |
|---|---|---|
| JP | 2017-121244 A | 7/2017 |
| WO | WO 2005051891 * | 6/2005 |
| WO | 2008086296 A2 | 7/2008 |
| WO | 2013151663 A1 | 10/2013 |
| WO | 2013151666 A | 10/2013 |
| WO | 2013185069 A1 | 12/2013 |
| WO | 2014140051 A1 | 9/2014 |
| WO | 2017153936 A1 | 9/2017 |
| WO | 2019009979 A1 | 1/2019 |
| WO | 2019/150192 A1 | 8/2019 |
| WO | 2019173615 A1 | 9/2019 |
| WO | 2019173632 A1 | 9/2019 |

(Continued)

OTHER PUBLICATIONS

Carvahlo et al, Synthetic Adeno-Associated Viral Vector Efficiently Targets Mouse and Nonhuman Primate Retina In Vivo, Human Gene Therapy, 2018, pp. 771-784.*
Hudry et al, Efficient Gene Transfer to the Central Nervous System by Single-Stranded Anc80L65, Molecular Therapy: Methods & Clinical Development vol. 10 Sep. 2018, pp. 197-208.*
Katz et al, Efficient Cardiac Gene Transfer and Early Onset Expression of a Synthetic Adeno-Associated Viral Vector, Anc80L65 After Intramyocardial Administration, 2022, J Thorac Cardiovasc Surg. Dec. 2022 ; 164(6): p. 1-20.*
Martino and Markusic, Immune Response Mechanisms against AAV Vectors in Animal Models, Molecular Therapy: Methods & Clinical Development vol. 17 Jun. 2020, pp. 198-208.*

(Continued)

*Primary Examiner* — Maria Marvich
(74) *Attorney, Agent, or Firm* — Heslin Rothenberg Farley & Mesiti P.C.

(57) ABSTRACT

The present disclosure pertains to the use of an Anc80 viral vector that encodes a sphingolipid-metabolizing protein such as acid ceramidase to achieve expression of the sphingolipid-metabolizing protein in a mammalian cell or group of cells. Expression of the protein from the Anc80 vector reduces high levels of ceramide in the cell that lead to cell death or senescence.

5 Claims, 20 Drawing Sheets

Specification includes a Sequence Listing.

(56) References Cited

FOREIGN PATENT DOCUMENTS

| | | |
|---|---|---|
| WO | 2021050064 A1 | 3/2021 |
| WO | 2021050877 A1 | 3/2021 |

OTHER PUBLICATIONS

Farbus-Domingo, WO 2005051891 translation, pp. 1-11.*

Rutherford et al, Regulation of cell survival by sphingosine-1-phosphate receptor S1P1 via reciprocal ERK-dependent suppression of Bim and PI-3-kinase/protein kinase C-mediated upregulation of Mcl-1, Cell Death and Disease (2013) pp. 1-15.*

Ripa et al, Physiology, Cardiac Muscle, 2023, StatPearls, pp. 1-11.*

Shu et al, Emerging Roles of Ceramide in Cardiovascular Diseases, Aging and Disease, 2022, pp. 232-245.*

Chow et al. (Scientific Reports 6, article 24127, pp. 1-9, Apr. 12, 2016).

Bahr et al, "Peripheral Blood Mononuclear Cell Gene Expression in Chronic Obstructive Pulmonary Disease", American Journal of Respiratory Cell and Molecular Biology, vol. 49, No. 2, Aug. 1, 2013, pp. 316-323.

Schuchman, "Acid ceramidase and the treatment of ceramide diseases: The expanding role of enzyme replacement therapy", Biochimica et Biophysica Acta, Molecular Basis of Disease, vol. 1862, No. 9, May 4, 2016, p. 1459-1471.

Cannavo et al., "β1-Adrenergic Receptor and Sphingosine-1-Phosphate Receptor 1 (S1PR1) Reciprocal Downregulation Influences Cardiac Hypertrophic Response and Progression to Heart Failure: Protective Role of S1PR1 Cardiac Gene Therapy" Circulation, 2013, 128(15):1612-1622.

Talati et al., "Fatty acid metabolism in pulmonary arterial hypertension: role in right ventricular dysfunction and hypertrophy," Pulmonary Circulation, 2015, 5(2):269-278.

Petrache, "Ceramide upregulation causes pulmonary cell apoptosis and emphysema-like disease in mice," Nature Medicine, 2005, 11(5): 491-498.

Blaho et al., "An Update on the Biology of Sphingosine 1-Phosphate Receptors," Journal of Lipid Research 55:1596-1608 (2014).

Cannavo et al., "Sphingosine Kinases and Sphingosine 1-Phosphate Receptors: Signaling and Actions in the Cardiovascular System," Frontiers in Pharmacology 8(556):1-12 (2017).

Eliyahu et al., "Acid Ceramidase Improves the Quality of Oocytes and Embryos and the Outcome of In Vitro Fertilization," The FASEB Journal 24:1229-1238 (2010).

Ferizi et al., "Human Cellular CYBA UTR Sequences Increase mRNA Translation Without Affecting the Half-Life of Recombinant RNA Transcripts," Scientific Reports 6(39149):1-13 (2016).

Glogar, D.H., "Definition and Significance of the Area at Risk in Myocardial Infarct and the Ischemic Border Zone in Acute Myocardial Infarct," Acta Med Austriaca Suppl. 36:1-40 (1986) (abstract only).

Landegger et al., "A Synthetic AAV Vector Enables Safe and Efficient Gene Transfer to the Mammalian Inner Ear," Nat. Biotechnol. 35(3):280-284 (2017).

Maceyka et al., "Sphingosine-1-Phosphate Signaling And Its Role In Disease," Trends Cell Biol. 22(1):50-60 (2012).

Pan et al., "Gene Therapy Restores Auditory and Vestibular Function in a Mouse Model of Usher Syndrome Type 1c," Nat. Biotechnol. 35(3):264-272 (2017).

Ramsubir, "Retrovirus-Mediated Gene Therapy For Farber Disease," Doctoral Thesis, Graduate Department of Medical Biophysics, University of Toronto (2008).

Sugano et al., "Overexpression of Acid Ceramidase (ASAH1) Protects Retinal Cells (ARPE19) From Oxidative Stress," Journal of Lipid Research 60:30-43 (2019).

Suzuki et al., "Cochlear Gene Therapy With Ancestral AAV in Adult Mice: Complete Transduction of Inner Hair Cells Without Cochlear Dysfunction," Scientific Reports 7(45524):1-11 (2017).

Youn et al., "Modified mRNA as an Alternative to Plasmid DNA (pDNA) for Transcript Replacement and Vaccination Therapy," Expert Opin. Biol. Ther. 15(9):1337-1348 (2015).

Zinn et al., "In Silico Reconstruction of the Viral Evolutionary Lineage Yields a Potent Gene Therapy Vector," Cell Reports 12:1056-1068 (2015).

Chen et al., "The Sphingosine Kinase 1/Sphingosine-1-Phosphate Pathway in Pulmonary Arterial Hypertension," American Journal of Respiratory and Critical Care Medicine 190(9):1032-1043 (2014).

Gairhe et al., "Sphingosine-1-Phosphate is Involved in the Occlusive Arteriopathy of Pulmonary Arterial Hypertension," Pulmonary Circulation 6(3):369-380 (2016).

Pyne et al., "Sphingosine Kinase 1: A Potential Therapeutic Target in Pulmonary Arterial Hypertension?," Trends Mol. Med. 23:786-798 (2017).

Magadum et al., "mRNA-Based Protein Replacement Therapy for the Heart," Molecular Therapy 27(4):785-93 (2019).

Kaur et al., "Modified mRNA as a Therapeutic Tool for the Heart," Cardiovascular Drugs and Therapy 34:871-880 (2020).

D'Alto et al., "Pulmonary Arterial Hypertension Associated With Congenital Heart Disease," Eur. Respir. Rev. 21:328-337 (2012).

Zangi et al., "Modified mRNA Directs the Fate of Heart Progenitor Cells and Induces Vascular Regeneration After Myocardial Infarction," Nature Biotechnology 31:898 (2013).

Reforgiato et al., "Inhibition of Ceramide de Novo Synthesis as a Postischemic Strategy to Reduce Myocardial Reperfusion Injury," Basic Res. Cardiol. 111:12 (2016).

Gardlik et al., "Vectors and delivery systems in gene therapy," Medical Science Monitor, 2005, 11(4):RA110-121.

Koch et al., "Molecular Cloning and Characterization of a Full-length Complementary DNA Encoding Human Acid Ceramidase," The Journal of Biological Chemistry, 1996, 27(51):33110-33115.

Song et al., "Activation of PI3Ky/Akt pathway increases cardiomyocyte HMGB1 expression in diabetic environment," Oncotarget, 2016, 7(49):80803-80810.

Sadowski et al., "The sequence-structure relationship and protein function prediction," Current Opinion in Structural Biology, 2009, 19:357-362.

Tang et al., "Identification of Dehalobacter reductive dehalogenases that catalyse dechlorination of chloroform 1,1,1-trichloroethane and 1,1-dichloroethane," Philosophical Transactions of the Royal Society B, 2013, 368 (1616):20120318.

Houdebine, "The methods to generate transgenic animals and to control transgene expression," Journal of Biotechnology, 2002, 98:145-160.

Witkowski et al., "Conversion of a β-Ketoacyl Synthase to a Malonyl Decarboxylase by Replacement of the Active-Site Cysteine with Glutamine," Biochemistry, 1999, 38(36):11643-11650.

Seffernick et al., "Melamine Deaminase and Atrazine Chloroydrolase: 98 Percent Identical but Functionally Different," Journal of Bacteriology, 2001, 183(8):2405-2410.

Mullins et al., "Transgenesis in Nonmurine Species," Hypertension, 1993, 22(4):630-633.

Wang et al., "Delivery of CRISPR/CAS9 by Novel Strategies for Gene Therapy," Chembiochem, 2019, 20(5):634-643.

Phillips, "The challenge of gene therapy and DNA delivery," The Journal of Pharmacy and Pharmacology, 2001, 53(9):1169-1174.

Branden et al., "Prediction, Engineering, and Design of Protein Structures," Garland Publishing Inc., New York, 1991, cover page, inside page and p. 1).

Scharf et al., "Hemodynamic Characterization of Patients with Severe Emphysema," American Journal of Respiratory and Critical Care Medicine, 2002, 166(3):314-322.

Wright et al., "Pulmonary hypertension in chronic obstructive pulmonary disease: current theories of pathogenesis and their implications for treatment," Thorax, 2005, 60(7):605-609.

Biernacki et al., "Pulmonary Hemodynamics, Gas Exchange, and the Severity of Emphysema as Assessed by Quantitative CT Scan in Chronic Bronchitis and Emphysema," American Review of Respiratory Disease, 1988, 139(6):1509-1515.

* cited by examiner

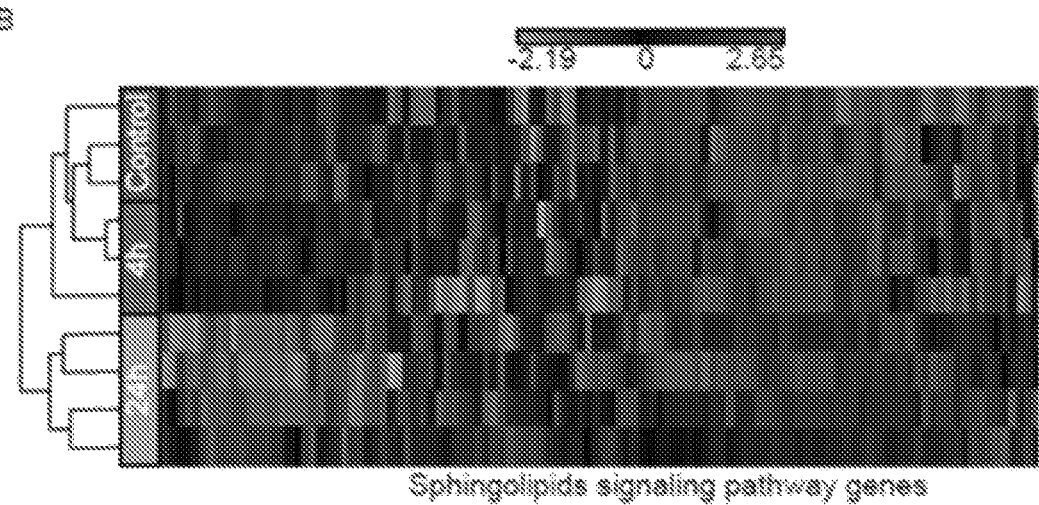
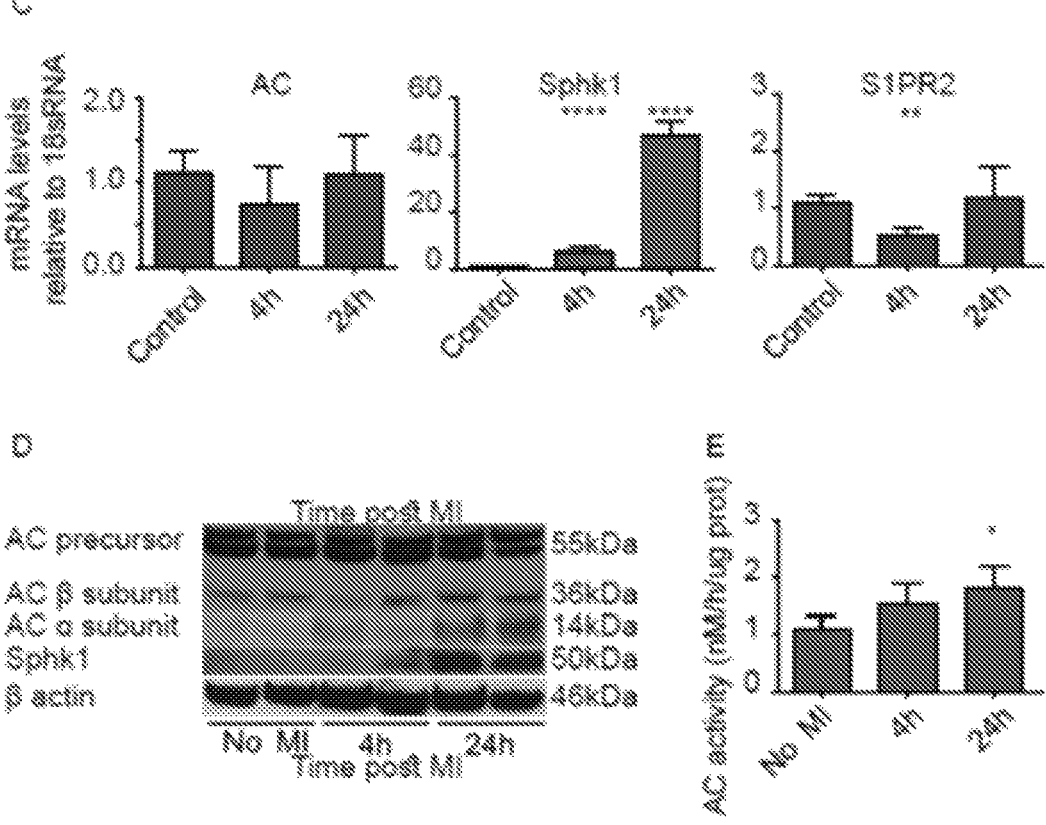
Figures 1B-1E

A

1day post IM injection 3 days post IM injection 6 weeks post IM injection

1ˢᵗ reaction with anti AC H-41 antibody left inverted terminal repeat 1~103
encapsidation signal (ES) 183~331
CMV promoter 341~933
multiple cloning site 940~987
SV40 polyA 1011~1238
Ad5 right arm homology 1243~3497
Ad5 left arm homology 3545~4428
right inverted terminal repeat 4429~4531
pBR322 origin 4736~5402
kanamycin resistance ORF 6211~7002 pShuttle-CMV Multiple Cloning Site Region
(sequence shown 888~1031)

SEQUENCE LISTING

<160> NUMBER OF SEQ ID NOS: 34

<210> SEQ ID NO 1
<211> LENGTH: 1188
<212> TYPE: DNA
<213> ORGANISM: Artificial Sequence
<220> FEATURE:
<223> OTHER INFORMATION: synthetic vector

<400> SEQUENCE: 1

```
atgccgggcc ggagttgcgt cgccttagtc ctcctggctg ccgccgtcag ctgtgccgtc        60
gcgcagcacg cgccgccgtg gacagaggac tgcagaaaat caacctatcc tccttcagga       120
ccaacgtaca gaggtgcagt tccatggtac accataaatc ttgacttacc accctacaaa       180
agatggcatg aattgatgct tgacaaggca ccagtgctaa aggttatagt gaattctctg       240
aagaatatga taaatacatt cgtgccaagt ggaaaaatta tgcaggtggt ggatgaaaaa       300
ttgcctggcc tacttggcaa cttttcctggc cctttgaag aggaaatgaa gggtattgcc       360
gctgttactg atataccttt aggagagatt atttcattca atattttta tgaattattt        420 accatttgta cttcaatagt agcagaagac aaaaaaggtc atctaataca tgggagaaac       480
atggattttg gagtatttct tgggtggaac ataataatg atacctgggt cataactgag        540
caactaaaac cttttaacagt gaatttggat ttccaaagaa acaacaaaac tgtcttcaag      600
gcttcaagct ttgctggcta tgtgggcatg ttaacaggat tcaaaccagg actgttcagt       660
cttacactga atgaacgttt cagtataaat ggtggttatc tgggtattct agaatggatt       720
ctgggaaaga aagatgtcat gtggataggg ttcctcacta gaacagttct ggaaaatagc       780
acaagttatg aagaagccaa gaatttattg accaagacca agatattggc cccagcctac       840
tttatcctgg gaggcaacca gtctggggaa ggttgtgtga ttacacgaga cagaaaggaa       900
tcattggatg tatatgaact cgatgctaag cagggtagat ggtatgtggt acaaacaaat       960
tatgaccgtt ggaaacatcc cttcttcctt gatgatcgca gaacgcctgc aaagatgtgt      1020
ctgaaccgca ccagccaaga gaatatctca tttgaaacca tgtatgatgt cctgtcaaca      1080
aaacctgtcc tcaacaagct gaccgtatac acaaccttga tagatgttac caaaggtcaa      1140
ttcgaaactt acctgcggga ctgccctgac ccttgtatag gttggtga                   1188
```

<210> SEQ ID NO 2
<211> LENGTH: 1197
<212> TYPE: DNA
<213> ORGANISM: Artificial Sequence
<220> FEATURE:
<223> OTHER INFORMATION: synthetic oligomer

<400> SEQUENCE: 2

```
atggatccag tggtcggttg cggacgtggc ctctttggtt ttgtttctc agcgggcggc         60 ccccggggcg tgctcccgcg gccctgccgc gtgctggtgc tgctgaaccc gcgcggcggc       120
aagggcaagg ccttgcagct cttccggagt cacgtgcagc cccttttggc tgaggctgaa       180
atctccttca cgctgatgct cactgagcgg cggaaccacg cgcgggagct ggtgcggtcg       240
gaggagctgg gccgctggga cgctctggtg gtcatgtctg agacgggct gatgcacgag        300 gtggtgaacg ggctcatgga gcggcctgac tgggagaccg ccatccagaa gcccctgtgt       360
agcctcccag caggctctgg caacgcgctg gcagcttcct tgaaccatta tgctggctat       420
gagcaggtca ccaatgaaga cctcctgacc aactgcacgc tattgctgtg ccgccggctg       480
ctgtcaccca tgaacctgct gtctctgcac acggcttcgg ggctgcgcct cttctctgtg       540
ctcagcctgg cctggggctt cattgctgat gtggacctag agagtgagaa gtatcggcgt       600
ctgggggaga tgcgcttcac tctgggcacc ttcctgcgtc tggcagccct cgcgcacctac     660 cgcggccgac tggcctacct ccctgtagga agagtgggtt ccaagacacc tgcctccccc      720
gttgtggtcc agcagggccc ggtagatgca caccttgtgc cactggagga gccagtgccc       780
tctcactgga cagtggtgcc cgacgaggac tttgtgctag tcctggcact gctgcactcg       840
cacctgggca gtgagatgtt tgctgcaccc atgggccgct gtgcagctgg cgtcatgcat       900
```

-continued

```
ctgttctacg tgcgggcggg agtgtctcgt gccatgctgc tgcgcctctt cctggccatg     960
gagaagggca ggcatatgga gtatgaatgc ccctacttgg tatatgtgcc cgtggtcgcc    1020
ttccgcttgg agcccaagga tgggaaaggt gtgtttgcag tggatgggga attgatggtt    1080
agcgaggccg tgcagggcca ggtgcaccca aactacttct ggatggtcag cggttgcgtg    1140
gagcccccgc ccagctggaa gccccagcag atgccaccgc cagaagagcc cttatga       1197
```

<210> SEQ ID NO 3
<211> LENGTH: 1062
<212> TYPE: DNA
<213> ORGANISM: Artificial Sequence
<220> FEATURE:
<223> OTHER INFORMATION: synthetic oligomer

<400> SEQUENCE: 3

```
atgggcagct tgtactcgga gtacctgaac cccaacaagg tccaggaaca ctataattat      60
accaaggaga cgctggaaac gcaggagacg acctcccgcc aggtggcctc ggccttcatc     120
gtcatcctct gttgcgccat tgtggtggaa aaccttctgg tgctcattgc ggtggcccga     180
aacagcaagt tccactcggc aatgtacctg tttctgggca acctggccgc ctccgatcta     240
ctggcaggcg tggccttcgt agccaatacc ttgctctctg gctctgtcac gctgaggctg     300
acgcctgtgc agtggtttgc ccgggagggc tctgccttca tcacgctctc ggcctctgtc     360
ttcagcctcc tggccatcgc cattgagcgc acgtggccca ttgccaaggt caagctgtat     420
ggcagcgaca gagctgccg catgcttctg ctcatcgggg cctcgtggct catctcgctg      480
gtcctcggtg gcctgcccat ccttggctgg aactgcctgg ccacctcga ggcctgctcc      540 actgtcctgc ctctctacgc caagcattat gtgctgtgcg tggtgaccat cttctccatc     600
atcctgttgg ccatcgtggc cctgtacgtg cgcatctact gcgtggtccg ctcaagccac     660
gctgacatgg ccgccccgca gacgctagcc ctgctcaaga cggtcaccat cgtgctaggc     720
gtctttatcg tctgctggct gcccgccttc agcatcctcc ttctggacta tgcctgtccc     780
gtccactcct gcccgatcct ctacaaagcc cactactttt cgccgtctc caccctgaat      840 tccctgctca accccgtcat ctacacgtgg cgcagccggg acctgcggcg ggaggtgctt     900
cggccgctgc agtgctggag gccggggggtg ggggtgcaag gacggaggcg gggcgggacc    960
ccgggccacc acctcctgcc actccgcagc tccagctccc tggagagggg catgcacatg    1020
cccacgtcac ccacgtttct ggagggcaac acggtggtca tg                       1062
```

<210> SEQ ID NO 4
<211> LENGTH: 1653
<212> TYPE: DNA
<213> ORGANISM: Artificial Sequence
<220> FEATURE:
<223> OTHER INFORMATION: synthetic oligomer

<400> SEQUENCE: 4

```
atggccgatg ctaagaacat taagaagggc cctgctccct tctaccctct ggaggatggc      60
accgctggcg agcagctgca caaggccatg aagaggtatg ccctggtgcc tggcaccatt     120
gccttcaccg atgcccacat tgaggtggac atcacctatg ccgagtactt cgagatgtct     180
gtgcgcctgg ccgaggccat gaagaggtac ggcctgaaca ccaaccaccg catcgtggtg     240
tgctctgaga actctctgca gttcttcatg ccagtgctgg gcgccctgtt catcggagtg     300
gccgtggccc ctgctaacga catttacaac gagcgcgagc tgctgaacag catgggcatt     360
```

```
tctcagccta ccgtggtgtt cgtgtctaag aagggcctgc agaagatcct gaacgtgcag    420
aagaagctgc ctatcatcca gaagatcatc atcatggact ctaagaccga ctaccagggc    480
ttccagagca tgtacacatt cgtgacatct catctgcctc ctggcttcaa cgagtacgac    540
ttcgtgccag agtctttcga cagggacaaa accattgccc tgatcatgaa cagctctggg    600
tctaccggcc tgcctaaggg cgtggccctg cctcatcgca ccgcctgtgt gcgcttctct    660
cacgcccgcg accctatttt cggcaaccag atcatccccg acaccgctat tctgagcgtg    720
gtgccattcc accacggctt cggcatgttc accaccctgg gctacctgat ttgcggcttt    780
cgggtggtgc tgatgtaccg cttcgaggag gagctgttcc tgcgcagcct gcaagactac    840
aaaattcagt ctgccctgct ggtgccaacc ctgttcagct tcttcgctaa gagcaccctg    900
atcgacaagt acgacctgtc taacctgcac gagattgcct ctggcggcgc cccactgtct    960
aaggaggtgg cgaagccgt ggccaagcgc tttcatctgc caggcatccg ccagggctac   1020
ggcctgaccg agacaaccag cgccattctg attaccccag agggcgacga caagcctggc   1080
gccgtgggca aggtggtgcc attcttcgag gccaaggtgg tggacctgga caccggcaag   1140
accctgggag tgaaccagcg cggcgagctg tgtgtgcgcg ccctatgat tatgtccggc   1200 tacgtgaata accctgaggc cacaaacgcc ctgatcgaca aggacggctg gctgcactct   1260
ggcgacattg cctactggga cgaggacgag cacttcttca tcgtggaccg cctgaagtct   1320
ctgatcaagt acaagggcta ccaggtggcc ccagccgagc tggagtctat cctgctgcag   1380
caccctaaca ttttcgacgc cggagtggcc ggcctgcccg acgacgatgc cggcgagctg   1440
cctgccgccg tcgtcgtgct ggaacacggc aagaccatga ccgagaagga gatcgtggac   1500
tatgtggcca gccaggtgac aaccgccaag aagctgcgcg cggagtggt gttcgtggac   1560 gaggtgccca agggcctgac cggcaagctg acgcccgca agatccgcga gatcctgatc   1620
aaggctaaga aaggcggcaa gatcgccgtg taa                                 1653

<210> SEQ ID NO 5
<211> LENGTH: 801
<212> TYPE: DNA
<213> ORGANISM: Artificial Sequence
<220> FEATURE:
<223> OTHER INFORMATION: synthetic oligomer

<400> SEQUENCE: 5
atggtgagca agggcgagga gctgttcacc ggggtggtgc ccatcctggt cgagctggac     60
ggcgacgtaa acggccacaa gttcagcgtg tccggcgagg cgagggcga tgccacctac    120 ggcaagctga ccctgaagtt catctgcacc accggcaagc tgcccgtgcc ctggcccacc    180
ctcgtgacca ccctgaccta cggcgtgcag tgcttcagcc gctacccga ccacatgaag    240 cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaaggga    720
gatccaaaaa agaagagaaa ggtaggcgat ccaaaaaaga gagaaaggt aggtgatcca    780
```

-continued

```
aaaaagaaga gaaaggtata a                                        801

<210> SEQ ID NO 6
<211> LENGTH: 1236
<212> TYPE: DNA
<213> ORGANISM: Artificial Sequence
<220> FEATURE:
<223> OTHER INFORMATION: synthetic oligomer

<400> SEQUENCE: 6
atgaactgct gcatcgggct gggagagaaa gctcgcgggt cccaccgggc ctcctaccca     60
agtctcagcg cgcttttcac cgaggcctca attctgggat ttggcagctt tgctgtgaaa    120
gcccaatgga cagaggactg cagaaaatca acctatcctc cttcaggacc aacgtacaga    180
ggtgcagttc catggtacac cataaatctt gacttaccac cctacaaaag atggcatgaa    240
ttgatgcttg acaaggcacc agtgctaaag gttatagtga attctctgaa gaatatgata    300
aatacattcg tgccaagtgg aaaaattatg caggtggtgg atgaaaaatt gcctggccta    360
cttggcaact ttcctggccc ttttgaagag gaaatgaagg gtattgccgc tgttactgat    420
atacctttag gagagattat ttcattcaat attttttatg aattatttac catttgtact    480
tcaatagtag cagaagacaa aaaaggtcat ctaatacatg ggagaaacat ggattttgga    540
gtatttcttg ggtggaacat aaataatgat acctgggtca taactgagca actaaaacct    600
ttaacagtga atttggattt ccaaagaaac aacaaaactg tcttcaaggc ttcaagcttt    660
gctggctatg tgggcatgtt aacaggattc aaaccaggac tgttcagtct tacactgaat    720
gaacgtttca gtataaatgg tggttatctg ggtattctag aatggattct gggaaagaaa    780
gatgtcatgt ggatagggtt cctcactaga acagttctgg aaaatagcac aagttatgaa    840
gaagccaaga atttattgac caagaccaag atattggccc cagcctactt tatcctggga    900
ggcaaccagt ctggggaagg ttgtgtgatt acacgagaca gaaaggaatc attggatgta    960
tatgaactcg atgctaagca gggtagatgg tatgtggtac aaacaaatta tgaccgttgg   1020
aaacatccct tcttccttga tgatcgcaga acgcctgcaa agatgtgtct gaaccgcacc   1080
agccaagaga atatctcatt tgaaaccatg tatgatgtcc tgtcaacaaa acctgtcctc   1140
aacaagctga ccgtatacac aaccttgata gatgttacca aaggtcaatt cgaaacttac   1200
ctgcgggact gccctgaccc ttgtataggt tggtga                            1236

<210> SEQ ID NO 7
<211> LENGTH: 1170
<212> TYPE: DNA
<213> ORGANISM: Artificial Sequence
<220> FEATURE:
<223> OTHER INFORMATION: synthetic oligomer

<400> SEQUENCE: 7
atgaactgct gcatcgggct gggagagaaa gctcgcgggt cccaccgggc ctcctaccca     60
agtctcagcg cgcttttcac cgaggcctca attctgggat ttggcagctt tgctgtgaaa    120
gcccaatgga cagaggactg cagaaaatca acctatcctc cttcaggacc aactgtcttc    180
cctgctgtta taaggtacag aggtgcagtt ccatggtaca ccataaatct tgacttacca    240
ccctacaaaa gatggcatga attgatgctt gacaaggcac cagtgcctgg cctacttggc    300
aactttcctg gcccttttga agaggaaatg aagggtattg ccgctgttac tgatatacct    360
ttaggagaga ttatttcatt caatattttt tatgaattat ttaccatttg tacttcaata    420
```

-continued

```
gtagcagaag acaaaaaagg tcatctaata catgggagaa acatggattt tggagtattt      480
cttgggtgga acataaataa tgatacctgg gtcataactg agcaactaaa acctttaaca      540
gtgaatttgg atttccaaag aaacaacaaa actgtcttca aggcttcaag ctttgctggc      600
tatgtgggca tgttaacagg attcaaacca ggactgttca gtcttacact gaatgaacgt      660
ttcagtataa atggtggtta tctgggtatt ctagaatgga ttctgggaaa gaaagatgtc      720
atgtggatag ggttcctcac tagaacagtt ctggaaaata gcacaagtta tgaagaagcc      780
aagaatttat tgaccaagac caagatattg gccccagcct actttatcct gggaggcaac      840
cagtctgggg aaggttgtgt gattacacga gacagaaagg aatcattgga tgtatatgaa      900
ctcgatgcta agcagggtag atggtatgtg gtacaaacaa attatgaccg ttggaaacat      960
cccttcttcc ttgatgatcg cagaacgcct gcaaagatgt gtctgaaccg caccagccaa     1020
gagaatatct catttgaaac catgtatgat gtcctgtcaa caaaacctgt cctcaacaag     1080
ctgaccgtat acacaacctt gatagatgtt accaaaggtc aattcgaaac ttacctgcgg     1140
gactgccctg acccttgtat aggttggtga                                      1170

<210> SEQ ID NO 8
<211> LENGTH: 2346
<212> TYPE: DNA
<213> ORGANISM: Artificial Sequence
<220> FEATURE:
<223> OTHER INFORMATION: synthetic oligomer

<400> SEQUENCE: 8
atggccaaac gcaccttctc taacttggag acattcctga ttttcctcct tgtaatgatg       60
agtgccatca cagtggccct tctcagcctc ttgtttatca ccagtgggac cattgaaaac      120
cacaaagatt taggaggcca ttttttttca accacccaaa gccctccagc cacccagggc      180
tccacagctg cccaacgctc cacagccacc cagcattcca cagccaccca gagctccaca      240
gccactcaaa cttctccagt gcctttaacc ccagagtctc tctatttca gaacttcagt      300 ggctaccata ttggtgttgg acgagctgac tgcacaggac aagtagcaga tatcaatttg      360
atgggctatg gcaaatccgg ccagaatgca cagggcatcc tcaccaggct atacagtcgt      420
gccttcatca tggcagaacc tgatgggtcc aatcgaacag tgtttgtcag catcgacata      480
ggcatggtat cacaaaggct caggctggag gtcctgaaca gactgcagag taaatatggc      540
tccctgtaca gaagagataa tgtcatcctg agtggcactc acactcattc aggtcctgca      600
ggatatttcc agtataccgt gtttgtaatt gccagtgaag gatttagcaa tcaaactttt      660
cagcacatgg tcactggtat cttgaagagc attgacatag cacacacaaa tatgaaacca      720
ggcaaaatct tcatcaataa aggaaatgtg gatggtgtgc agatcaacag aagtccgtat      780
tcttaccttc aaaatccgca gtcagagaga gcaaggtatt cttcaaatac agacaaggaa      840
atgatagttt tgaaaatggt agatttgaat ggagatgact tgggccttat cagctggttt      900
gccatccacc cggtcagcat gaacaacagt aaccatcttg taaacagtga caatgtgggc      960
tatgcatctt acctgcttga gcaagagaag aacaaaggat atctacctgg acagggcca      1020 tttgtagcag ccttttgcttc atcaaaccta ggagatgtgt cccccaacat tcttggacca     1080
cgttgcatca acacaggaga gtcctgtgat aacgccaata gcacttgtcc cattggtggg     1140
cctagcatgt gcattgctaa gggacctgga caggatatgt ttgacagcac acaaattata     1200
ggacgggcca tgtatcagag agcaaaggaa ctctatgcct ctgcctccca ggaggtaaca     1260
ggaccactgg cttcagcaca ccagtgggtg gatatgacag atgtgactgt ctggctcaat     1320
```

-continued

```
tccacacatg catcaaaaac atgtaaacca gcattgggct acagttttgc agctggcact    1380
attgatggag ttggaggcct caattttaca caggggaaaa cagaagggga tccattttgg    1440
gacaccattc gggaccagat cctgggaaag ccatctgaag aaattaaaga atgtcataaa    1500
ccaaagccca tccttcttca caccggagaa ctatcaaaac ctcacccctg gcatccagac    1560
attgttgatg ttcagattat tacccttggg tccttggcca taactgccat ccccggggag    1620
tttacgacca tgtctggacg aagacttcga gaggcagttc aagcagaatt tgcatctcat    1680
gggatgcaga acatgactgt tgttatttca ggtctatgca acgtctatac acattacatt    1740
accacttatg aagaatacca ggctcagcga tatgaggcag catcgacaat ttatggaccg    1800
cacacattat ctgcttacat tcagctcttc agaaaccttg ctaaggctat tgctacggac    1860
acggtagcca acctgagcag aggtccagaa cctccctttt tcaaacaatt aatagttcca    1920
ttaattccta gtattgtgga tagagcacca aaaggcagaa ctttcgggga tgtcctgcag    1980
ccagcaaaac ctgaatacag agtggggaa gttgctgaag ttatatttgt aggtgctaac    2040
ccgaagaatt cagtacaaaa ccagacccat cagaccttcc tcactgtgga gaaatatgag    2100
gctacttcaa catcgtggca gatagtgtgt aatgatgcct cctgggagac tcgtttttat    2160
tggcacaagg gactcctggg tctgagtaat gcaacagtgg aatggcatat tccagacact    2220
gcccagcctg gaatctacag aataagatat tttggacaca tcggaagca ggacattctg    2280 aagcctgctg tcatactttc atttgaaggc acttccccgg cttttgaagt tgtaactatt    2340
tagtga                                                               2346
```

```
<210> SEQ ID NO 9
<211> LENGTH: 2241
<212> TYPE: DNA
<213> ORGANISM: Artificial Sequence
<220> FEATURE:
<223> OTHER INFORMATION: synthetic oligomer

<400> SEQUENCE: 9
```

```
atggccaaac gcaccttctc taacttggag acattcctga ttttcctcct tgtaatgatg      60
agtgccatca cagtggccct tctcagcctc ttgtttatca ccagtgggac cattgaaaac     120
cacaaagatt taggaggcca ttttttttca accacccaaa gccctccagc cacccagggc     180
tccacagctg cccaacgctc cacagccacc cagcattcca cagccaccca gagctccaca     240
gccactcaaa cttctccagt gcctttaacc ccagagtctc ctctatttca gaacttcagt     300
ggctaccata ttggtgttgg acgagctgac tgcacaggac aagtagcaga tatcaatttg     360
atgggctatg gcaaatccgg ccagaatgca cagggcatcc tcaccaggct atacagtcgt     420
gccttcatca tggcagaacc tgatgggtcc aatcgaacag tgtttgtcag catcgacata     480
ggcatggtat cacaaaggct caggctggag gtcctgaaca gactgcagag taaatatggc     540
tccctgtaca aagagataa tgtcatcctg agtggcactc acactcattc aggtcctgca     600
ggatatttcc agtataccgt gtttgtaatt gccagtgaag gatttagcaa tcaaactttt     660
cagcacatgg tcactggtat cttgaagagc attgacatag cacacacaaa tatgaaacca     720
ggcaaaatct tcatcaataa aggaaatgtg gatggtgtgc agatcaacag aagtccgtat     780
tcttaccttc aaaatccgca gtcagagaga gcaaggtatt cttcaaatac agacaaggaa     840
atgatagttt tgaaaatggt agatttgaat ggagatgact tgggccttat cagctggttt     900
gccatccacc cggtcagcat gaacaacagt aaccatcttg taaacagtga caatgtgggc     960
```

```
tatgcatctt acctgcttga gcaagagaag aacaaaggat atctacctgg acaggggcca    1020
tttgtagcag cctttgcttc atcaaaccta ggagatgtgt cccccaacat tcttggacca    1080
cgttgcatca acacaggaga gtcctgtgat aacgccaata gcacttgtcc cattggtggg    1140
cctagcatgt gcattgctaa gggacctgga caggatatgt ttgacagcac acaaattata    1200
ggacgggcca tgtatcagag agcaaagtca aaaacatgta aaccagcatt gggctacagt    1260
tttgcagctg gcactattga tggagttgga ggcctcaatt ttacacaggg gaaaacagaa    1320
ggggatccat tttgggacac cattcgggac cagatcctgg gaaagccatc tgaagaaatt    1380
aaagaatgtc ataaaccaaa gcccatcctt cttcacaccg gagaactatc aaaacctcac    1440
ccctggcatc cagacattgt tgatgttcag attattaccc ttgggtcctt ggccataact    1500
gccatccccg gggagtttac gaccatgtct ggacgaagac ttcgagaggc agttcaagca    1560
gaatttgcat ctcatgggat gcagaacatg actgttgtta tttcaggtct atgcaacgtc    1620
tatacacatt acattaccac ttatgaagaa taccaggctc agcgatatga ggcagcatcg    1680
acaatttatg gaccgcacac attatctgct tacattcagc tcttcagaaa ccttgctaag    1740
gctattgcta cggacacggt agccaacctg agcagaggtc cagaacctcc ctttttcaaa    1800
caattaatag ttccattaat tcctagtatt gtggatagag caccaaaagg cagaactttc    1860
ggggatgtcc tgcagccagc aaaacctgaa tacagagtgg gggaagttgc tgaagttata    1920
tttgtaggtg ctaacccgaa gaattcagta caaaaccaga cccatcagac cttcctcact    1980
gtggagaaat atgaggctac ttcaacatcg tggcagatag tgtgtaatga tgcctcctgg    2040
gagactcgtt tttattggca caagggactc ctgggtctga gtaatgcaac agtggaatgg    2100
catattccag acactgccca gcctggaatc tacagaataa gatattttgg acacaatcgg    2160
aagcaggaca ttctgaagcc tgctgtcata ctttcatttg aaggcacttc cccggctttt    2220
gaagttgtaa ctatttagtg a                                             2241
```

```
<210> SEQ ID NO 10
<211> LENGTH: 501
<212> TYPE: DNA
<213> ORGANISM: Artificial Sequence
<220> FEATURE:
<223> OTHER INFORMATION: synthetic oligomer

<400> SEQUENCE: 10
atgaggcagc atcgacaatt tatggaccgc acgcattatc tgcttacatt cagctcttca      60
gaaaccttgc taaggctatt gctacgtatt gtggatagag caccaaaagg cagaactttc     120
ggggatgtcc tgcagccagc aaaacctgaa tacagagtgg gggaagttgc tgaagttata     180
tttgtaggtg ctaacccgaa gaattcagta caaaaccaga cccatcagac cttcctcact     240
gtggagaaat atgaggctac ttcaacatcg tggcagatag tgtgtaatga tgcctcctgg     300
gagactcgtt tttattggca caagggactc ctgggtctga gtaatgcaac agtggaatgg     360
catattccag acactgccca gcctggaatc tacagaataa gatattttgg acacaatcgg     420
aagcaggaca ttctgaagcc tgctgtcata ctttcatttg aaggcacttc cccggctttt     480
gaagttgtaa ctatttagtg a                                               501
```

```
<210> SEQ ID NO 11
<211> LENGTH: 972
<212> TYPE: DNA
<213> ORGANISM: Artificial Sequence
<220> FEATURE:
<223> OTHER INFORMATION: synthetic oligomer
```

-continued

```
<400> SEQUENCE: 11
atggtagcca acctgagcag aggtccagaa cctccctttt tcaaacaatt aatagttcca      60
ttaattccta gtattgtgga tagagcacca aaaggcagaa ctttcgggga tgtcctgcag     120
ccagcaaaac ctgaatacag agtgggggaa gttgctgaag ttatatttgt aggtgctaac     180
ccgaagaatt cagtacaaaa ccagacccat cagaccttcc tcactgtgga gaaatatgag     240
gctacttcaa catcgtggca gatagtgtgt aatgatgcct cctgggagac tcgtttttat     300
tggcacaagg gactcctggg tctgagtaat gcaacagtgg aatggcatat tccagacact     360
gcccagcctg gaatctacag aataagatat tttggacaca atcggaagca ggacattctg     420
aagcctgctg tcatactttc atttgaaggc acttccccgg cttttgaagt tgtaactatt     480
tagtgaatgg tagccaacct gagcagaggt ccagaacctc cctttttcaa acaattaata     540
gttccattaa ttcctagtat tgtggataga gcaccaaaag cagaacttt cggggatgtc     600 ctgcagccag caaaacctga atacagagtg ggggaagttg ctgaagttat atttgtaggt     660
gctaacccga agaattcagt acaaaaccag acccatcaga ccttcctcac tgtggagaaa     720
tatgaggcta cttcaacatc gtggcagata gtgtgtaatg atgcctcctg ggagactcgt     780
ttttattggc acaagggact cctgggtctg agtaatgcaa cagtggaatg gcatattcca     840
gacactgccc agcctggaat ctacagaata agatattttg gacacaatcg gaagcaggac     900
attctgaagc tgctgtcat actttcattt gaaggcactt ccccggcttt tgaagttgta     960
actatttagt ga                                                         972

<210> SEQ ID NO 12
<211> LENGTH: 483
<212> TYPE: DNA
<213> ORGANISM: Artificial Sequence
<220> FEATURE:
<223> OTHER INFORMATION: synthetic oligomer

<400> SEQUENCE: 12
atggtagcca acctgagcag aggtccagaa cctccctttt tcaaacaatt aatagttcca      60
ttaattccta gtattgtgga tagagcacca aaaggcagaa ctttcgggga tgtcctgcag     120
ccagcaaaac ctgaatacag agtgggggaa gttgctgaag ttatatttgt aggtgctaac     180
ccgaagaatt cagtacaaaa ccagacccat cagaccttcc tcactgtgga gaaatatgag     240
gctacttcaa catcgtggca gatagtgtgt aatgatgcct cctgggagac tcgtttttat     300
tggcacaagg gactcctggg tctgagtaat gcaacagtgg aatggcatat tccagacact     360
gcccagcctg gaatctacag aataagatat tttggacaca atcggaagca ggacattctg     420
aagcctgctg tcatactttc atttgaaggc acttccccgg cttttgaagt tgtaactatt     480
tag                                                                   483

<210> SEQ ID NO 13
<211> LENGTH: 795
<212> TYPE: DNA
<213> ORGANISM: Artificial Sequence
<220> FEATURE:
<223> OTHER INFORMATION: synthetic oligomer

<400> SEQUENCE: 13
atgcctagca tcttcgccta tcagagctcc gaggtggact ggtgtgagag caacttccag      60
tactcggagc tggtggccga gttctacaac acgttctcca atatcccctt cttcatcttc     120
```

```
gggccactga tgatgctcct gatgcacccg tatgcccaga agcgctcccg ctacatttac      180
gttgtctggg tcctcttcat gatcataggc ctgttctcca tgtatttcca catgacgctc      240
agcttcctgg gccagctgct ggacgagatc gccatcctgt ggctcctggg cagtggctat      300
agcatatgga tgccccgctg ctatttcccc tccttccttg gggggaacag gtcccagttc      360
atccgcctgg tcttcatcac cactgtggtc agcacccttc tgtccttcct gcggcccacg      420
gtcaacgcct acgccctcaa cagcattgcc ctgcacattc tctacatcgt gtgccaggag      480
tacaggaaga ccagcaataa ggagcttcgg cacctgattg aggtctccgt ggttttatgg      540
gctgttgctc tgaccagctg gatcagtgac cgtctgcttt gcagcttctg gcagaggatt      600
catttcttct atctgcacag catctggcat gtgctcatca gcatcacctt cccttatggc      660
atggtcacca tggccttggt ggatgccaac tatgagatgc aggtgaaac cctcaaagtc      720 cgctactggc ctcgggacag ttggcccgtg gggctgccct acgtggaaat ccggggtgat      780
gacaaggact gctga                                                       795

<210> SEQ ID NO 14
<211> LENGTH: 828
<212> TYPE: DNA
<213> ORGANISM: Artificial Sequence
<220> FEATURE:
<223> OTHER INFORMATION: synthetic oligomer

<400> SEQUENCE: 14
atgggcgccc cgcactggtg ggaccagctg caggctggta gctcggaggt ggactggtgc       60
gaggacaact acaccatcgt gcctgctatc gccgagttct acaacacgat cagcaatgtc      120 ttattttttca ttttaccgcc catctgcatg tgcttgtttc gtcagtatgc aacatgcttc      180
aacagtggca tctacttaat ctggactctt ttggttgtag tgggaattgg atccgtctac      240
ttccatgcaa cccttagttt cttgggtcag atgcttgatg aacttgcagt cctttgggtt      300
ctgatgtgtg ctttggccat gtggttcccc agaaggtatc taccaaagat ctttcggaat      360
gaccggggta ggttcaaggt ggtggtcagt gtcctgtctg cggttacgac gtgcctggca      420
tttgtcaagc ctgccatcaa caacatctct ctgatgaccc tggagttcc ttgcactgca      480 ctgctcatcg cagagctaaa gaggtgtgac aacatgcgtg tgtttaagct gggcctcttc      540
tcgggcctct ggtggaccct ggccctgttc tgctggatca gtgaccgagc tttctgcgag      600
ctgctgtcat ccttcaactt cccctacctg cactgcatgt ggcacatcct catctgcctt      660
gctgcctacc tgggctgtgt atgctttgcc tactttgatg ctgcctcaga gattcctgag      720
caaggccctg tcatcaagtt ctggcccaat gagaaatggg ccttcattgg tgtcccctat      780
gtgtccctcc tgtgtgccaa caagaaatca tcagtcaaga tcacgtga                   828

<210> SEQ ID NO 15
<211> LENGTH: 804
<212> TYPE: DNA
<213> ORGANISM: Artificial Sequence
<220> FEATURE:
<223> OTHER INFORMATION: synthetic oligomer

<400> SEQUENCE: 15
atggctccgg ccgcggaccg agagggctac tggggcccca cgacctccac gctggactgg       60
tgcgaggaga actactccgt gacctggtac atcgccgagt tctggaatac agtgagtaac      120
ctgatcatga ttataacctcc aatgttcggt gcagttcaga gtgttagaga cggtctggaa      180
aagcggtaca ttgcttctta tttagcactc acagtggtag gaatgggatc ctggtgcttc      240
```

-continued

```
cacatgactc tgaaatatga aatgcagcta ttggatgaac tcccaatgat atacagctgt      300
tgcatatttg tgtactgcat gtttgaatgt ttcaagatca agaactcagt aaactaccat      360 ctgctttta ccttagttct attcagttta atagtaacca cagtttacct taaggtaaaa      420
gagccgatat tccatcaggt catgtatgga atgttggtct ttacattagt acttcgatct      480
atttatattg ttacatgggt ttatccatgg cttagaggac tgggttatac atcattgggt      540
atatttttat tgggattttt attttggaat atagataaca tattttgtga gtcactgagg      600
aactttcgaa agaaggtacc acctatcata ggtattacca cacaatttca tgcatggtgg      660 catatttaa ctggccttgg ttcctatctt cacatccttt tcagtttgta tacaagaaca      720
ctttacctga gatataggcc aaaagtgaag tttctctttg gaatctggcc agtgatcctg      780
tttgagcctc tcaggaagca ttga                                              804
```

```
<210> SEQ ID NO 16
<211> LENGTH: 693
<212> TYPE: DNA
<213> ORGANISM: Artificial Sequence
<220> FEATURE:
<223> OTHER INFORMATION: synthetic oligomer

<400> SEQUENCE: 16
atggctccgg ccgcggaccg agagggctac tggggcccca cgacctccac gctggactgg       60
tgcgaggaga actactccgt gacctggtac atcgccgagt tcttggtagg aatgggatcc      120
tggtgcttcc acatgactct gaaatatgaa atgcagctat tggatgaact cccaatgata      180
tacagctgtt gcatatttgt gtactgcatg tttgaatgtt tcaagatcaa gaactcagta      240
aactaccatc tgcttttac cttagttcta ttcagtttaa tagtaaccac agtttacctt      300
aaggtaaaag agccgatatt ccatcaggtc atgtatggaa tgttggtctt tacattagta      360
cttcgatcta tttatattgt tacatgggtt tatccatggc ttagaggact gggttataca      420
tcattgggta tattttatt gggattttta ttttggaata tagataacat attttgtgag      480
tcactgagga actttcgaaa gaaggtacca cctatcatag gtattaccac acaatttcat      540
gcatggtggc atattttaac tggccttggt cctatcttc acatcctttt cagtttgtat      600
acaagaacac tttacctgag atataggcca aaagtgaagt ttctctttgg aatctggcca      660
gtgatcctgt ttgagcctct caggaagcat tga                                   693
```

```
<210> SEQ ID NO 17
<211> LENGTH: 519
<212> TYPE: DNA
<213> ORGANISM: Artificial Sequence
<220> FEATURE:
<223> OTHER INFORMATION: synthetic oligomer

<400> SEQUENCE: 17
atgatataca gctgttgcat atttgtgtac tgcatgtttg aatgtttcaa gatcaagaac       60
tcagtaaact accatctgct ttttaccta gttctattca gtttaatagt aaccacagtt      120
taccttaagg taaaagagcc gatattccat caggtcatgt atggaatgtt ggtctttaca      180
ttagtacttc gatctatttta tattgttaca tgggtttatc catggcttag aggactgggt      240
tatacatcat tgggtatatt tttattggga ttttttatttt ggaatataga taacatattt      300
tgtgagtcac tgaggaactt tcgaaagaag gtaccaccta tcataggtat taccacacaa      360
tttcatgcat ggtggcatat tttaactggc cttggttcct atcttcacat cctttttcagt      420
```

-continued

```
ttgtatacaa gaacacttta cctgagatat aggccaaaag tgaagtttct ctttggaatc      480
tggccagtga tcctgtttga gcctctcagg aagcattga                            519

<210> SEQ ID NO 18
<211> LENGTH: 1965
<212> TYPE: DNA
<213> ORGANISM: Artificial Sequence
<220> FEATURE:
<223> OTHER INFORMATION: synthetic oligomer

<400> SEQUENCE: 18
atgaatggac accttgaagc agaggagcag caggaccaga ggccagacca ggagctgacc       60
gggagctggg gccacgggcc taggagcacc ctggtcaggg ctaaggccat ggccccgccc      120
ccaccgccac tggctgccag cacccccgctc ctccatggcg agtttggctc ctacccagcc     180
cgaggcccac gctttgccct cacccttaca tcgcaggccc tgcacataca gcggctgcgc      240
cccaaacctg aagccaggcc ccggggtggc ctggtcccgt tggccgaggt ctcaggctgc      300
tgcaccctgc gaagccgcag cccctcagac tcagcggcct acttctgcat ctacacctac      360
cctcggggcc ggcgcggggc ccggcgcaga gccactcgca ccttccgggc agatgggggcc     420 gccacctacg aagagaaccg tgccgaggcc cagcgctggg ccactgccct cacctgtctg      480
ctccgaggac tgccactgcc cggggatggg gagatcaccc ctgacctgct acctcggccg      540
ccccggttgc ttctattggt caatcccttt ggggtcgggg gcctggcctg gcagtggtgt      600
aagaaccacg tgcttcccat gatctctgaa gctgggctgt ccttcaacct catccagaca      660
gaacgacaga accacgcccg ggagctggtc caggggctga gcctgagtga gtgggatggc      720
atcgtcacgg tctcgggaga cgggctgctc catgaggtgc tgaacgggct cctagatcgc      780
cctgactggg aggaagctgt gaagatgcct gtgggcatcc tcccctgcgg ctcgggcaac      840
gcgctggccg gagcagtgaa ccagcacggg ggatttgagc cagccctggg cctcgacctg      900
ttgctcaact gctcactgtt gctgtgccgg ggtggtggcc acccactgga cctgctctcc      960
gtgacgctgg cctcgggctc ccgctgtttc tccttcctgt ctgtggcctg gggcttcgtg    1020
tcagatgtgg atatccagag cgagcgcttc agggccttgg gcagtgcccg cttcacactg    1080
ggcacggtgc tgggcctcgc cacactgcac acctaccgcg gacgcctctc ctacctcccc    1140
gccactgtgg aacctgcctc gcccacccct gcccatagcc tgcctcgtgc caagtcggag    1200
ctgaccctaa ccccagaccc agccccgccc atggcccact cacccctgca tcgttctgtg    1260
tctgacctgc ctcttcccct gccccagcct gccctggcct ctcctggctc gccagaaccc    1320
ctgcccatcc tgtccctcaa cggtggggggc ccagagctgg ctggggactg gggtgggggct   1380 ggggatgctc cgctgtcccc ggacccactg ctgtcttcac ctcctggctc tcccaaggca    1440
gctctacact cacccgtctc cgaagggggcc cccgtaattc ccccatcctc tgggctccca    1500
cttcccaccc ctgatgcccg ggtaggggcc tccacctgcg gcccgcccga ccacctgctg    1560
cctccgctgg gcacccccgct gccccagac tgggtgacgg tggaggggga ctttgtgctc    1620
atgttggcca tctcgcccag ccacctaggc gctgacctgg tggcagctcc gcatgcgcgc    1680
ttcgacgacg gcctggtgca cctgtgctgg gtgcgtagcg gcatctcgcg ggctgcgctc    1740
ctgcgccttt tcttggccat ggagcgtggt agccacttca gcctgggctg tccgcagctg    1800
ggctacgccg cggccgtgc cttccgccta gagccgctca caccacgcgg cgtgctcaca    1860
gtggacgggg agcaggtgga gtatgggccg ctacaggcac agatgcaccc tggcatcggt    1920
acactgctca ctgggcctcc tggctgcccg gggcgggagc cctga                    1965
```

```
<210> SEQ ID NO 19
<211> LENGTH: 1614
<212> TYPE: DNA
<213> ORGANISM: Artificial Sequence
<220> FEATURE:
<223> OTHER INFORMATION: synthetic oligomer

<400> SEQUENCE: 19 atggggggcga cggggggcggc ggagccgctg caatccgtgc tgtgggtgaa gcagcagcgc      60
tgcgccgtga gcctggagcc cgcgcgggct ctgctgcgct ggtggcggag cccggggccc     120
ggagccggcg cccccggcgc ggatgcctgc tctgtgcctg tatctgagat catcgccgtt     180
gaggaaacag acgttcacgg gaaacatcaa ggcagtggaa aatggcagaa aatggaaaag     240
ccttacgctt ttacagttca ctgtgtaaag agagcacgac ggcaccgctg gaagtgggcg     300
caggtgactt tctggtgtcc agaggagcag ctgtgtcact tgtggctgca gaccctgcgg     360
gagatgctgg agaagctgac gtccagacca aagcatttac tggtatttat caacccgttt     420
ggaggaaaag gacaaggcaa gcggatatat gaaagaaaag tggcaccact gttcacctta     480
gcctccatca ccactgacat catcgttact gaacatgcta atcaggccaa ggagactctg     540
tatgagatta acatagacaa atacgacggc atcgtctgtg tcggcggaga tggtatgttc     600
agcgaggtgc tgcacggtct gattgggagg acgcagagga gcgccggggt cgaccagaac     660
caccccgggg ctgtgctggt ccccagtagc ctccggattg gaatcattcc cgcagggtca     720
acggactgcg tgtgttactc caccgtgggc accagcgacg cagaaacctc ggcgctgcat     780
atcgttgttg gggactcgct ggccatggat gtgtcctcag tccaccacaa cagcacactc     840
cttcgctact ccgtgtccct gctgggctac ggcttctacg gggacatcat caaggacagt     900
gagaagaaac ggtggttggg tcttgccaga tacgactttt caggtttaaa gaccttcctc     960
tcccaccact gctatgaagg gacagtgtcc ttcctccctg cacaacacac ggtgggatct    1020
ccaagggata ggaagccctg ccgggcagga tgctttgttt gcaggcaaag caagcagcag    1080
ctggaggagg agcagaagaa agcactgtat ggtttggaag ctgcggagga cgtgggaggag    1140 tggcaagtcg tctgtgggaa gtttctggcc atcaatgcca caaacatgtc ctgtgcttgt    1200
cgccggagcc ccaggggcct ctccccggct gcccacttgg gagacgggtc ttctgacctc    1260
atcctcatcc ggaaatgctc caggttcaat tttctgagat ttctcatcag gcacaccaac    1320
cagcaggacc agtttgactt cacttttgtt gaagtttatc gcgtcaagaa attccagttt    1380
acgtcgaagc acatggagga tgaggacagc gacctcaagg agggggggaa gaagcgcttt    1440
gggcacattt gcagcagcca cccctcctgc tgctgcaccg tctccaacag ctcctggaac    1500
tgcgacgggg aggtcctgca cagccctgcc atcgaggtca gagtccactg ccagctggtt    1560
cgactctttg cacgaggaat tgaagagaat ccgaagccag actcacacag ctga          1614

<210> SEQ ID NO 20
<211> LENGTH: 4779
<212> TYPE: DNA
<213> ORGANISM: Artificial Sequence
<220> FEATURE:
<223> OTHER INFORMATION: synthetic oligomer
<220> FEATURE:
<221> NAME/KEY: misc_feature
<222> LOCATION: (980)..(982)
<223> OTHER INFORMATION: n is a, c, g, or t

<400> SEQUENCE: 20
```

-continued

```
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact       120
aggggttcct tgtagttaat gattaacccg ccatgctact tatctacgta gccatgctct       180
aggaagatcg gaattcgccc ttaagctagc tagttattaa tagtaatcaa ttacggggtc       240
attagttcat agcccatata tggagttccg cgttacataa cttacggtaa atggcccgcc       300
tggctgaccg cccaacgacc cccgcccatt gacgtcaata atgacgtatg ttcccatagt       360
aacgccaata gggactttcc attgacgtca atgggtggag tatttacggt aaactgccca       420
cttggcagta catcaagtgt atcatatgcc aagtacgccc cctattgacg tcaatgacgg       480
taaatggccc gcctggcatt atgcccagta catgacctta tgggactttc ctacttggca       540
gtacatctac gtattagtca tcgctattac catggtgatg cggttttggc agtacatcaa       600
tgggcgtgga tagcggtttg actcacgggg atttccaagt ctccacccca ttgacgtcaa       660
tgggagtttg ttttggcacc aaaatcaacg ggactttcca aaatgtcgta acaactccgc       720
cccattgacg caaatgggcg gtaggcgtgt acggtgggag gtctatataa gcagagctgg       780
tttagtgaac cgtcagatcc tgcagaagtt ggtcgtgagg cactgggcag gtaagtatca       840
aggttacaag acaggtttaa ggagaccaat agaaactggg cttgtcgaga cagagaagac       900
tcttgcgttt ctgataggca cctattggtc ttactgacat ccactttgcc tttctctcca       960
caggtgtcca ggcggccgcn nnggatccaa tcaacctctg gattacaaaa tttgtgaaag      1020
attgactggt attcttaact atgttgctcc ttttacgcta tgtggatacg ctgctttaat      1080
gcctttgtat catgctattg cttcccgtat ggctttcatt ttctcctcct tgtataaatc      1140
ctggttgctg tctctttatg aggagttgtg gcccgttgtc aggcaacgtg gcgtggtgtg      1200
cactgtgttt gctgacgcaa ccccccactgg ttggggcatt gccaccacct gtcagctcct      1260
ttccgggact ttcgctttcc ccctccctat gccacggcg gaactcatcg ccgcctgcct      1320
tgcccgctgc tggacagggg ctcggctgtt gggcactgac aattccgtgg tgttgtcggg      1380
gaaatcatcg tcctttcctt ggctgctcgc ctgtgttgcc acctggattc tgcgcgggac      1440
gtccttctgc tacgtccctt cggccctcaa tccagcggac cttccttccc gcggcctgct      1500
gccggctctg cggcctcttc cgcgtcttcg agatctgcct cgactgtgcc ttctagttgc      1560
cagccatctg ttgtttgccc ctccccgtg ccttccttga ccctggaagg tgccactccc      1620
actgtccttt cctaataaaa tgaggaaatt gcatcgcatt gtctgagtag gtgtcattct      1680
attctggggg gtggggtggg gcaggacagc aaggggagg attgggaaga caatagcagg      1740
catgctgggg actcgagtta agggcgaatt cccgataagg atcttcctag agcatggcta      1800
cgtagataag tagcatggcg ggttaatcat taactacaag gaacccctag tgatggagtt      1860
ggccactccc tctctgcgcg ctcgctcgct cactgaggcc gggcgaccaa aggtcgcccg      1920
acgcccgggc tttgcccggg cggcctcagt gagcgagcga gcgcgcagcc ttaattaacc      1980
taattcactg gccgtcgttt tacaacgtcg tgactgggaa aaccctggcg ttacccaact      2040
taatcgcctt gcagcacatc cccctttcgc cagctggcgt aatagcgaag aggcccgcac      2100
cgatcgccct tcccaacagt tgcgcagcct gaatggcgaa tgggacgcgc cctgtagcgg      2160
cgcattaagc gcggcgggtg tggtggttac gcgcagcgtg accgctacac ttgccagcgc      2220
cctagcgccc gctcctttcg ctttcttccc ttcctttctc gccacgttcg ccggctttcc      2280
ccgtcaagct ctaaatcggg ggctcccttt agggttccga tttagtgctt tacggcacct      2340
cgaccccaaa aaacttgatt agggtgatgg ttcacgtagt gggccatcgc cctgatagac      2400
```

```
ggtttttcgc cctttgacgt tggagtccac gttctttaat agtggactct tgttccaaac   2460
tggaacaaca ctcaacccta tctcggtcta ttcttttgat ttataaggga ttttgccgat   2520
ttcggcctat tggttaaaaa atgagctgat ttaacaaaaa tttaacgcga attttaacaa   2580
aatattaacg tttataattt caggtggcat cttttcggga aatgtgcgcg gaacccctat   2640
ttgtttattt ttctaaatac attcaaatat gtatccgctc atgagacaat aaccctgata   2700
aatgcttcaa taatattgaa aaaggaagag tatgagtatt caacatttcc gtgtcgccct   2760
tattcccttt tttgcggcat tttgccttcc tgttttttgct cacccagaaa cgctggtgaa   2820
agtaaaagat gctgaagatc agttgggtgc acgagtgggt tacatcgaac tggatctcaa   2880
tagtggtaag atccttgaga gttttcgccc cgaagaacgt tttccaatga tgagcacttt   2940
taaagttctg ctatgtggcg cggtattatc ccgtattgac gccgggcaag agcaactcgg   3000
tcgccgcata cactattctc agaatgactt ggttgagtac tcaccagtca cagaaaagca   3060
tcttacggat ggcatgacag taagagaatt atgcagtgct gccataacca tgagtgataa   3120
cactgcggcc aacttacttc tgacaacgat cggaggaccg aaggagctaa ccgcttttttt   3180 gcacaacatg gggatcatg taactcgcct tgatcgttgg gaaccggagc tgaatgaagc   3240
cataccaaac gacgagcgtg acaccacgat gcctgtagta atggtaacaa cgttgcgcaa   3300
actattaact ggcgaactac ttactctagc ttcccggcaa caattaatag actggatgga   3360
ggcggataaa gttgcaggac cacttctgcg ctcggccctt ccggctggct ggtttattgc   3420
tgataaatct ggagccggtg agcgtgggtc tcgcggtatc attgcagcac tggggccaga   3480
tggtaagccc tcccgtatcg tagttatcta cacgacgggg agtcaggcaa ctatggatga   3540
acgaaataga cagatcgctg agataggtgc ctcactgatt aagcattggt aactgtcaga   3600
ccaagtttac tcatatatac tttagattga tttaaaactt catttttaat ttaaaaggat   3660
ctaggtgaag atcctttttg ataatctcat gaccaaaatc ccttaacgtg agttttcgtt   3720
ccactgagcg tcagaccccg tagaaaagat caaaggatct tcttgagatc cttttttttct   3780 gcgcgtaatc tgctgcttgc aaacaaaaaa accaccgcta ccagcggtgg tttgtttgcc   3840
ggatcaagag ctaccaactc tttttccgaa ggtaactggc ttcagcagag cgcagatacc   3900
aaatactgtc cttctagtgt agccgtagtt aggccaccac ttcaagaact ctgtagcacc   3960
gcctacatac ctcgctctgc taatcctgtt accagtggct gctgccagtg gcgataagtc   4020
gtgtcttacc gggttggact caagacgata gttaccggat aaggcgcagc ggtcgggctg   4080
aacggggggt tcgtgcacac agcccagctt ggagcgaacg acctacaccg aactgagata   4140
cctacagcgt gagctatgag aaagcgccac gcttcccgaa gggagaaagg cggacaggta   4200
tccggtaagc ggcagggtcg aacaggaga gcgcacgagg gagcttccag ggggaaacgc   4260
ctggtatctt tatagtcctg tcgggtttcg ccacctctga cttgagcgtc gatttttgtg   4320
atgctcgtca ggggggcgga gcctatggaa aaacgccagc aacgcggcct ttttacggtt   4380
cctggccttt tgctgcggtt ttgctcacat gttctttcct gcgttatccc ctgattctgt   4440
ggataaccgt attaccgcct ttgagtgagc tgataccgct cgccgcagcc gaacgaccga   4500
gcgcagcgag tcagtgagcg aggaagcgga agagcgccca atacgcaaac cgcctctccc   4560
cgcgcgttgg ccgattcatt aatgcagctg gcacgacagg tttcccgact ggaaagcggg   4620
cagtgagcgc aacgcaatta atgtgagtta gctcactcat taggcacccc aggctttaca   4680
ctttatgctt ccggctcgta tgttgtgtgg aattgtgagc ggataacaat ttcacacagg   4740
```
aaacagctat gaccatgatt acgccagatt taattaagg                                    4779

<210> SEQ ID NO 21
<211> LENGTH: 22
<212> TYPE: DNA
<213> ORGANISM: Artificial Sequence
<220> FEATURE:
<223> OTHER INFORMATION: synthetic oligo

<400> SEQUENCE: 21
acaggattca aaccaggact gt                                                      22

<210> SEQ ID NO 22
<211> LENGTH: 20
<212> TYPE: DNA
<213> ORGANISM: Artificial Sequence
<220> FEATURE:
<223> OTHER INFORMATION: synthetic oligo

<400> SEQUENCE: 22
tgggcatctt tccttccgaa                                                         20

<210> SEQ ID NO 23
<211> LENGTH: 22
<212> TYPE: DNA
<213> ORGANISM: Artificial Sequence
<220> FEATURE:
<223> OTHER INFORMATION: synthetic oligo

<400> SEQUENCE: 23
tgacaggatt caaaccagga ct                                                      22

<210> SEQ ID NO 24
<211> LENGTH: 20
<212> TYPE: DNA
<213> ORGANISM: Artificial Sequence
<220> FEATURE:
<223> OTHER INFORMATION: synthetic oligo

<400> SEQUENCE: 24
ctgggcatct ttccttccga                                                         20

<210> SEQ ID NO 25
<211> LENGTH: 22
<212> TYPE: DNA
<213> ORGANISM: Artificial Sequence
<220> FEATURE:
<223> OTHER INFORMATION: synthetic oligo

<400> SEQUENCE: 25
atactcaccg aacggaagaa cc                                                      22

<210> SEQ ID NO 26
<211> LENGTH: 22
<212> TYPE: DNA
<213> ORGANISM: Artificial Sequence
<220> FEATURE:
<223> OTHER INFORMATION: synthetic oligo

<400> SEQUENCE: 26
ccattagccc attcaccacc tc                                                      22

<210> SEQ ID NO 27
<211> LENGTH: 21
<212> TYPE: DNA
<213> ORGANISM: Artificial Sequence
<220> FEATURE:
<223> OTHER INFORMATION: synthetic oligo

<400> SEQUENCE: 27
actgatactc accgaacgga a                                              21

<210> SEQ ID NO 28
<211> LENGTH: 21
<212> TYPE: DNA
<213> ORGANISM: Artificial Sequence
<220> FEATURE:
<223> OTHER INFORMATION: synthetic oligo

<400> SEQUENCE: 28
cattagccca ttcaccacct c                                              21

<210> SEQ ID NO 29
<211> LENGTH: 20
<212> TYPE: DNA
<213> ORGANISM: Artificial Sequence
<220> FEATURE:
<223> OTHER INFORMATION: synthetic oligo

<400> SEQUENCE: 29
cacagccaac agtctccaaa                                                20

<210> SEQ ID NO 30
<211> LENGTH: 19
<212> TYPE: DNA
<213> ORGANISM: Artificial Sequence
<220> FEATURE:
<223> OTHER INFORMATION: synthetic oligo

<400> SEQUENCE: 30
tctgagtata agccgccca                                                 19

<210> SEQ ID NO 31
<211> LENGTH: 19
<212> TYPE: DNA
<213> ORGANISM: Artificial Sequence
<220> FEATURE:
<223> OTHER INFORMATION: synthetic oligo

<400> SEQUENCE: 31
atagaccgag cacagccaa                                                 19

<210> SEQ ID NO 32
<211> LENGTH: 21
<212> TYPE: DNA
<213> ORGANISM: Artificial Sequence
<220> FEATURE:
<223> OTHER INFORMATION: synthetic oligo

<400> SEQUENCE: 32
gaaccttctc aggattgagg t                                              21

<210> SEQ ID NO 33
<211> LENGTH: 21
<212> TYPE: DNA
<213> ORGANISM: Artificial Sequence
<220> FEATURE:
<223> OTHER INFORMATION: synthetic oligo

<400> SEQUENCE: 33
taacgaacga gactctggca t                                              21

-continued

```
<210> SEQ ID NO 34
<211> LENGTH: 22
<212> TYPE: DNA
<213> ORGANISM: Artificial Sequence
<220> FEATURE:
<223> OTHER INFORMATION: synthetic oligo

<400> SEQUENCE: 34
cggacatcta agggcatcac ag                                              22
```

Anc80 ENCODING
SPHINGOLIPID-METABOLIZING PROTEINS

CROSS-REFERENCE TO RELATED APPLICATIONS

This application is a national stage application under 35 U.S.C. § 371 of International Application No. PCT/US2019/021201, filed Mar. 7, 2019, and published as WO 2020/005341 on Jan. 2, 2020, which claims the benefit of U.S. provisional application No. 62/692,185, filed Jun. 29, 2018. The entire contents of each of the prior applications are hereby incorporated by reference in their entirety.

SEQUENCE LISTING

The instant application contains a Sequence Listing, created on Dec. 18, 2018; the file, in ASCII format, is designated 3710047P_SequenceListing_ST25.txt and is 39.9 kilobytes in size. The file is hereby incorporated by reference in its entirety into the instant application.

TECHNICAL FIELD

The present disclosure relates generally to the use of sphingolipid-metabolizing proteins to improve the survival of mammalian cells. Exposure to sphingolipid metabolizing proteins such as acid ceramidase protein or expression of sphingolipid metabolizing proteins from an Anc80 vector inhibits cell death and/or senescence, preserves and restores normal cellular function, and prolongs survival of cells.

BACKGROUND OF THE DISCLOSURE

Ceramides are bioactive lipid mediators that influence cell proliferation, differentiation, adhesion and migration. These important cellular lipids are involved in signal transduction pathways such as cell death, senescence and the biosynthesis of other complex sphingolipids There are several studies that support the association of ceramide with cellular and organismal aging. High levels of cellular ceramides can trigger cell death or senescence while ceramide metabolites, such as ceramide-1-phosphate and sphingosine-1-phosphate (S1P), are associated with cell survival and proliferation.

In acute myocardial infarction (MI), for example, the level of lipids in the patient's blood can serve to predict the risk for complication. In particular, high levels of ceramides have been associated with a higher probability of recurring events and mortality.

Therefore, the ability to moderate ceramide to inhibit cell death and to prevent or reverse senescence may be important therapeutically to promote normal cell function and survival.

Though there are several pathways to synthesize ceramide, there is only one way to physiologically hydrolyze it; ceramide can be hydrolyzed into sphingosine by active ceramidase enzymes, including acid ceramidase (AC). The hydrolysis of ceramide produces sphingosine, which is rapidly converted to S1P, a "pro-survival" lipid. We have previously shown that administration of recombinant acid ceramidase (AC) (see U.S. Pat. No. 8,961,962 to Schuchman et al., herein incorporated by reference) promotes ex vivo survival of cells.

However, what is needed is a gene delivery method that achieves long-term expression of a sphingolipid-metabolizing enzyme in mammalian cells in vivo to inhibit cell death and senescence and initiate survival.

SUMMARY OF THE DISCLOSURE

The present disclosure provides a method for promoting survival and restoring function of cells or tissue in vitro or in vivo by administration of a viral vector that encodes a sphingolipid-metabolizing protein, and/or of a protein. In one embodiment, the disclosure relates to a method for promoting survival and restoring function of cells or tissue in vivo by administration of a sphingolipid-metabolizing protein directly to the cell, cells or tissue.

In a related aspect, the disclosure relates to a method to preserve and restore function to cardiac cells following ischemia, reperfusion injury, myocardial infarction (MI), pulmonary arterial hypertension (PAH), or other stress-related events comprising contacting said cardiac cells in vivo with a sphingolipid-metabolizing protein or an Anc80 viral vector encoding a sphingolipid-metabolizing protein.

In a related aspect, the disclosure relates to a method for preserving and/or restoring heart function in a subject following MI, the method comprising administering to the subject a therapeutically effective amount of a sphingolipid-metabolizing protein, an Anc80 viral vector encoding a sphingolipid-metabolizing protein, or a combination thereof.

The sphingolipid-metabolizing protein is selected from the group consisting of (1) a ceramidase; (2) sphingosine kinase (SPHK); (3) sphingosine-1-phosphate receptor (SIPR); (4) ceramidase kinase (CERK) or a combination of (1), (2), (3), and (4).

In one embodiment, the sphingolipid-metabolizing protein is a ceramidase. In one embodiment the sphingolipid-metabolizing protein is an acid ceramidase. In one embodiment, the sphingolipid-metabolizing protein is a neutral ceramidase. In yet another embodiment, the sphingolipid-metabolizing protein is an alkaline ceramidase. In one embodiment, ceramidase is encoded by a nucleic acid selected from the group consisting of SEQ ID NO: 1, SEQ ID NO: 6, SEQ ID NO: 7, SEQ ID NO: 8, SEQ ID NO: 9, SEQ ID NO: 10, SEQ ID NO: 11 and SEQ ID NO: 12.

In yet another aspect, the disclosure relates to a method in which the vector encoding the sphingolipid-metabolizing protein is Anc80. In one embodiment, the nucleotide sequence of Anc80 that encodes the sphingolipid-metabolizing protein comprises the nucleotide sequence of SEQ ID NO: 20.

In another related aspect, the disclosure relates to a pharmaceutical composition comprising an Anc80 viral vector encoding a sphingolipid-metabolizing protein and a pharmaceutically acceptable carrier.

In one embodiment, the sphingolipid-metabolizing protein is a ceramidase. In one embodiment, the sphingolipid-metabolizing protein is an acid ceramidase. In one embodiment, the sphingolipid-metabolizing protein is a neutral ceramidase. In yet another embodiment, the sphingolipid-metabolizing protein is an alkaline ceramidase.

In yet another related aspect, the disclosure relates to a sphingolipid-metabolizing protein or an Anc80 viral vector encoding a sphingolipid-metabolizing protein for use in the treatment of MI.

In one aspect, the disclosure relates to a method to prevent cell death and/or cell senescence and improve survival of a mammalian cell or group of cells in vitro or in vivo, the method comprising administering to the cell or group of cells an Anc80 vector selected from the group consisting of (1) an Anc80 vector that encodes a ceramidase (2) an Anc80 vector that encodes sphingosine kinase (SPHK), (3) an Anc80 vector that encodes sphingosine-1-phosphate receptor (S1PR), (4) an Anc80 vector that encodes a ceramide kinase, (CERK) and combinations of (1), (2), (3), and (4). In one embodiment, a single Anc80 vector is constructed to comprise a nucleic acid for more than one sphingolipid-metabolizing protein administration is by contacting said cell or group of cells with the vector, for example, by putting the vector into the cell culture medium. In another embodiment, administration is by introduction of the sphingolipid-metabolizing vector into the cell, group of cells or tissue/organ using techniques known to those of skill in the art.

For purposes of the present disclosure, cells are mammalian cells and may be selected from the group consisting of primary cells for example cardiac cells, hair cells of the ear, or photoreceptor cells of the eye.

In one aspect, the disclosure relates to a method to improve patient outcome following myocardial infarction (MI) comprising contacting cardiac cells or tissue with (1) an Anc80 that encodes ceramidase, (2) an ANC80 that encodes sphingosine kinase (SPHK), (3) an ANC80 that encodes sphingosine-1-phosphate receptor (S1PR) (4) an ANC80 that encodes a ceramide kinase (CERK), or any combination of (1), (2), (3) and (4).

In yet another related aspect, the disclosure relates to a composition comprising one or more ANC80s that encodes ceramidase, one or more Anc80s that encodes sphingosine kinase (SPHK), one or more Anc80s that encodes sphingosine-1-phosphate receptor (S1PR), and one or more Anc80s that encodes a ceramide kinase (CERK).

In one embodiment the Anc80 is a synthetic vector, Acn80 (see Zinn et al.), and contains a nucleotide sequence that encodes acid ceramidase that has the oligonucleotide sequence of SEQ ID NO: 1. In another embodiment, the Anc80 encoding AC has the oligonucleotide sequence of SEQ ID NO: 6. In another embodiment, the cells are contacted with an Anc80 that encodes sphingosine kinase (SPHK) having the oligonucleotide sequence of SEQ ID NO: 2. In another embodiment, the sphingolipid metabolizing molecule is S1PR and the oligonucleotide encoding it has the sequence SEQ ID NO: 3. In another embodiment, the sphingolipid metabolizing molecule is CERK and the oligonucleotide encoding it has the sequence SEQ ID NO: 19.

In one aspect, the present disclosure relates to a method to improve quality/survival of cells comprising contacting said cells with a (1) an Anc80 that encodes ceramidase, (2) an Anc80 that encodes sphingosine kinase (SPHK), (3) an Anc80 that encodes sphingosine-1-phosphate receptor (S1PR), an Anc80 that encodes CERK or any combination of (1), (2), (3) and (4).

In one aspect, the present disclosure relates to a method for treating a subject following a myocardial infarction (MI), the method comprising administering to the subject a therapeutically effective dose of an Anc80 viral vector encoding a sphingolipid-metabolizing protein. In one embodiment, the sphingolipid-metabolizing protein is selected from the group consisting of (1) a ceramidase; (2) sphingosine kinase (SPHK); (3) sphingosine-1-phosphate receptor (SIPR); (4) ceramidase kinase (CERK) or a combination of (1), (2), (3), and (4).

Compositions comprising any combination of ANC80s that encode (1) a ceramidase, (2) sphingosine kinase (SPHK), (3) sphingosine-1-phosphate receptor (S1PR) and a (4) CERK are encompassed by the present disclosure.

In yet another related aspect, the viral vector is an engineered gene therapy vector, Anc80 [described in Zinn et al. In *Silico Reconstruction of the Viral Evolutionary Lin-*

*eage Yields a Potent Gene Therapy Vector, Cell Reports* 12. 1056-1068 (2015), and U.S. Pat. No. 9,695,220; both references are hereby incorporated by reference].

BRIEF DESCRIPTION OF THE DRAWINGS

FIGS. 1A-1E show the characterization of cell death dynamics and sphingolipid-metabolizing enzymes expression in mouse heart after MI. Hearts were harvested from sham operated mice or 4 hours 1, 2, 4 and 28 days post MI. A) TUNEL stain was used to assess DNA fragmentation in cardiac cells in non-treated, 1, 2, 4 and 28 days post MI. Troponin-I immunostaining was used to distinguish between cardiomyocytes and non-cardiomyocytes. B) Dendogram of Sphingolipids signaling pathway transcriptome in sham hearts, 4 h and 24 h post ligation. C) Acid Ceramidase (AC), Sphk1 and S1PR2 mRNA levels relative to 18s rRNA was assessed in the left ventricle (LV) in early stages of MI development by quantitative PCR D) Protein levels of AC and Sphk1 were assessed in the LV at early stages of MI development by western-blot. E) AC activity in the LV after MI at early stages of MI development.

FIG. 8 shows EGFP expression 6 weeks after IM injection of $2.5 \times 10^{11}$ GC of Anc80 or AAV9 encoding EGFP. Adult rat hearts were injected intramyocardially (IM) with $2.5 \times 10^{11}$ GC of Anc80 (A) or AAV9 (B) encoding EGFP. The hearts were collected 6 weeks post injection and sectioned. Heart sections were imaged using a fluorescence scanner.

Figure 9:
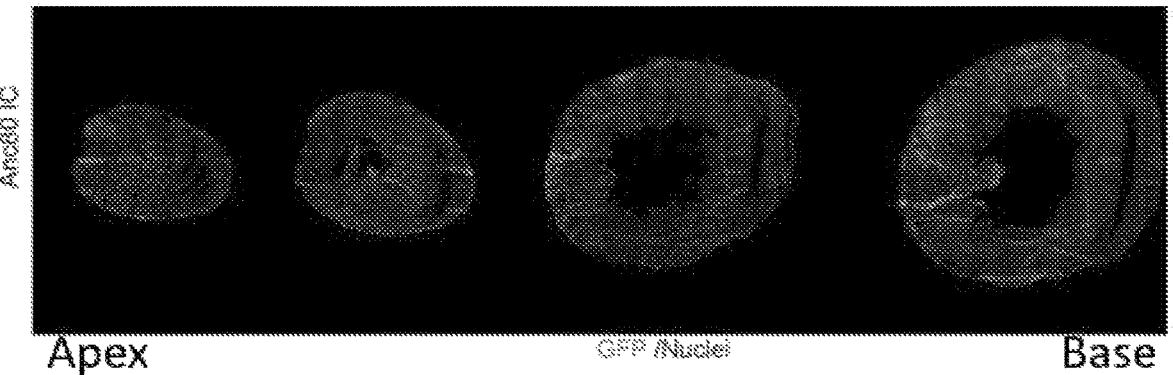

FIG. 9 shows EGFP expression 6 weeks after IC injection of $2.5 \times 10^{11}$ GC of Anc80 encoding EGFP. Adult rat heart was injected intracoronary (IC) with $2.5 \times 10^{11}$ GC of Anc80 encoding EGFP. The heart was collected 6 weeks post injection. Heart sections were imaged using a fluorescence scanner.

Figure 10:
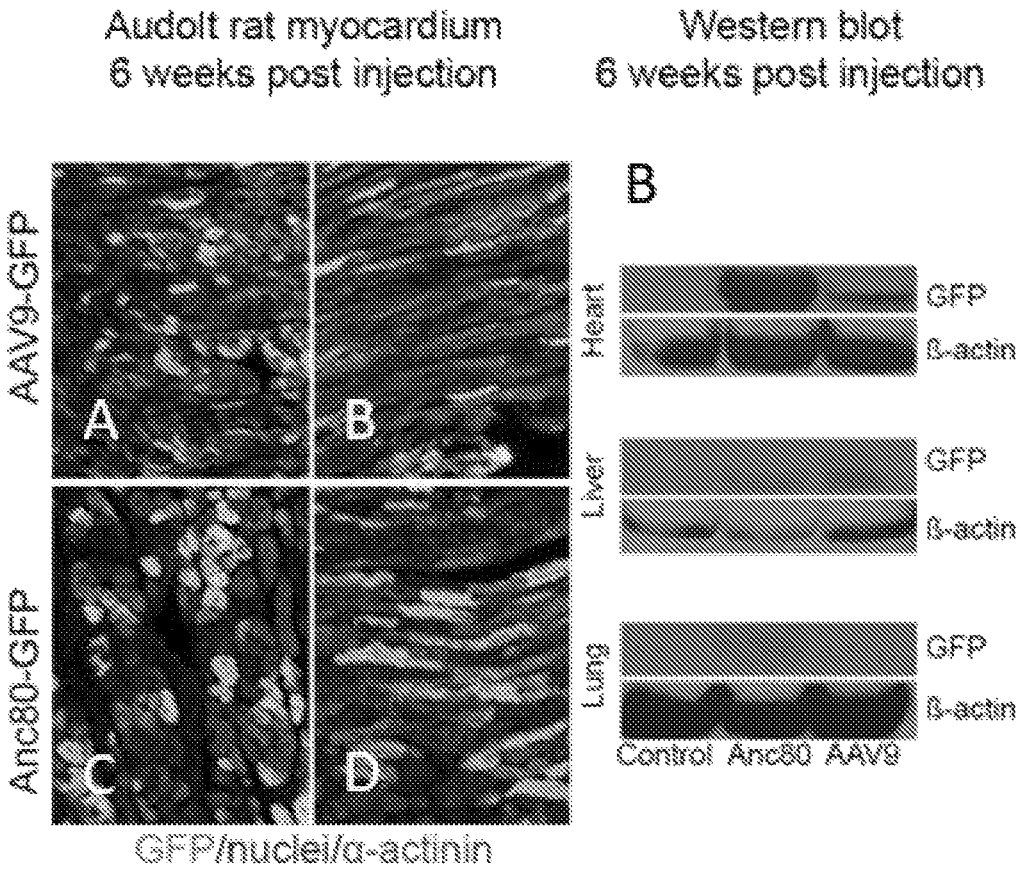

FIG. 10 shows EGFP biodistribution. Adult rat hearts were injected intramyocardially (IM) with $2.5 \times 10^{11}$ GC of AAV9 (A, B) or Anc80 (C, D) encoding EGFP. The hearts were collected 6 weeks post injection. Heart sections were immunostained with GFP antibody and a cardiomyocyte-specific marker, α-actinin antibody. (E) GFP expression in heart liver and lung was assessed using western blot analysis.

Figure 11:
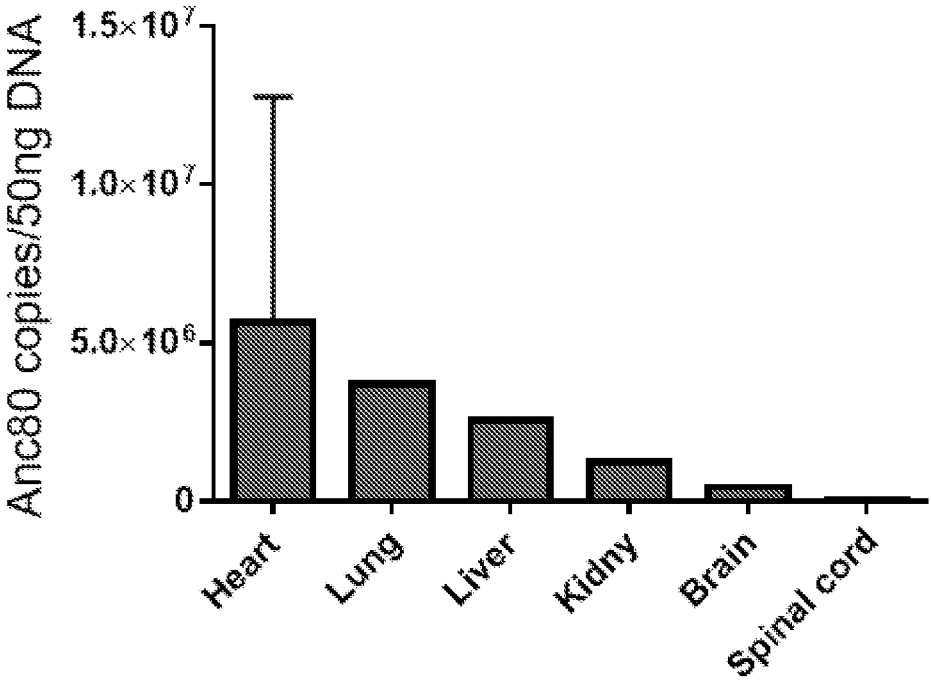

FIG. 11 shows Anc80 viral genome bio-distribution 8 weeks post IM injection. Adult rats hearts were injected intramyocardially (IM) with $7.5 \times 10^{10}$ GC of Anc80 encoding firefly luciferase. Viral genome copies in the heart, lung, liver, brain and spinal cord were assessed using qPCR using firefly luciferase specific primers.

Figure 12A:
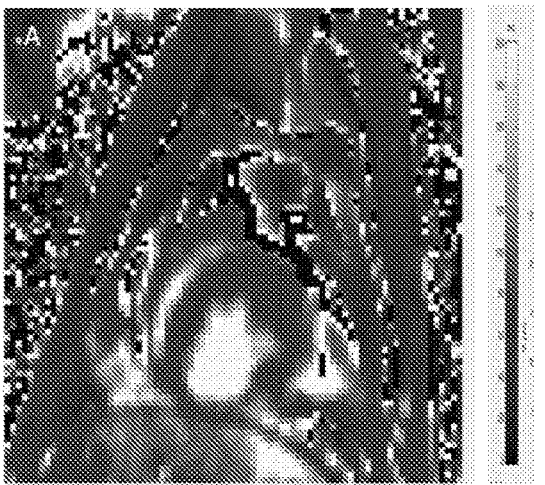
Figure 12B:
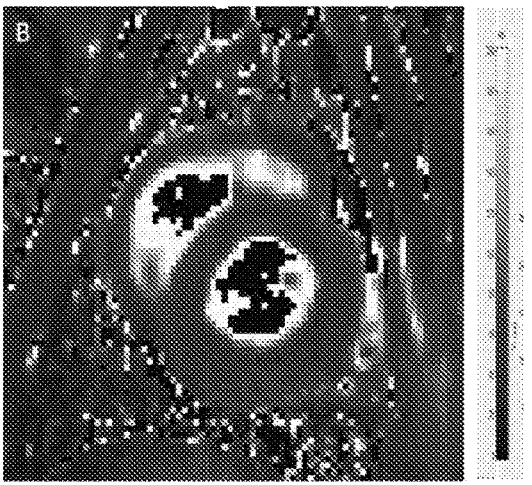

FIGS. 12A and 12B show results of a sheep model of myocardial infarction and gene delivery of AC by anc80 vector. T2 maps work by tracking signal of water molecules and granulocytes linked to inflammation. Higher hotter T2 times indicate inflammation. The AC animal in area of injection has purple normal T2 times in fully rescued myocardium which should be infarcted. Damage that accrued in the lower non injected slice can be seen. AC has effects on both viability and reducing inflammation from the infarction. (A) T2 MRI mapped image featuring inflammation response in the lower apex portion of the heart from a gene therapy treated animal. Higher T2 values indicate active damage and myocardium at risk, in this case 90-100 consistent with detectable infarction. (B) T2 MRI mapped image from an ovine subject overexpressing AC gene therapy at 4 weeks. Normal T2 times of 40-50 (purple) indicating robust healthy myocardium in the area of injections and surrounding myocardium.

Figures 13A, 13B:
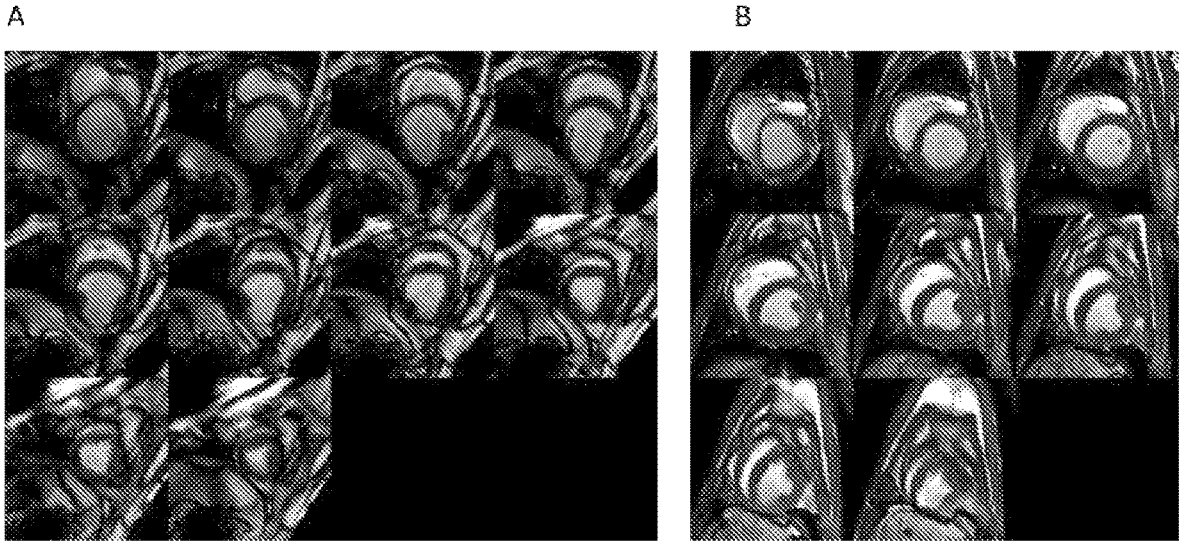

FIGS. 13A and 13B are a series of stills from a movie (A) showing a 3 month post infarction animal treated with AAV control or non-expression null vector. This figure shows that there is profound diskinesis and bulging in the middle to upper portions of the wall. Infarcted dead heart tissue bulges and does not contribute to the contraction. (B) The first AC animal demonstrated robust rescue of function from the effects of the MI. There is nice strong contraction profile all around the heart slices that were injected. In the lower non injected area bulging can be seen. As shown, this area is much less in terms of infarction size and impact on overall function. This animal had a score of 60% ejection fraction which is basically normal. At 4 weeks the animals usually drop to 45-53% range and by 3 months drop in the 35-40% range as in the control video. Ejection fraction is the main endpoint to assess function. Additionally, scar size from the MI was only 5% compared to controls in which scar size is usually in the range of 13-25%.

Figure 14:
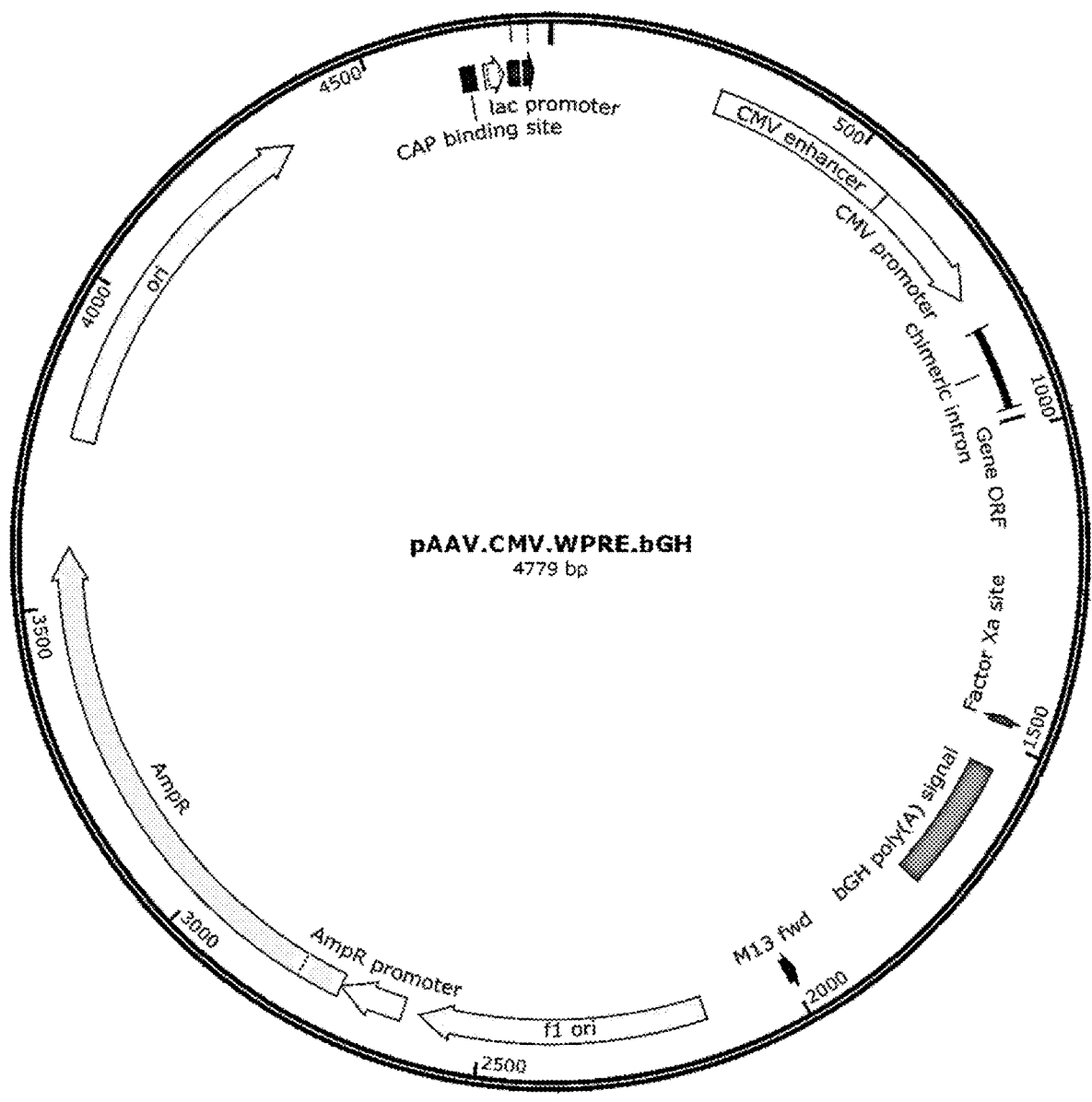

FIG. 14 is a map of an Anc80.AC vector used in the method of the disclosure.

Figure 15:
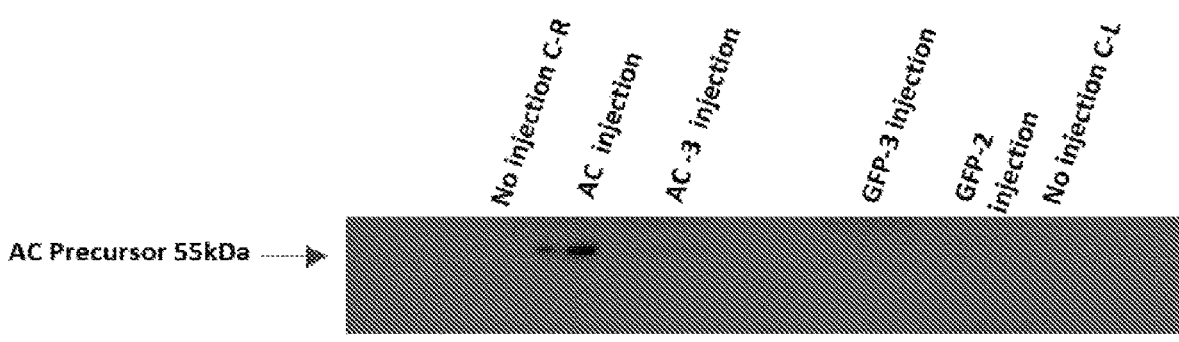

FIG. 15 shows western blot analysis of AC expression post AC CMV vector injection into mouse cochlear using AC H-41 antibody.

Figure 16:
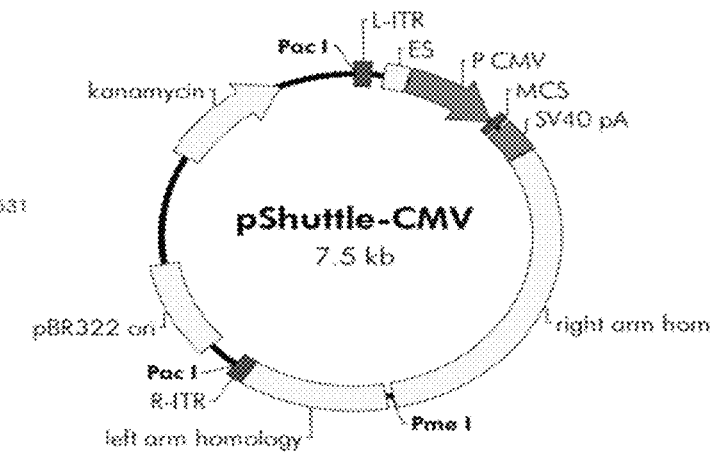

FIG. 16 shows the vector map of the AC CMV vector that was injected into mouse cochlear tissue.

6

DETAILED DESCRIPTION OF THE DISCLOSURE

All patents, published applications and other references cited herein are hereby incorporated by reference into the present application.

In the description that follows, certain conventions will be followed as regards the usage of terminology. In general, terms used herein are intended to be interpreted consistently with the meaning of those terms, as they are known to those of skill in the art. Some definitions are provided purely for the convenience of the reader.

The term "cell or group of cells" is intended to encompass single cells as well as multiple cells either in suspension or in monolayers. Whole tissues also constitute a group of cells.

The term "cell quality" or "quality of a cell" refers to the level of cell viability, and cellular function of a cell as measured against a normal healthy cell of the same type with normal cell function and expected life span, the quality of cells that are programmed for survival but not for cell death. Embryo quality is the ability of an embryo to perform successfully in terms of conferring a high pregnancy rate and/or resulting in a healthy offspring and is assessed mainly by microscopic evaluation at certain time points following in vitro fertilization. Embryo profiling is the estimation of embryo quality by qualification and/or quantification of various parameters known to those of skill in the art including but not limited to number of pronuclei, cell number, cell regularity, degree of fragmentation. Estimations of embryo quality guides the choice in embryo selection in in vitro fertilization.

The term "inhibit" or "inhibition" when used in conjunction with senescence includes the ability of the sphingolipid-metabolizing proteins of the disclosure to reverse senescence, thereby returning to normal or near normal function.

The terms "stress", "stress-related events" or "cellular-stress" refers to a wide range of molecular changes that cells undergo in response to environmental stressors, such as extreme temperatures, exposure to toxins, mechanical damage, anoxia, and noise.

The term "robustness" as it is used herein, refers to the quality or condition of being strong and in good condition with normal function.

The present technology is based on the use of sphingo-lipid metabolizing protein in order to manipulate the fate of cells post stress-related events and during aging. Different types of stress can initiate the signal transduction that leads to two major pathways: one can lead to cell death and the other leads to senescence, which is characterized by low cell function and arrested regeneration and amplification. In addition, senescent cells secrete different factors that can trigger the immune response and lead to inflammation and additional cell death. Cell senescence can be initiated not only by stress but also during aging. Both the cell death and cell senescence pathways involve sphingolipid metabolism mainly an increase in ceramide that can lead to both.

Ceramide has been shown to induce apoptotic cell death in different cells type including murine and human cardiomyocytes. On the other hand, sphingosine, one of the products of ceramide degradation can be phosphorylated to give rise to a major agent of cell survival and cardioprotection, sphingosine 1 phosphate.

There are several studies that support association of the signaling lipid, ceramide, and its metabolizing enzymes with cellular and organismal aging. It has been reported that the intracellular level of ceramide increased during stress related signaling such as cell culture and aging. Ceramidase, for example, acid ceramidase (AC) is required to hydrolyze ceramide into sphingosine and free fatty acids. Sphingosine is rapidly converted to sphingosine-1-phosphate (S1P), another important signaling lipid that counteracts the effects of ceramide and promotes cell survival. Thus, AC is a "rheostat" that regulates the levels of ceramide and S1P in cells, and as such participates in the complex and delicate balance between death and survival.

For example, we have previously shown that AC expression is carefully regulated during oocyte maturation and early embryo development (Eliyahu, et al, 2010). We have also found that the complete "knock-out" of AC function in mice leads to embryo death between the 2 and 8-cell stage (Eliyahu, FASEB J, 2007). In addition, our previous publication (Eliyahu, FASEB J, 2010) showed that the ceramide-metabolizing enzyme, AC is expressed and active in human cumulus cells and follicular fluid, essential components of this environment, and that the levels of this enzyme are positively correlated with the quality of human embryos formed in vitro. These observations led to a new approach for oocyte and embryo culture that markedly improves the outcome of in vitro fertilization (IVF).

In this disclosure, we describe a strategy different from previously described approaches to reduce ceramide levels in the ischemic heart. Instead of targeting ceramide synthesis, we study the effect of increasing ceramide hydrolysis by overexpression of acid ceramidase. With this strategy, not only can we reduce ceramide levels but we also increase the reservoir of sphingosine which is the main building block for the pro-survival molecule sphingosine-1-phosphate (S1P).

Choice of Vehicle and Duration of Expression Needed

Methods and compositions for in vivo delivery of acid ceramidase that express a sphingolipid-metabolizing protein such as ceramidase were explored. Each provides a different duration of ceramidase expression depending on the time that expression is needed given the particular situation. For example, use of the protein form is suitable if short term activity is required for up to 72 hours, mainly for in vitro applications, cell culture, cell therapy, or during primary or stem cell derivation. Use of the protein form is generally applicable to any cell type in vivo, including gametes. Moreover, dermatological applications, such as anti-aging treatments for the skin, lend themselves to use of the protein.

For applications where more sustained expression of a sphingolipid metabolizing enzyme is required, for example in a method for restoring cardiac function following a myocardial infarction, hearing and vision loss, orthopedic and neuronal injuries and the like, expression from an Anc80 vector may be desirable.

Adeno-associated viruses have emerged as one of the most promising vectors in the field of gene therapy. Preclinical and clinical studies have validated the use of adeno-associated viral vectors (AAVs) as a safe and efficient delivery vehicle for gene transfer. AAV vectors are known to be expressed for several months or longer post administration; thus, they provide a more extensive time frame than modRNA.

More recently, Zinn et al. identified Anc80 as a highly potent in vivo gene therapy vector for targeting liver, muscle and retina. Anc80 virus, an in silico designed gene therapy vector, has demonstrated high gene expression levels in the liver, eye and ear compared to naturally occurring adeno-associated viral vectors (AAVs) that are currently in clinical development. Due to its synthetic nature, Anc80 does not circulate in humans, making it less likely to be recognized immunologically by antibodies against naturally-occurring AAVs. Anc80 also provides longer lasting expression. In addition, Anc80 expresses protein in much higher amounts than AAVs, so the amount of necessary virus is much less that leads to lower immune response.

The present disclosure, therefore, also provides a method for inhibiting or reducing damage to cardiac cells following MI by administration of a cocktail of Anc80 virus encoding sphingolipid metabolizing proteins. The treatment includes different combinations of Acid Ceramidase (AC) and/or Sphingosine Kinase (SPHK) and/or Sphingosine-1-phosphate receptor (S1PR) gene (cDNA). Anc80 virus, an in silico designed gene therapy vector, Anc80 has demonstrated high gene expression levels in the liver, eye and ear compared to naturally-occurring adeno-associated viral vectors (AAVs) that are currently in clinical development. Anc80, an engineered gene therapy vector, is synthetic in nature and has been shown to reduce cross-reactivity with commonly used AAV vectors. Anc80 is a potent gene therapy vector that is not known to circulate in humans, making it less likely to cross-react immunologically with naturally occurring AAVs.

Sphingolipid-Metabolizing Proteins

In one embodiment, a composition useful for practicing the method of the present disclosure may include either individually or in different combinations Anc80 vectors encoding the following sphingolipid-metabolizing proteins: ceramidase (acid, neutral or alkaline), sphingosine kinase (SPHK), sphingosine-1-phosphate receptor (S1PR), and a ceramide kinase (CERK). In one embodiment, the sphingolipid-metabolizing protein is a ceramidase.

Ceramidase is an enzyme that cleaves fatty acids from ceramide, producing sphingosine (SPH), which in turn is phosphorylated by a sphingosine kinase to form sphingosine-1-phosphate (S1P). Ceramidase is the only enzyme that can regulate ceramide hydrolysis to prevent cell death and SHPK is the only enzyme that can synthesize sphingosine 1 phosphate (S1P) from sphingosine (the ceramide hydrolysis product) to initiate cell survival. S1PR, a G protein-coupled receptor binds the lipid-signaling molecule S1P to induce cell proliferation, survival, and transcriptional activation. CERK is an phosphatase that phosphorylates ceramide into ceramide 1 phosphate to induce cell survival.

Presently, 7 human ceramidases encoded by 7 distinct genes have been cloned:

acid ceramidase (ASAH1)—associated with cell survival;

neutral ceramidase (ASAH2, ASAH2B, ASAH2C)—protective against inflammatory cytokines;

alkaline ceramidase 1 (ACER1)—mediating cell differentiation by controlling the generation of SPH and S1P;

alkaline ceramidase 2 (ACER2)—important for cell proliferation and survival; and alkaline ceramidase 3 (ACER3).

The nucleotide sequences for nucleic acids encoding these ceramidases are shown in Table 1.

In one embodiment, Anc80, a relatively nascent technology, has shown considerable potential as a delivery vehicle for gene therapy in disease, for example, cardiac disease, hearing loss, vision loss and neurodegenerative diseases. Anc80 as an engineered gene therapy vector is synthetic in nature and is not known to circulate in humans. It has been shown to have reduced cross-reactivity with commonly used AAV vectors. Anc80 therefore is a potent gene therapy vector, which is less likely to be recognized immunologically by antibodies against naturally occurring AAVs.

An Anc80 vector encoding acid ceramidase (Anc80.AC) has multiple advantages over other potential anti-apoptotic factors.

Low Toxicity

Physiological enzymes are expected to have no toxic effects. The AC protein is present as two forms (active and inactive) in the cell. The inactive AC protein undergoes an auto-self cleavage to the active form, which is responsible for hydrolyzing ceramide to sphingosine after exposure to stress. Transfecting cells with Anc80.AC increases mostly the inactive precursor of the enzyme; this allows physiological control to regulate the amount of active AC protein required for survival. AC should not influence other cellular signaling because the only known biological function of AC is the control of ceramide metabolism. The creation of a mouse model in which the AC enzyme (COEAC) is constantly overexpressed in all tissues demonstrates a lack of toxicity as the result of AC overexpression.

Unique Physiological Function of Acid Ceramidase

Increase in ceramide level can have different outcomes leading to cell death and/or senescence. Ceramidase is the only enzyme that can hydrolyze ceramide and hydrolysis of ceramide is its putative function.

Table 1 contains the nucleotide sequences to be encoded by the vectors disclosed for use in practicing the method.

TABLE 1

| Gene | Open Reading Frame |
|------|--------------------|
| ASAH1 transcript variant 1 (ACv1) | ATGCCGGGCCGGAGTTGCGTCGCCTTAGTCCTCCTGGCTGCCGCCGTCAGCTGTGCCGTCGCGCA<br>GCACGCGCCGCCGTGGACAGAGGACTGCAGAAAATCAACCTATCCTCCTTCAGGACCAACGTAC<br>AGAGGTGCAGTTCCATGGTACACCATAAATCTTGACTTACCACCCTACAAAAGATGGCATGAATT<br>GATGCTTGACAAGGCACCAGTGCTAAAGGTTATAGTGAATTCTCTGAAGAATATGATAAATACAT<br>TCGTGCCAAGTGGAAAAATTATGCAGGTGGTGGATGAAAAATTGCCTGGCCTACTTGGCAACTTT<br>CCTGGCCCTTTTGAAGAGGAAATGAAGGGTATTGCCGCTGTTACTGATATACCTTTAGGAGAGAT<br>TATTTCATTCAATATTTTTTATGAATTATTTTACCATTTGTACTTCAATAGTAGCAGAAGACAAAAA<br>GGTCATCTAATACATGGGAGAAACATGGATTTTGGAGTATTTCTTGGGTGGAACATAAATAATGA<br>TACCTGGGTCATAACTGAGCAACTAAAACCTTTAACAGTGAATTTGGATTTCCAAAGAAACAACA<br>AAACTGTCTTCAAGGCTTCAAGCTTTGCTGGCTATGTGGGCATGTTAACAGGATTCAAACCAGGA<br>CTGTTCAGTCTTACACTGAATGAACGTTTCAGTATAAATGGTGGTTATCTGGGTATTCTAGAATGG<br>ATTCTGGGAAAGAAAGATGTCATGTGGATAGGGTTCCTCACTAGAACAGTTCTGGAAAATAGCA<br>CAAGTTATGAAGAAGCCAAGAATTTATTGACCAAGACCAAGATATTGGCCCCAGCCTACTTTATC<br>CTGGGAGGCAACCAGTCTGGGGAAGGTTGTGTGATTACACGAGACGAAAGGAATCATTGGAT<br>GTATATGAACTCGATGCTAAGCAGGGTAGATGGTATGTGGTACAAACAAATTATGACCGTTGGA<br>AACATCCCTTCTTCCTTGATGATCGCAGAACGCCTGCAAAGATGTGTCTGAACCGCACCAGCCAA<br>GAGAATATCTCATTTGAAACCATGTATGATGTCCTGTCAACAAAACCTGTCCTCAACAAGCTGACC<br>GTATACACAACCTTGATAGATGTTACCAAAGGTCAATTCGAAACTTACCTGCGGGACTGCCCTGA<br>CCCTTGTATAGGTTGGTGA (SEQ ID NO: 1) |
| Sphk1 | ATGGATCCAGTGGTCGGTTGCGGACGTGGCCTCTTTGGTTTTGTTTTCTCAGCGGGCGGCCCCCG<br>GGGCGTGCTCCCGCGGCCCTGCCGCGTGCTGGTGCTGCTGAACCCGCGCGGCGGCAAGGGCAA<br>GGCCTTGCAGCTCTTCCGGAGTCACGTGCAGCCCCTTTTGGCTGAGGCTGAAATCTCCTTCACGCT<br>GATGCTCACTGAGCGGCGGAACCACGCGCGGGAGCTGGTGCGGTCGGAGGAGCTGGGCCGCTG<br>GGACGCTCTGGTGGTCATGTCTGGAGACGGGCTGATGCACGAGGTGGTGAACGGGCTCATGGA<br>GCGGCCTGACTGGGAGACCGCCATCCAGAAGCCCCTGTGTAGCCTCCCAGCAGGCTCTGGCAAC<br>GCGCTGGCAGCTTCCTTGAACCATTATGCTGGCTATGAGCAGGTCACCAATGAAGACCTCCTGAC<br>CAACTGCACGCTATTGCTGTGCCGCCGGCTGCTGTCACCCATGAACCTGCTGTCTCTGCACACGGC<br>TTCGGGGCTGCGCCTCTTCTCTGTGCTCAGCCTGGCCTGGGGCTTCATTGCTGATGTGGACCTAG<br>AGAGTGAGAAGTATCGGCGTCTGGGGGAGATGCGCTTCACTCTGGGCACCTTCCTGCGTCTGGC<br>AGCCCTGCGCACCTACCGCGGCCGACTGGCCTACCTCCCTGTAGGAAGAGTGGGTTCCAAGACAC<br>CTGCCTCCCCCGTTGTGGTCCAGCAGGGCCCGGTAGATGCACACCTTGTGCCACTGGAGGAGCCA<br>GTGCCCTCTCACTGGACAGTGGTGCCCGACGAGGACTTTGTGCTAGTCCTGGCACTGCTGCACTC<br>GCACCTGGGCAGTGAGATGTTTGCTGCACCCATGGGCCGCTGTGCAGCTGGCGTCATGCATCTGT<br>TCTACGTGCGGGCGGGAGTGTCTCGTGCCATGCTGCTGCGCCTCTTCCTGGCCATGGAGAAGGG<br>CAGGCATATGGAGTATGAATGCCCCTACTTGGTATATGTGCCCGTGGTCGCCTTCCGCTTGGAGC<br>CCAAGGATGGGAAAGGTGTGTTTGCAGTGGATGGGGAATTGATGGTTAGCGAGGCCGTGCAGG<br>GCCAGGTGCACCCAAACTACTTCTGGATGGTCAGCGGTTGCGTGGAGCCCCCGCCCAGCTGGAA<br>GCCCCAGCAGATGCCACCGCCAGAAGAGCCCTTATGA (SEQ ID NO: 2) |
| S1PR2 | ATGGGCAGCTTGTACTCGGAGTACCTGAACCCCAACAAGGTCCAGGAACACTATAATTATACCAA<br>GGAGACGCTGGAAACGCAGGAGACGACCTCCCGCCAGGTGGCCTCGGCCTTCATCGTCATCCTCT<br>GTTGCGCCATTGTGGTGGAAAACCTTCTGGTGCTCATTGCGGTGGCCCGAAACAGCAAGTTCCAC<br>TCGGCAATGTACCTGTTTCTGGGCAACCTGGCCGCCTCCGATCTACTGGCAGGCGTGGCCTTCGT<br>AGCCAATACCTTGCTCTCTGGCTCTGTCACGCTGAGGCTGACGCCTGTGCAGTGGTTGCCCGGG<br>AGGGCTCTGCCTTCATCACGCTCTCGGCCTCTGTCTTCAGCCTCCTGGCCATCGCCATTGAGCGCC<br>ACGTGGCCATTGCCAAGGTCAAGCTGTATGGCAGCGACAAGAGCTGCCGCATGCTTCTGCTCATC<br>GGGGCCTCGTGGCTCATCTCGCTTGGTCCTCGGTGGCCTGCCCATCCTTGGCTGGAACTGCCTGGG<br>CCACCTCGAGGCCTGCTCCACTGTCCTGCCTCTCTACGCCAAGCATTATGTGCTGTGCGTGGTGAC<br>CATCTTCTCCATCATCCTGTTGGCCATCGTGGCCCTGTACGTGCGCATCTACTGCGTGGTCCGCTC<br>AAGCCACGCTGACATGGCCGCCCCGCAGACGCTAGCCCTGCTCAAGACGGTCACCATCGTGCTAG<br>GCGTCTTTATCGTCTGCTGGCTGCCCGCCTTCAGCATCCTCCTTCTGGACTATGCCTGTCCCGTCCA<br>CTCCTGCCCGATCCTCTACAAAGCCCACTACTTTTTCGCCGTCTCCACCCTGAATTCCCTGCTCAAC<br>CCCGTCATCTACACGTGGCGCAGCCGGGACCTGCGGCGGGAGGTGCTTCGGCCGCTGCAGTGCT<br>GGAGGCCGGGGGTGGGGGTGCAAGGACGGAGGCGGGGGGGGGACCCCGGGCCACCACCTCCTG<br>CCACTCCGCAGCTCCAGCTCCCTGGAGAGGGGCATGCACATGCCCACGTCACCCACGTTTCTGGA<br>GGGCAACACGGTGGTCATG (SEQ ID NO: 3) |
| Firefly luciferase | ATGGCCGATGCTAAGAACATTAAGAAGGGCCCTGCTCCCTTCTACCCTCTGGAGGATGGCACCGC<br>TGGCGAGCAGCTGCACAAGGCCATGAAGAGGTATGCCCTGGTGCCTGGCACCATTGCCTTCACC<br>GATGCCCACATTGAGGTGGACATCACCTATGCCGAGTACTTCGAGATGTCTGTGCGCCTGGCCGA<br>GGCCATGAAGAGGTACGGCCTGAACACCAACCACCGCATCGTGGTGTGCTCTGAGAACTCTCTGC<br>AGTTCTTCATGCCAGTGCTGGGCGCCCTGTTCATCGGAGTGGCCGTGGCCCCTGCTAACGACATT |

TABLE 1-continued

| Gene | Open Reading Frame |
|------|--------------------|
| | TACAACGAGCGCGAGCTGCTGAACAGCATGGGCATTTCTCAGCCTACCGTGGTGTTCGTGTCTAA<br>GAAGGGCCTGCAGAAGATCCTGAACGTGCAGAAGAAGCTGCCTATCATCCAGAAGATCATCATC<br>ATGGACTCTAAGACCGACTACCAGGGCTTCCAGAGCATGTACACATTCGTGACATCTCATCTGCCT<br>CCTGGCTTCAACGAGTACGACTTCGTGCCAGAGTCTTTCGACAGGGACAAAACCATTGCCCTGAT<br>CATGAACAGCTCTGGGTCTACCGGCCTGCCTAAGGGCGTGGCCCTGCCTCATCGCACCGCCTGTG<br>TGCGCTTCTCTCACGCCCGCGACCCTATTTTCGGCAACCAGATCATCCCCGACACCGCTATTCTGA<br>GCGTGGTGCCATTCCACCACGGCTTCGGCATGTTCACCACCCTGGGCTACCTGATTTGCGGCTTTC<br>GGGTGGTGCTGATGTACCGCTTCGAGGAGGAGCTGTTCCTGCGCAGCCTGCAAGACTACAAAAT<br>TCAGTCTGCCCTGCTGGTGCCAACCCTGTTCAGCTTCTTCGCTAAGAGCACCCTGATCGACAAGTA<br>CGACCTGTCTAACCTGCACGAGATTGCCTCTGGCGGCGCCCCACTGTCTAAGGAGGTGGGCGAA<br>GCCGTGGCCAAGCGCTTTCATCTGCCAGGCATCCGCCAGGGCTACGGCCTGACCGAGACAACCA<br>GCGCCATTCTGATTACCCCAGAGGGCGACGACAAGCCTGGCGCCGTGGGCAAGGTGGTGCCATT<br>CTTCGAGGCCAAGGTGGTGGACCTGGACACCGGCAAGACCCTGGGAGTGAACCAGCGCGGCGA<br>GCTGTGTGTGCGCGGCCCTATGATTATGTCCGGCTACGTGAATAACCCTGAGGCCACAAACGCCC<br>TGATCGACAAGGACGGCTGGCTGCACTCTGGCGACATTGCCTACTGGGACGAGGACGAGCACTT<br>CTTCATCGTGGACCGCCTGAAGTCTCTGATCAAGTACAAGGGCTACCAGGTGGCCCCAGCCGAGC<br>TGGAGTCTATCCTGCTGCAGCACCCTAACATTTTCGACGCCGGAGTGGCCGGCCTGCCCGACGAC<br>GATGCCGGCGAGCTGCCTGCCGCCGTCGTCGTGCTGGAACACGGCAAGACCATGACCGAGAAG<br>GAGATCGTGGACTATGTGGCCAGCCAGGTGACAACCGCCAAGAGCTGCGCGGCGGAGTGGTG<br>TTCGTGGACGAGGTGCCCAAGGGCCTGACCGGCAAGCTGGACGCCCGCAAGATCCGCGAGATCC<br>TGATCAAGGCTAAGAAAGGCGGCAAGATCGCCGTGTAA (SEQ ID NO: 4) |
| nGFP | ATGGTGAGCAAGGGCGAGGAGCTGTTCACCGGGGTGGTGCCCATCCTGGTCGAGCTGGACGGC<br>GACGTAAACGGCCACAAGTTCAGCGTGTCCGGCGAGGGCGAGGGCGATGCCACCTACGGCAAG<br>CTGACCCTGAAGTTCATCTGCACCACCGGCAAGCTGCCCGTGCCCTGGCCCACCCTCGTGACCACC<br>CTGACCTACGGCGTGCAGTGCTTCAGCCGCTACCCCGACCACATGAAGCAGCACGACTTCTTCAA<br>GTCCGCCATGCCCGAAGGCTACGTCCAGGAGCGCACCATCTTCTTCAAGGACGACGGCAACTACA<br>AGACCCGCGCCGAGGTGAAGTTCGAGGGCGACACCCTGGTGAACCGCATCGAGCTGAAGGGCA<br>TCGACTTCAAGGAGGACGGCAACATCCTGGGGCACAAGCTGGAGTACAACTACAACAGCCACAA<br>CGTCTATATCATGGCCGACAAGCAGAAGAACGGCATCAAGGTGAACTTCAAGATCCGCCACAAC<br>ATCGAGGACGGCAGCGTGCAGCTCGCCGACCACTACCAGCAGAACACCCCCATCGGCGACGGCC<br>CCGTGCTGCTGCCCGACAACCACTACCTGAGCACCCAGTCCGCCCTGAGCAAAGACCCCAACGAG<br>AAGCGCGATCACATGGTCCTGCTGGAGTTCGTGACCGCCGCCGGGATCACTCTCGGCATGGACG<br>AGCTGTACAAGGGAGATCCAAAAAAGAAGAGAAAGGTAGGCGATCCAAAAAAGAAGAGAAAG<br>GTAGGTGATCCAAAAAAGAAGAGAAAGGTATAA (SEQ ID NO: 5) |
| ASAH2<br>transcript<br>variant 2<br>(ACv2) | ATGAACTGCTGCATCGGGCTGGGAGAGAAAGCTCGCGGGTCCCACCGGGCCTCCTACCCAAGTC<br>TCAGCGCGCTTTTCACCGAGGCCTCAATTCTGGGATTTGGCAGCTTTGCTGTGAAAGCCCAATGG<br>ACAGAGGACTGCAGAAAATCAACCTATCCTCCTTCAGGACCAACGTACAGAGGTGCAGTTCCATG<br>GTACACCATAAATCTTGACTTACCACCCTACAAAAGATGGCATGAATTGATGCTTGACAAGGCAC<br>CAGTGCTAAAGGTTATAGTGAATTCTCTGAAGAATATGATAAATACATTCGTGCCAAGTGGAAAA<br>ATTATGCAGGTGGTGGATGAAAAATTGCCTGGCCTACTTGGCAACTTTCCTGGCCCTTTTGAAGA<br>GGGAAATGAAGGGTATTGCCGCTGTTACTGATATACCCTTTAGGAGAGATTATTTCATTCAATATTTT<br>TTATGAATTATTTTACCATTTGTACTTCAATAGTAGCAGAAGACAAAAAAGGTCATCTAATACATGGG<br>GAGAAACATGGATTTTGGAGTATTTCTTGGGTGGAACATAAATAATGATACCTGGGTCATAACTG<br>AGCAACTAAAACCTTTAACAGTGAATTTGGATTTCCAAAGAAACAACAAAACTGTCTTCAAGGCTT<br>CAAGCTTTGCTGGCTATGTGGGCATGTTAACAGGATTCAAACCAGGACTGTTCAGTCTTACACTG<br>AATGAACGTTTCAGTATAAATGGTGGTTATCTGGGTATTCTAGAATGGATTCTGGGAAAGAAAGA<br>TGTCATGTGGATAGGGTTCCTCACTAGAACAGTTCTGGAAAATAGCACAAGTTATGAAGAAGCCA<br>AGAATTTATTGACCAAGACCAAGATATTGGCCCCAGCCTACTTTATCCTGGGAGGCAACCAGTCT<br>GGGGAAGGTTGTGTGATTACACGAGACAGAAAGGAATCATTGGATGTATATGAACTCGATGCTA<br>AGCAGGGTAGATGGTATGTGGTACAAACAAATTATGACCGTTGGAAACATCCCTTCTTCCTTGAT<br>GATCGCAGAACGCCTGCAAAGATGTGTCTGAACCGCACCAGCCAAGAGAATATCTCATTTGAAAC<br>CATGTATGATGTCCTGTCAACAAAACCTGTCCTCAACAAGCTGACCGTATACACAACCTTGATAGA<br>TGTTACCAAAGGTCAATTCGAAACTTACCTGCGGGACTGCCCTGACCCTTGTATAGGTTGGTGA<br>(SEQ ID NO: 6) |
| ASAH1<br>transcript<br>variant 3 | ATGAACTGCTGCATCGGGCTGGGAGAGAAAGCTCGCGGGTCCCACCGGGCCTCCTACCCAAGTC<br>TCAGCGCGCTTTTCACCGAGGCCTCAATTCTGGGATTTGGCAGCTTTGCTGTGAAAGCCCAATGG<br>ACAGAGGACTGCAGAAAATCAACCTATCCTCCTTCAGGACCAACTGTCTTCCCTGCTGTTATAAGG<br>TACAGAGGTGCAGTTCCATGGTACACCATAAATCTTGACTTACCACCCTACAAAAGATGGCATGA<br>ATTGATGCTTGACAAGGCACCAGTGCCTGGCCTACTTGGCAACTTTCCTGGCCCTTTTGAAGAGG<br>AAATGAAGGGTATTGCCGCTGTTACTGATATACCCTTTAGGAGAGATTATTTCATTCAATATTTTTT<br>ATGAATTATTTTACCATTTGTACTTCAATAGTAGCAGAAGACAAAAAAGGTCATCTAATACATGGG<br>AGAAACATGGATTTTGGAGTATTCTTGGGTGGAACATAAATAATGATACCTGGGTCATAACTGA<br>GCAACTAAAACCTTTAACAGTGAATTTGGATTTCCAAAGAAACAACAAAACTGTCTTCAAGGCTTC<br>AAGCTTTGCTGGCTATGTGGGCATGTTAACAGGATTCAAACCAGGACTGTTCAGTCTTACACTGA<br>ATGAACGTTTCAGTATAAATGGTGGTTATCTGGGTATTCTAGAATGGATTCTGGGAAAGAAAGAT<br>GTCATGTGGATAGGGTTCCTCACTAGAACAGTTCTGGAAAATAGCACAAGTTATGAAGAAGCCA<br>AGAATTTATTGACCAAGACCAAGATATTGGCCCCAGCCTACTTTATCCTGGGAGGCAACCAGTCT<br>GGGGAAGGTTGTGTGATTACACGAGACAGAAAGGAATCATTGGATGTATATGAACTCGATGCTA<br>AGCAGGGTAGATGGTATGTGGTACAAACAAATTATGACCGTTGGAAACATCCCTTCTTCCTTGAT<br>GATCGCAGAACGCCTGCAAAGATGTGTCTGAACCGCACCAGCCAAGAGAATATCTCATTTGAAAC<br>CATGTATGATGTCCTGTCAACAAAACCTGTCCTCAACAAGCTGACCGTATACACAACCTTGATAGA<br>TGTTACCAAAGGTCAATTCGAAACTTACCTGCGGGACTGCCCTGACCCTTGTATAGGTTGGTGA<br>(SEQ ID NO: 7) |

TABLE 1-continued

| Gene | Open Reading Frame |
|------|--------------------|

ASAH2 transcript variant 1

```
ATGGCCAAACGCACCTTCTCTAACTTGGAGACATTCCTGATTTTCCTCCTTGTAATGATGAGTGCC
ATCACAGTGGCCCTTCTCAGCCTCTTGTTTATCACCAGTGGGACCATTGAAAACCACAAAGATTTA
GGAGGCCATTTTTTTTCAACCACCCAAAGCCCTCCAGCCACCCAGGGCTCCACAGCTGCCCAACGC
TCCACAGCCACCCAGCATTCCACAGCCACCCAGAGCTCCACAGCCACTCAAACTTCTCCAGTGCCT
TTAACCCCAGAGTCTCCTCTATTTCAGAACTTCAGTGGCTAACCATATTGGTGTTGGACGAGCTGAC
TGCACAGGACAAGTAGCAGATATCAATTTGATGGGCTATGGCAAATCCGGCCAGAATGCACAGG
GCATCCTCACCAGGCTATACAGTCGTGCCTTCATCATGGCAGAACCTGATGGGTCCAATCGAACA
GTGTTTGTCAGCATCGACATAGGCATGGTATCACAAAGGCTCAGGCTGGAGGTCCTGAACAGAC
TGCAGAGTAAATATGGCTCCCTGTACAGAAGAGATAATGTCATCCTGAGTGGCACTCACACTCAT
TCAGGTCCTGCAGGATATTTCCAGTATACCGTGTTTGTAATTGCCAGTGAAGGATTTAGCAATCAA
ACTTTTCAGCACATGGTCACTGGTATCTTGAAGAGCATTGACATAGCACACACAAATATGAAACC
AGGCAAAATCTTCATCAATAAAGGAAATGTGGATGGTGTGCAGATCAACAGAAGTCCGTATTCTT
ACCTTCAAAATCCGCAGTCAGAGAGAGCAAGGTATTCTTCAAATACAGACAAGGAAATGATAGTT
TTGAAAATGGTAGATTTGAATGGAGATGACTTGGGCCTTATCAGCTGGTTTGCCATCCACCCGGT
CAGCATGAACAACAGTAACCATCTTGTAAACAGTGACAATGTGGGCTATGCATCTTACCTGCTTG
AGCAAGAGAAGAACAAAGGATATCTACCTGGACAGGGGCCATTTGTAGCAGCCTTTGCTTCATCA
AACCTAGGAGATGTGTCCCCCAACATTCTTGGACCACGTTGCATCAACACAGGAGAGTCCTGTGA
TAACGCCAATAGCACTTGTCCCATTGGTGGGCCTAGCATGTGCATTGCATTGTAAGGGACCTGGACAGG
ATATGTTTGACAGCACACAAATTATAGGACGGGCCATGTATCAGAGAGCAAAGGAACTCTATGCC
TCTGCCTCCCAGGAGGTAACAGGACCACTGGCTTCAGCACACCAGTGGGTGGATATGACAGATG
TGACTGTCTGGCTCAATTCCACACATGCATCAAAAACATGTAAACCAGCATTGGGCTACAGTTTTG
CAGCTGGCACTATTGATGGAGTTGGAGGCCTCAATTTTACACAGGGGAAAACAGAAGGGGATCC
ATTTTGGGACACCATTCGGGACCAGATCCTGGGAAAGCCATCTGAAGAAATTAAAGAATGTCATA
AACCCAAAGCCCATCCTTCTTCACACCGGAGAACTATCAAAACCTCACCCCTGGCATCCAGACATTG
TTGATGTTCAGATTATTACCCTTGGGTCCTTGGCCATAACTGCCATCCCCGGGGAGTTTACGACCA
TGTCTGGACGAAGACTTCGAGAGGCAGTTCAAGCAGAATTTGCATCTCATGGGATGCAGAACAT
GACTGTTGTTATTTCAGGTCTATGCAACGTCTATACACATTACATTACCACTTATGAAGAATACCA
GGCTCAGCGATATGAGGCAGCATCGACAATTTATGGACCGCACACATTATCTGCTTACATTCAGC
TCTTCAGAAACCTTGCTAAGGCTATTGCTACGGACACGGTAGCCAACCTGAGCAGAGGTCCAGAA
CCTCCCTTTTTCAAACAATTAATAGTTCCATTAATTCCTAGTATTGTGGATAGAGCACCAAAAGGC
AGAACTTTCGGGGATGTCCTGCAGCCAGCAAAACCTGAATACAGAGTGGGGGAAGTTGCTGAAG
TTATATTTGTAGGTGCTAACCCGAAGAATTCAGTACAAACCAGACCCATCAGACCTTCCTCACTG
TGGAGAAATATGAGGCTACTTCAACATCGTGGCAGATAGTGTGTAATGATGCCTCCTGGGAGACT
CGTTTTTATTGGCACAAGGGACTCCTGGGTCTGAGTAATGCAACAGTGGAATGGCATATTCCAGA
CACTGCCCAGCCTGGAATCTACAGAATAAGATATTTTGGACACAATCGGAAGCAGGACATTCTGA
AGCCTGCTGTCATACTTTCATTTGAAGGCACTTCCCCGGCTTTTGAAGTTGTAACTATTTAGTGA
(SEQ ID NO: 8)
```

ASAH2 transcript variant 2

```
ATGGCCAAACGCACCTTCTCTAACTTGGAGACATTCCTGATTTTCCTCCTTGTAATGATGAGTGCC
ATCACAGTGGCCCTTCTCAGCCTCTTGTTTATCACCAGTGGGACCATTGAAAACCACAAAGATTTA
GGAGGCCATTTTTTTTCAACCACCCAAAGCCCTCCAGCCACCCAGGGCTCCACAGCTGCCCAACGC
TCCACAGCCACCCAGCATTCCACAGCCACCCAGAGCTCCACAGCCACTCAAACTTCTCCAGTGCCT
TTAACCCCAGAGTCTCCTCTATTTCAGAACTTCAGTGGCTAACCATATTGGTGTTGGACGAGCTGAC
TGCACAGGACAAGTAGCAGATATCAATTTGATGGGCTATGGCAAATCCGGCCAGAATGCACAGG
GCATCCTCACCAGGCTATACAGTCGTGCCTTCATCATGGCAGAACCTGATGGGTCCAATCGAACA
GTGTTTGTCAGCATCGACATAGGCATGGTATCACAAAGGCTCAGGCTGGAGGTCCTGAACAGAC
TGCAGAGTAAATATGGCTCCCTGTACAGAAGAGATAATGTCATCCTGAGTGGCACTCACACTCAT
TCAGGTCCTGCAGGATATTTCCAGTATACCGTGTTTGTAATTGCCAGTGAAGGATTTAGCAATCAA
ACTTTTCAGCACATGGTCACTGGTATCTTGAAGAGCATTGACATAGCACACACAAATATGAAACC
AGGCAAAATCTTCATCAATAAAGGAAATGTGGATGGTGTGCAGATCAACAGAAGTCCGTATTCTT
ACCTTCAAAATCCGCAGTCAGAGAGAGCAAGGTATTCTTCAAATACAGACAAGGAAATGATAGTT
TTGAAAATGGTAGATTTGAATGGAGATGACTTGGGCCTTATCAGCTGGTTTGCCATCCACCCGGT
CAGCATGAACAACAGTAACCATCTTGTAAACAGTGACAATGTGGGCTATGCATCTTACCTGCTTG
AGCAAGAGAAGAACAAAGGATATCTACCTGGACAGGGGCCATTTGTAGCAGCCTTTGCTTCATCA
AACCTAGGAGATGTGTCCCCCAACATTCTTGGACCACGTTGCATCAACACAGGAGAGTCCTGTGA
TAACGCCAATAGCACTTGTCCCATTGGTGGGCCTAGCATGTGCATTGCATTGTAAGGGACCTGGACAGG
ATATGTTTGACAGCACACAAATTATAGGACGGGCCATGTATCAGAGAGCAAAGTCAAAACATGT
AAACCAGCATTGGGCTACAGTTTTGCAGCTGGCACTATTGATGGAGTTGGAGGCCTCAATTTTAC
ACAGGGGAAAACAGAAGGGGATCCATTTTGGGACACCATTCGGGACCAGATCCTGGGAAAGCC
ATCTGAAGAAATTAAAGAATGTCATAAAACCCATCCTTCTTCACACCGGAGAACTATCAAAACC
AACCTCACCCCTGGCATCCAGACATTGTTGATGTTCAGATTATTACCCTTGGGTCCTTGGCCATAA
CTGCCATCCCCGGGGAGTTTACGACCATGTCTGGACGAAGACTTCGAGAGGCAGTTCAAGCAGA
ATTTGCATCTCATGGGATGCAGAACATGACTGTTGTTATTTCAGGTCTATGCAACGTCTATACACA
TTACATTACCACTTATGAAGAATACCAGGCTCAGCGATATGAGGCAGCATCGACAATTTATGGAC
CGCACACATTATCTGCTTACATTCAGCTCTTCAGAAACCTTGCTAAGGCTATTGCTACGGACACGG
TAGCCAACCTGAGCAGAGGTCCAGAACCTCCCTTTTTCAAACAATTAATAGTTCCATTAATTCCTA
GTATTGTGGATAGAGCACCAAAAGGCAGAACTTTCGGGGATGTCCTGCAGCCAGCAAAACCTGA
ATACAGAGTGGGGGAAGTTGCTGAAGTTATATTTGTAGGTGCTAACCCGAAGAATTCAGTACAA
AACCAGACCCATCAGACCTTCCTCACTGTGGAGAAATATGAGGCTACTTCAACATCGTGGCAGAT
AGTGTGTAATGATGCCTCCTGGGAGACTCGTTTTTATTGGCACAAGGGACTCCTGGGTCTGAGTA
ATGCAACAGTGGAATGGCATATTCCAGACACTGCCCAGCCTGGAATCTACAGAATAAGATATTTT
GGACACAATCGGAAGCAGGACATTCTGAAGCCTGCTGTCATACTTTCATTTGAAGGCACTTCCCC
GGCTTTTGAAGTTGTAACTATTTAGTGA (SEQ ID NO:9)
```

ASAH2B transcript variant 1

```
ATGAGGCAGCATCGACAATTTATGGACCGCACGCATTATCTGCTTACATTCAGCTCTTCAGAAACC
TTGCTAAGGCTATTGCTACGTATTGTGGATAGAGCACCAAAAGGCAGAACTTTCGGGGATGTCCT
GCAGCCAGCAAAACCTGAATACAGAGTGGGGGGAAGTTGCTGAAGTTATATTTGTAGGTGCTAAC
```

TABLE 1-continued

| Gene | Open Reading Frame |
|---|---|
| | CCGAAGAATTCAGTACAAAACCAGACCCATCAGACCTTCCTCACTGTGGAGAAATATGAGGCTAC<br>TTCAACATCGTGGCAGATAGTGTGTAATGATGCCTCCTGGGAGACTCGTTTTTATTGGCACAAGG<br>GACTCCTGGGTCTGAGTAATGCAACAGTGGAATGGCATATTCCAGACACTGCCCAGCCTGGAATC<br>TACAGAATAAGATATTTTGGACACAATCGGAAGCAGGACATTCTGAAGCCTGCTGTCATACTTTC<br>ATTTGAAGGCACTTCCCCGGCTTTTGAAGTTGTAACTATTTAGTGA (SEQ ID NO: 10) |
| ASAH2B<br>transcript<br>variant 3 | ATGGTAGCCAACCTGAGCAGAGGTCCAGAACCTCCCTTTTTCAAACAATTAATAGTTCCATTAATT<br>CCTAGTATTGTGGATAGAGCACCAAAAGGCAGAACTTTCGGGGATGTCCTGCAGCCAGCAAAAC<br>CTGAATACAGAGTGGGGGAAGTTGCTGAAGTTATATTTGTAGGTGCTAACCCGAAGAATTCAGT<br>ACAAAACCAGACCCATCAGACCTTCCTCACTGTGGAGAAATATGAGGCTACTTCAACATCGTGGC<br>AGATAGTGTGTAATGATGCCTCCTGGGAGACTCGTTTTTATTGGCACAAGGGACTCCTGGGTCTG<br>AGTAATGCAACAGTGGAATGGCATATTCCAGACACTGCCCAGCCTGGAATCTACAGAATAAGATA<br>TTTTGGACACAATCGGAAGCAGGACATTCTGAAGCCTGCTGTCATACTTTCATTTGAAGGCACTTC<br>CCCGGCTTTTGAAGTTGTAACTATTTAGTGAATGGTAGCCAACCTGAGCAGAGGTCCAGAACCTC<br>CCTTTTTCAAACAATTAATAGTTCCATTAATTCCTAGTATTGTGGATAGAGCACCAAAAGGCAGAA<br>CTTTCGGGGATGTCCTGCAGCCAGCAAAACCTGAATACAGAGTGGGGGAAGTTGCTGAAGTTAT<br>ATTTGTAGGTGCTAACCCGAAGAATTCAGTACAAAACCAGACCCATCAGACCTTCCTCACTGTGG<br>AGAAATATGAGGCTACTTCAACATCGTGGCAGATAGTGTGTAATGATGCCTCCTGGGAGACTCGT<br>TTTTATTGGCACAAGGGACTCCTGGGTCTGAGTAATGCAACAGTGGAATGGCATATTCCAGACAC<br>TGCCCAGCCTGGAATCTACAGAATAAGATATTTTGGACACAATCGGAAGCAGGACATTCTGAAGC<br>CTGCTGTCATACTTTCATTTGAAGGCACTTCCCCGGCTTTTGAAGTTGTAACTATTTAGTGA (SEQ<br>ID NO: 11) |
| ASAH2B<br>transcript<br>variant 4 | ATGGTAGCCAACCTGAGCAGAGGTCCAGAACCTCCCTTTTTCAAACAATTAATAGTTCCATTAATT<br>CCTAGTATTGTGGATAGAGCACCAAAAGGCAGAACTTTCGGGGATGTCCTGCAGCCAGCAAAAC<br>CTGAATACAGAGTGGGGGAAGTTGCTGAAGTTATATTTGTAGGTGCTAACCCGAAGAATTCAGT<br>ACAAAACCAGACCCATCAGACCTTCCTCACTGTGGAGAAATATGAGGCTACTTCAACATCGTGGC<br>AGATAGTGTGTAATGATGCCTCCTGGGAGACTCGTTTTTATTGGCACAAGGGACTCCTGGGTCTG<br>AGTAATGCAACAGTGGAATGGCATATTCCAGACACTGCCCAGCCTGGAATCTACAGAATAAGATA<br>TTTTGGACACAATCGGAAGCAGGACATTCTGAAGCCTGCTGTCATACTTTCATTTGAAGGCACTTC<br>CCCGGCTTTTGAAGTTGTAACTATTTAG (SEQ ID NO: 12) |
| ACER1 | ATGCCTAGCATCTTCGCCTATCAGAGCTCCGAGGTGGACTGGTGTGAGAGCAACTTCCAGTACTC<br>GGAGCTGGTGGCCGAGTTCTACAACACGTTCTCCAATATCCCCTTCTTCATCTTCGGGCCACTGAT<br>GATGCTCCTGATGCACCCGTATGCCCAGAAGCGCTCCCGCTACATTTACGTTGTCTGGGTCCTCTT<br>CATGATCATAGGCCTGTTCTCCATGTATTTCCACATGACGCTCAGCTTCCTGGGCCAGCTGCTGGA<br>CGAGATCGCCATCCTGTGGCTCCTGGGCAGTGGCTATAGCATATGGATGCCCCGCTGCTATTTCC<br>CCTCCTTCCTTGGGGGGAACAGGTCCCAGTTCATCCGCCTGGTCTTCATCACCACTGTGGTCAGCA<br>CCCTTCTGTCCTTCCTGCGGCCCACGGTCAACGCCTACGCCCTCAACAGCATTGCCCTGCACATTCT<br>CTACATCGTGTGCCAGGAGTACAGGAAGACCAGCAATAAGGAGCTTCGGCCACCTGATTGAGGTC<br>TCCGTGGTTTTATGGGCTGTTGCTCTGACCAGCTGGATCAGTGACCGTCTGCTTTGCAGCTTCTGG<br>CAGAGGATTCATTTCTTCTATCTGCACAGCATCTGGCATGTGCTCATCAGCATCACCTTCCCTTATG<br>GCATGGTCACCATGGCCTTGGTGGATGCCAACTATGAGATGCCAGGTGAAACCCTCAAAGTCCGC<br>TACTGGCCTCGGGACAGTTGGCCCGTGGGGCTGCCCTACGTGGAAATCCGGGGTGATGACAAGG<br>ACTGCTGA (SEQ ID NO: 13) |
| ACER2 | ATGGGCGCCCCGCACTGGTGGGACCAGCTGCAGGCTGGTAGCTCGGAGGTGGACTGGTGCGAG<br>GACAACTACACCATCGTGCCTGCTATCGCCGAGTTCTACAACACGATCAGCAATGTCTTATTTTTC<br>ATTTTACCGCCCATCTGCATGTGCTTGTTTCGTCAGTATGCAACATGCTTCAACAGTGGCATCTACT<br>TAATCTGGACTCTTTTTGGTTGTAGTGGGAATTGGATCCGTCTACTTCCATGCAACCCTTAGTTTCTT<br>GGGTCAGATGCTTGATGAACTTGCAGTCCTTTGGGTTCTGATGTGTGCTTTGGCCATGTGGTTCCC<br>CAGAAGGTATCTACCAAAGATCTTTCGGAATGACCGGGGTAGGTTCAAGGTGGTGGTCAGTGTC<br>CTGTCTGCGGTTACGACGTGCCTGGCATTTGTCAAGCCTGCCATCAACAACATCTCTCTGATGACC<br>CTGGGAGTTCCTTGCACTGCACTGCTCATCGCAGAGCTAAAGAGGTGTGACAACATGCGTGTGTT<br>TAAGCTGGGCCTCTTCTCGGGCCTCTGGTGGACCCTGGCCCTGTTCTGCTGGATCAGTGACCGAG<br>CTTTCTGCGAGCTGCTGTCATCCTTCAACTTCCCCTACCTGCACTGCATGTGGCACATCCTCATCTG<br>CCTTGCTGCCTACCTGGGCTGTGTATGCTTTGCCTACTTTGATGCTGCCTCAGAGATTCCTGAGCA<br>AGGCCCTGTCATCAAGTTCTGGCCCAATGAGAAATGGGCCTTCATTGGTGTCCCCTATGTGTCCCT<br>CCTGTGTGCCAACAAGAAATCATCAGTCAAGATCACGTGA (SEQ ID NO: 14) |
| ACER3<br>transcript<br>variant 1 | ATGGCTCCGGCCGCGGACCGAGAGGGCTACTGGGGCCCCACGACCTCCACGCTGGACTGGTGCG<br>AGGAGAACTACTCCGTGACCTGGTACATCGCCGAGTTCTGGAATACAGTGAGTAACCTGATCATG<br>ATTATACCTCCAATGTTCGGTGCAGTTCAGAGTGTTAGAGACGGTCTGGAAAAGCGGTACATTGC<br>TTCTTATTTAGCACTCACAGTGGTAGGAATGGGATCCTGGTGCTTCCACATGACTCTGAAATATGA<br>AATGCAGCTATTGGATGAACTCCCAATGATATACAGCTGTTGCATATTTGTGTACTGCATGTTTGA<br>ATGTTTCAAGATCAAGAACTCAGTAAACTACCATCTGCTTTTTACCTTAGTTCTATTCAGTTTAATA<br>GTAACCACAGTTTACCTTAAGGTAAAAGAGCCGATATTCCATCAGGTCATGTATGGAATGTTGGT<br>CTTTACATTAGTACTTCGATCTATTTATATTGTTACATGGGTTTATCCATGGCTTAGAGGACTGGGT<br>TATACATCATTGGGTATATTTTTATTGGGATTTTTATTTTGGAATATAGATAACATATTTTGTGAGT<br>CACTGAGGAACTTTCGAAAGAAGGTACCACCTATCATAGGTATTACCACACAATTTCATGCATGG<br>TGGCATATTTTAACTGGCCTTGGTTCCTATCTTCACATCCTTTTCAGTTTGTATACAAGAACACTTT<br>ACCTGAGATATAGGCCAAAAGTGAAGTTTCTCTTTGGAATCTGGCCAGTGATCCTGTTTGAGCCTC<br>TCAGGAAGCATTGA (SEQ ID NO: 15) |
| ACER3<br>transcript<br>variant 2 | ATGGCTCCGGCCGCGGACCGAGAGGGCTACTGGGGCCCCACGACCTCCACGCTGGACTGGTGCG<br>AGGAGAACTACTCCGTGACCTGGTACATCGCCGAGTTCTTGGTAGGAATGGGATCCTGGTGCTTC<br>CACATGACTCTGAAATATGAAATGCAGCTATTGGATGAACTCCCAATGATATACAGCTGTTGCAT<br>ATTTGTGTACTGCATGTTTGAATGTTTCAAGATCAAGAACTCAGTAAACTACCATCTGCTTTTTACC |

TABLE 1-continued

| Gene | Open Reading Frame |
|---|---|
|  | TTAGTTCTATTCAGTTTAATAGTAACCACAGTTTACCTTAAGGTAAAAGAGCCGATATTCCATCAG<br>GTCATGTATGGAATGTTGGTCTTTACATTAGTACTTCGATCTATTTATATTGTTACATGGGTTTATC<br>CATGGCTTAGAGGACTGGGTTATACATCATTGGGTATATTTTTATTGGGATTTTTATTTTGGAATA<br>TAGATAACATATTTTGTGAGTCACTGAGGAACTTTCGAAAGAAGGTACCACCTATCATAGGTATT<br>ACCACACAATTTCATGCATGGTGGCATATTTTAACTGGCCTTGGTTCCTATCTTCACATCCTTTTCA<br>GTTTGTATACAAGAACACTTTACCTGAGATATAGGCCAAAGTGAAGTTTCTCTTTGGAATCTGGC<br>CAGTGATCCTGTTTGAGCCTCTCAGGAAGCATTGA (SEQ ID NO:16) |
| ACER3<br>transcript<br>variant 3 | ATGATATACAGCTGTTGCATATTTGTGTACTGCATGTTTGAATGTTTCAAGATCAAGAACTCAGTA<br>AACTACCATCTGCTTTTTACCTTAGTTCTATTCAGTTTAATAGTAACCACAGTTTACCTTAAGGTAA<br>AAGAGCCGATATTCCATCAGGTCATGTATGGAATGTTGGTCTTTACATTAGTACTTCGATCTATTT<br>ATATTGTTACATGGGTTTATCCATGGCTTAGAGGACTGGGTTATACATCATTGGGTATATTTTTAT<br>TGGGATTTTTATTTTGGAATATAGATAACATATTTTGTGAGTCACTGAGGAACTTTCGAAAGAAG<br>GTACCACCTATCATAGGTATTACCACACAATTTCATGCATGGTGGCATATTTTAACTGGCCTTGGT<br>TCCTATCTTCACATCCTTTTCAGTTTGTATACAAGAACACTTTACCTGAGATATAGGCCAAAGTGA<br>AGTTTCTCTTTGGAATCTGGCCAGTGATCCTGTTTGAGCCTCTCAGGAAGCATIGA (SEQ ID NO:<br>17) |
| Sphk2 | ATGAATGGACACCTTGAAGCAGAGGAGCAGCAGGACCAGAGGCCAGACCAGGAGCTGACCGGG<br>AGCTGGGGCCACGGGCCTAGGAGCACCCTGGTCAGGGCTAAGGCCATGGCCCCGCCCCCACCGC<br>CACTGGCTGCCAGCACCCCGCTCCTCCATGGCGAGTTTGGCTCCTACCCAGCCCGAGGCCCACGC<br>TTTGCCCTCACCCTTACATCGCAGGCCCTGCACATACAGCGGCTGCGCCCCAAACCTGAAGCCAG<br>GCCCCGGGGTGGCCTGGTCCCGTTGGCCGAGGTCTCAGGCTGCTGCACCCTGCGAAGCCGCAGC<br>CCCTCAGACTCAGCGGCCTACTTCTGCATCTACACCTACCCTCGGGGCCGGCGCGGGGCCCGGCG<br>CAGAGCCACTCGCACCTTCCGGGCAGATGGGGCCGCCACCTACGAAGAGAACCGTGCCGAGGCC<br>CAGCGCTGGGCCACTGCCCTCACCTGTCTGCTCCGAGGACTGCCACTGCCCGGGGATGGGGAGA<br>TCACCCCTGACCTGCTACCTCGGCCGCCCCGGTTGCTTCTATTGGTCAATCCCTTTGGGGGTCGGG<br>GCCTGGCCTGGCAGTGGTGTAAGAACCACGTGCTTCCCATGATCTCTGAAGCTGGGCTGTCCTTC<br>AACCTCATCCAGACAGAACGACAGAACCACGCCCGGGAGCTGGTCCAGGGGCTGAGCCTGAGTG<br>AGTGGGATGGCATCGTCACGGTCTCGGGAGACGGGCTGCTCCATGAGGTGCTGAACGGGCTCCT<br>AGATCGCCCTGACTGGGAGGAAGCTGTGAAGATGCCTGTGGGCATCCTCCCCTGCGGCTCGGGC<br>AACGCGCTGGCCGGAGCAGTGAACCAGCACGGGGGATTTGAGCCAGCCCTGGGCCTCGACCTGT<br>TGCTCAACTGCTCACTGTTGCTGTGCCGGGGTGGTGGCCACCCACTGGACCTGCTCTCCGTGACG<br>CTGGCCTCGGGCTCCCGCTGTTTCTCCTTCCTGTCTGTGGCCTGGGGCTTCGTGTCAGATGTGGAT<br>ATCCAGAGCGAGCGCTTCAGGGCCTTGGGCAGTGCCCGCTTCACACTGGGCACGGTGCTGGGCC<br>TCGCCACACTGCACACCTACCGCGGACGCCTCTCCTACCTCCCCGCCACTGTGGAACCTGCCTCGC<br>CCACCCCTGCCCATAGCCTGCCTCGTCCCAAGTCGGAGCTGACCCTAACCCCAGACCCAGCCCCG<br>CCCATGGCCCACTCACCCCTGCATCGTTCTGTGTCTGACCTGCCTCTTCCCCTGCCCCAGCCTGCCC<br>TGGCCTCTCCTGGCTCGCCAGAACCCCTGCCCATCCTGTCCCTCAACGGTGGGGGCCCAGAGCTG<br>GCTGGGGACTGGGGTGGGGCTGGGGATGCTCCGCTGTCCCCGGACCCACTGCTGTCTTCACCTC<br>CTGGCTCTCCCAAGGCAGCTCTACACTCACCCGTCTCCGAAGGGGCCCCCGTAATTCCCCCATCCT<br>CTGGGCTCCCACTTCCCACCCCTGATGCCCGGGTAGGGGCCTCCACCTGCGGCCCGCCCGACCAC<br>CTGCTGCCTCCGCTGGGCACCCCGCTGCCCCCAGACTGGGTGACGCTGGAGGGGGACTTTGTGC<br>TCATGTTGGCCATCTCGCCCAGCCACCTAGGCGCTGACCTGGTGGCAGCTCCGCATGCGCGCTTC<br>GACGACGGCCTGGTGCACCTGTGCTGGGTGCGTAGCGGCATCTCGCGGGCTGCGCTGCTGCGCC<br>TTTTCTTGGCCATGGAGCGTGGTAGCCACTTCAGCCTGGGCTGTCCGCAGCTGGGCTACGCCGCG<br>GCCCGTGCCTTCCGCCTAGAGCCGCTCACACCACGCGGCGTGCTCACAGTGGACGGGGAGCAGG<br>TGGAGTATGGGCCGCTACAGGCACAGATGCACCCTGGCATCGGTACACTGCTCACTGGGCCTCCT<br>GGCTGCCCGGGGGGGGAGCCCTGA (SEQ ID NO: 18) |
| CerK | ATGGGGGCGACGGGGGCGGCGGAGCCGCTGCAATCCGTGCTGTGGGTGAAGCAGCAGCGCTGC<br>GCCGTGAGCCTGGAGCCCGCGCGGGCTCTGCTGCGCTGGTGGCGGAGCCCGGGGCCCGGAGCC<br>GGCGCCCCCGGCGCGGATGCCTGCTCTGTGCCTGTATCTGAGATCATCGCCGTTGAGGAAACAG<br>ACGTTCACGGGAAACATCAAGGCAGTGGAAATGGCAGAAAATGGAAAAGCCTTACGCTTTTAC<br>AGTTCACTGTGTAAAGAGAGCACGACGGCACCGCTGGAAGTGGGCGCAGGTGACTTTCTGGTGT<br>CCAGAGGAGCAGCTGTGTCACTTGTGGCTGCAGACCCTGCGGGAGATGCTGGAGAAGCTGACGT<br>CCAGACCAAAGCATTTACTGGTATTTATCAACCCGTTTGGAGGAAAAGGACAAGGCAAGCGGAT<br>ATATGAAAGAAAAGTGGCACCACTGTTCACCTTAGCCTCCATCACCACTGACATCATCGTTACTGA<br>ACATGCTAATCAGGCCAAGGAGACTCTGTATGAGATTAACATAGACAAATACGACGGCATCGTCT<br>GTGTCGGCGGAGATGGTATGTTCAGCGAGGTGCTGCACGGTCTGATTGGGAGGACGCAGAGGA<br>GCGCCGGGGTCGACCAGAACCACCCCCGGGCTGTGCTGGTCCCCAGTAGCCTCCGGATTGGAAT<br>CATTCCCGCAGGGTCAACGGACTGCGTGTGTTACTCCACCGTGGGCACCAGCGACGCAGAAACCT<br>CGGCGCTGCATATCGTTGTTGGGGACTCGCTGGCCATGGATGTGTCCTCAGTCCACCACAACAGC<br>ACACTCCTTCGCTACTCCGTGTCCCTGCTGGGCTACAGGCTTCTACGGGGACATCATCAAGGACAG<br>TGAGAAGAAACGGTGGTTGGGTCTTGCCAGATACGACTTTTCAGGTTTAAAGACCTTCCTCTCCC<br>ACCACTGCTATGAAGGGACAGTGTCCTTCCTCCCTGCACAACACACGGTGGGATCTCCAAGGGAT<br>AGGAAGCCCTGCCGGGCAGGATGCTTTGTTTGCAGGCAAAGCAAGCAGCAGCTGGAGGAGGAG<br>CAGAAGAAAGCACTGTATGGTTTGGAAGCTGCGGAGGACGTGGAGGAGTGGCAAGTCGTCTGT<br>GGGAAGTTTCTGGCCATCAATGCCACAAACATGTCCTGTGCTTGTCGCCGGAGCCCCAGGGGCCT<br>CTCCCCGGCTGCCCACTTGGGAGACGGGTCTTCTGACCTCATCCTCATCCGGAAATGCTCCAGGTT<br>CAATTTTCTGAGATTTCTCATCAGGCACACCAACCAGCAGGACCAGTTTGACTTCACTTTTTGTTGA<br>AGTTTATCGCGTCAAGAAATTCCAGTTTACGTCGAAGCACATGGAGGATGAGGACAGCGACCTC<br>AAGGAGGGGGGGAAGAAGCGCTTTGGGCACATTTGCAGCGCACCCCTCCTGCTGCTGCACCG<br>TCTCCAACAGCTCCTGGAACTGCGACGGGGAGGTCCTGCACAGTGCCATCGAGGTCAGAGT<br>CCACTGCCAGCTGGTTCGACTCTTTGCACGAGGAATTGAAGAGAATCCGAAGCCAGACTCACACA<br>GCTGA<br>(SEQ ID NO: 19) |

Reducing Cell Death in Rat Myocardium

In order to characterize the dynamics of cell death as well as expression of genes that are involved in the metabolism and signaling of sphingolipids in the heart as a result of myocardial infarction (MI) in mice, hearts were infarcted by ligation of the left anterior descending artery (LAD) and harvested at different time points post ligation.

Figure 1A:
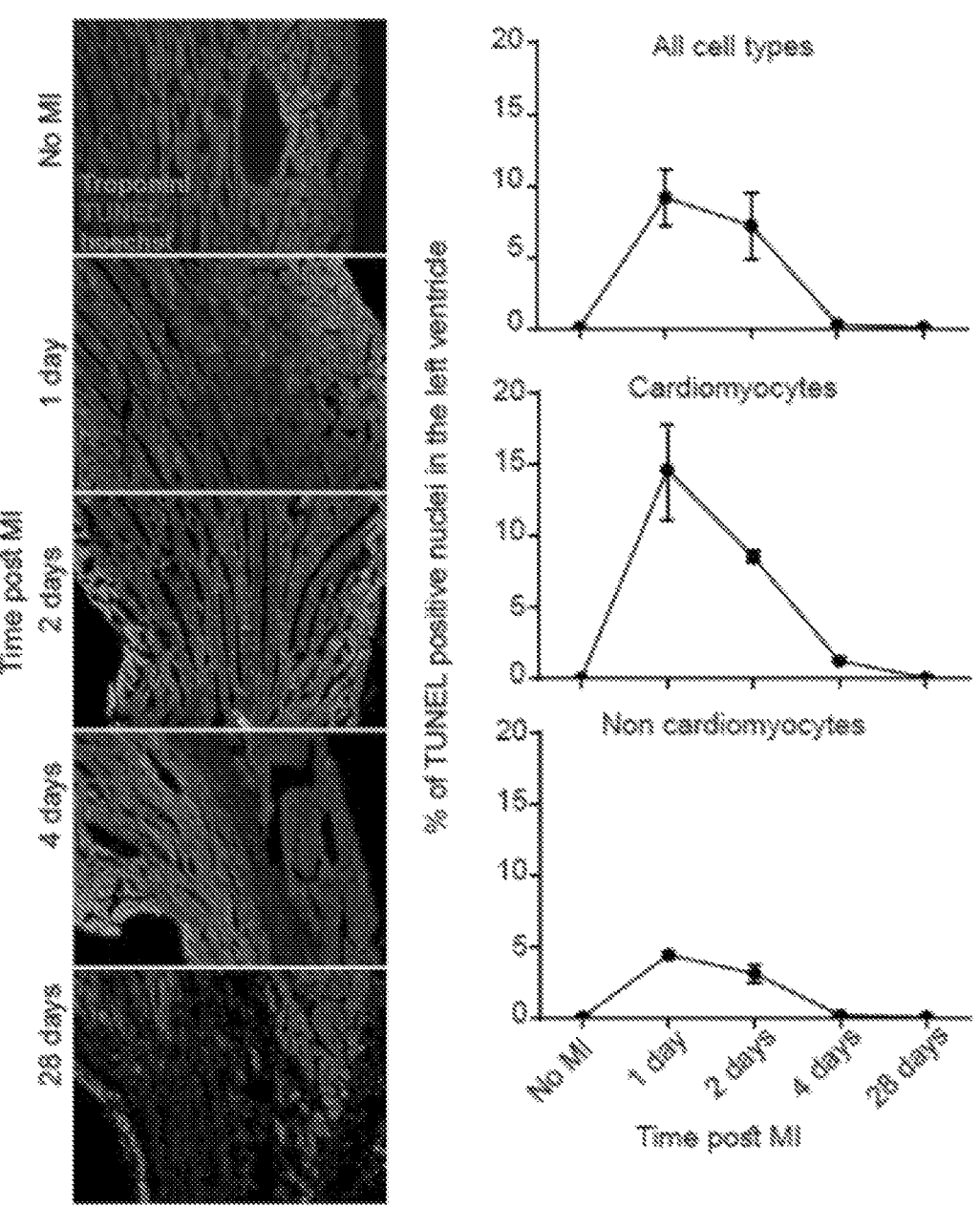
Figure 2A:
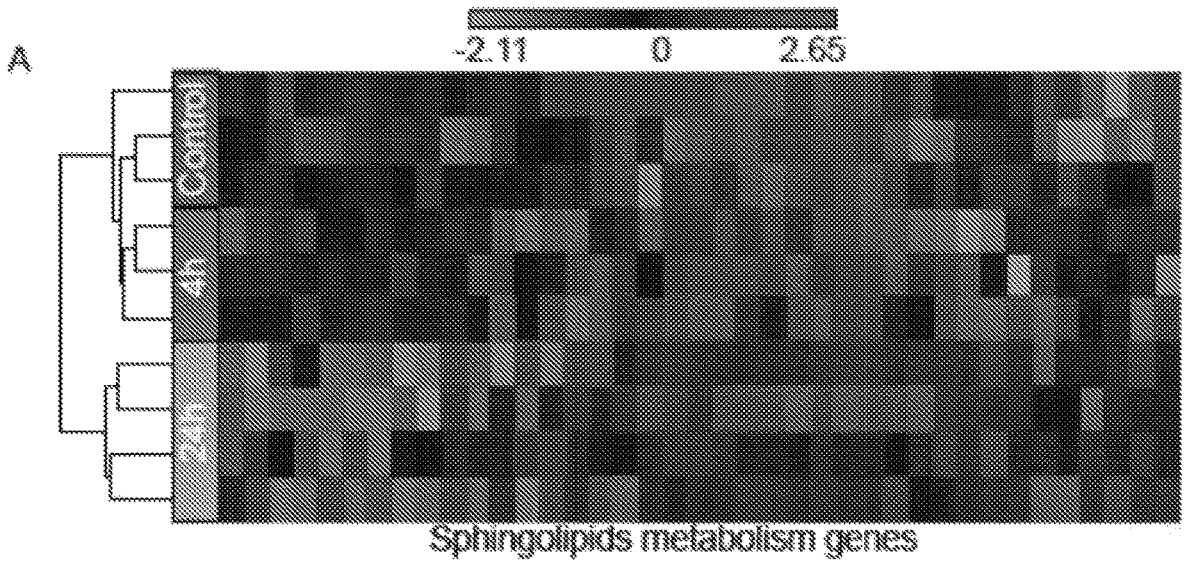
FIGS. 2A-2E show the characterization of cell death dynamics and sphingolipid-metabolizing enzymes expression in mouse heart after MI. A) Dendogram of Sphingolipids metabolism genes transcriptome in sham hearts, at 4 and 24 hours post ligation. B) Volcano plots of Sphingolipids metabolism genes transcriptome and sphingolipids signaling pathway transcriptome, 4 and 24 hours. C) Protein levels of pro-caspase and cleaved caspase in the LV of sham hearts and hearts 24 hours post MI. D) Protein levels of Sphk1 and β-actin in sham hearts and hearts 4 and 24 hours post MI. E) Protein levels of S1PR2 and β-actin in sham hearts and hearts 4 and 24 hours post MI.
Figures 2B, 2C, 2D, 2E:
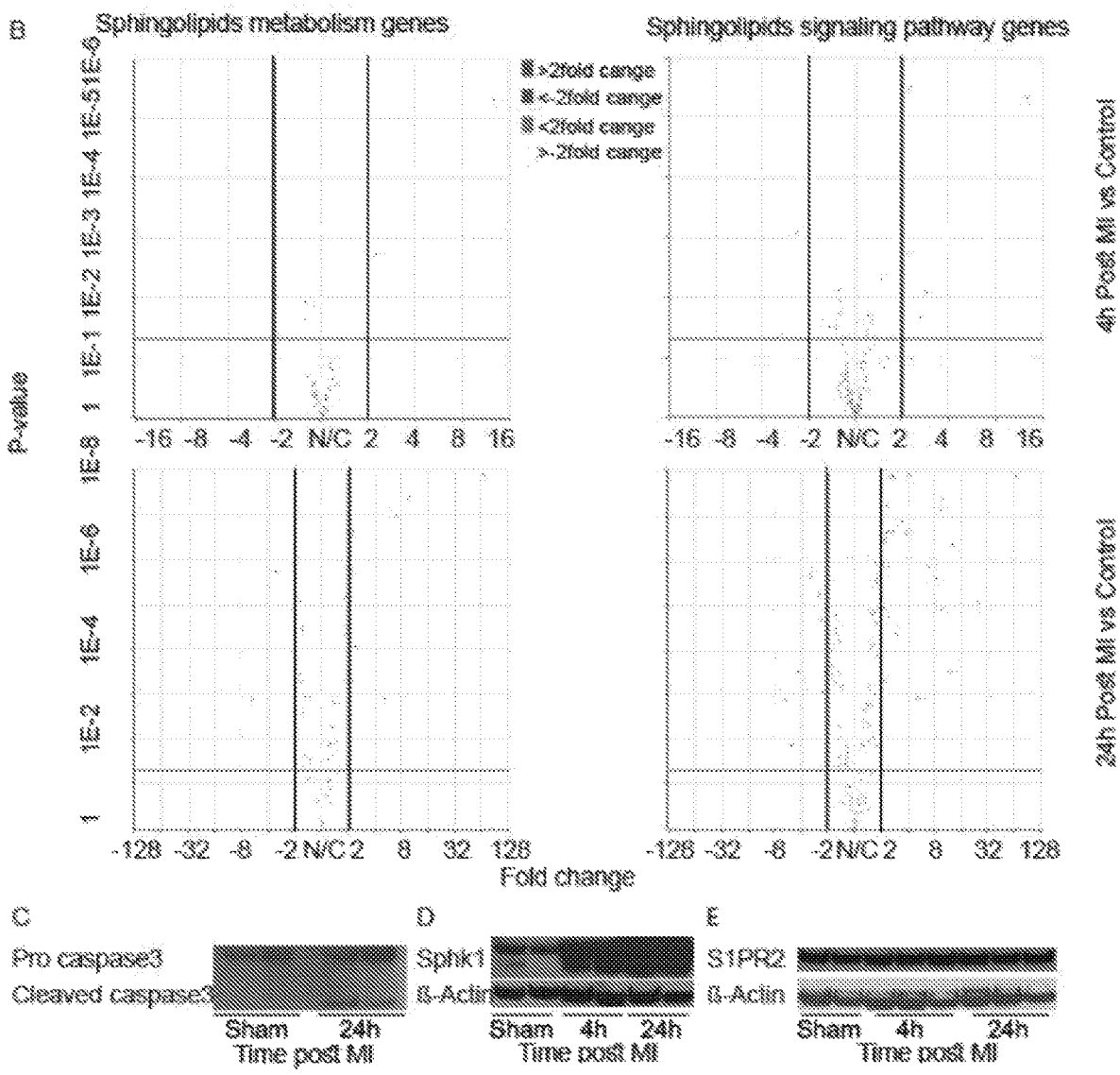
Figure 3:
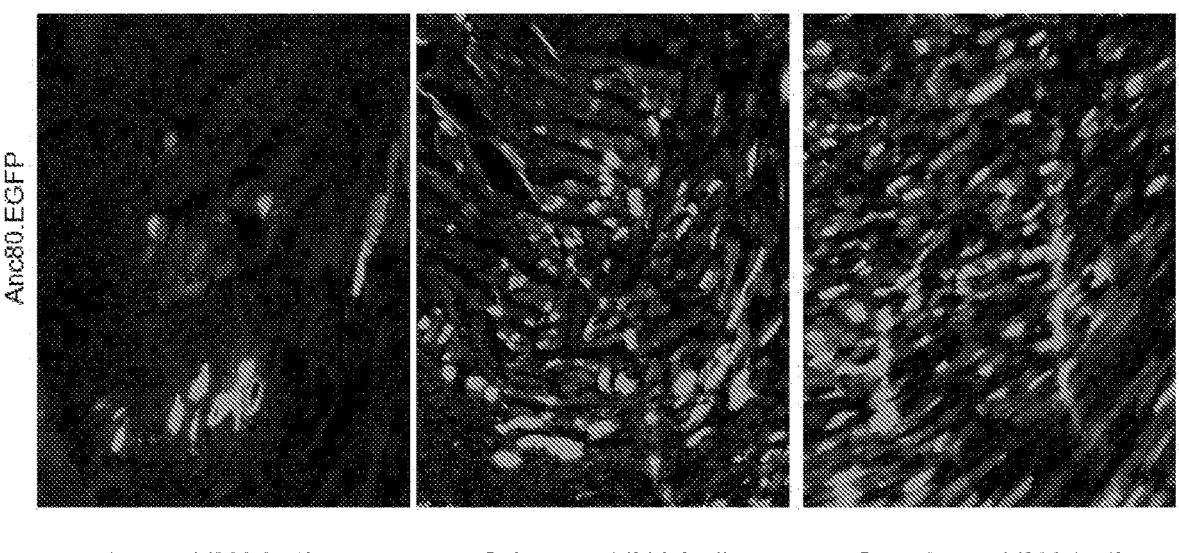
FIG. 3 shows EGFP expression dynamics after direct injection into the heart of $2.5 \times 10^{11}$ genome copies (GC) of Anc80 encoding EGFP.
Figure 4:
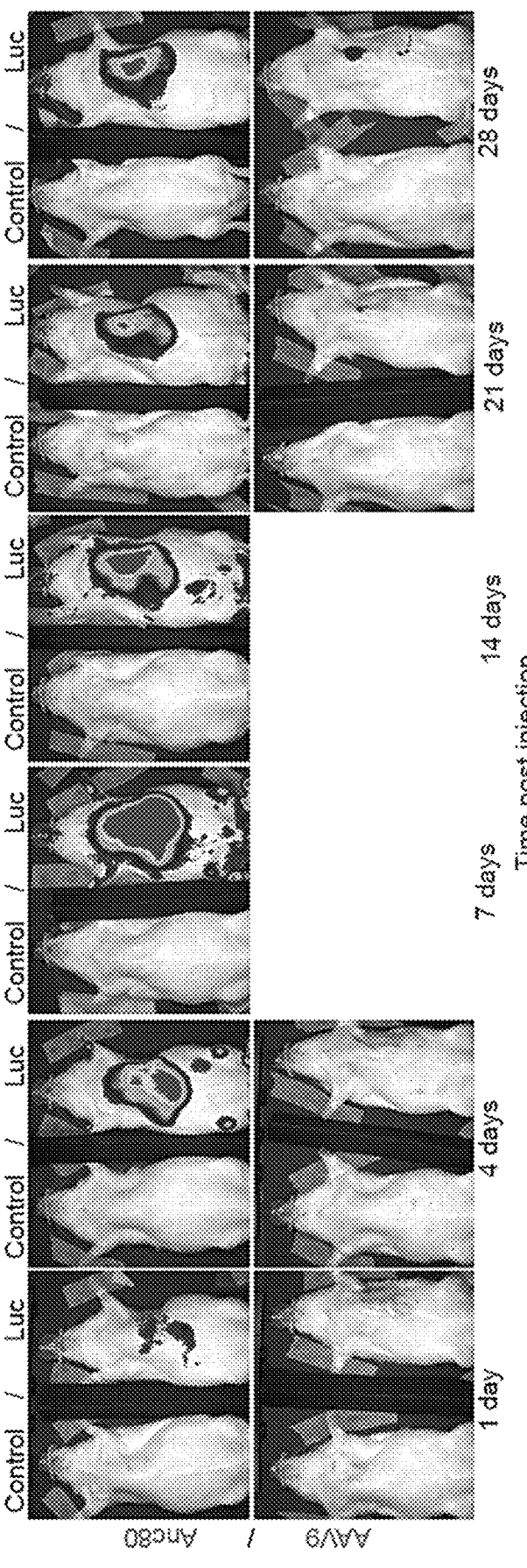
FIG. 4 Luciferase (Luc) expression dynamics after direct injection to the heart of Anc80 or AAV9 encoding firefly luciferase.
Figure 4:
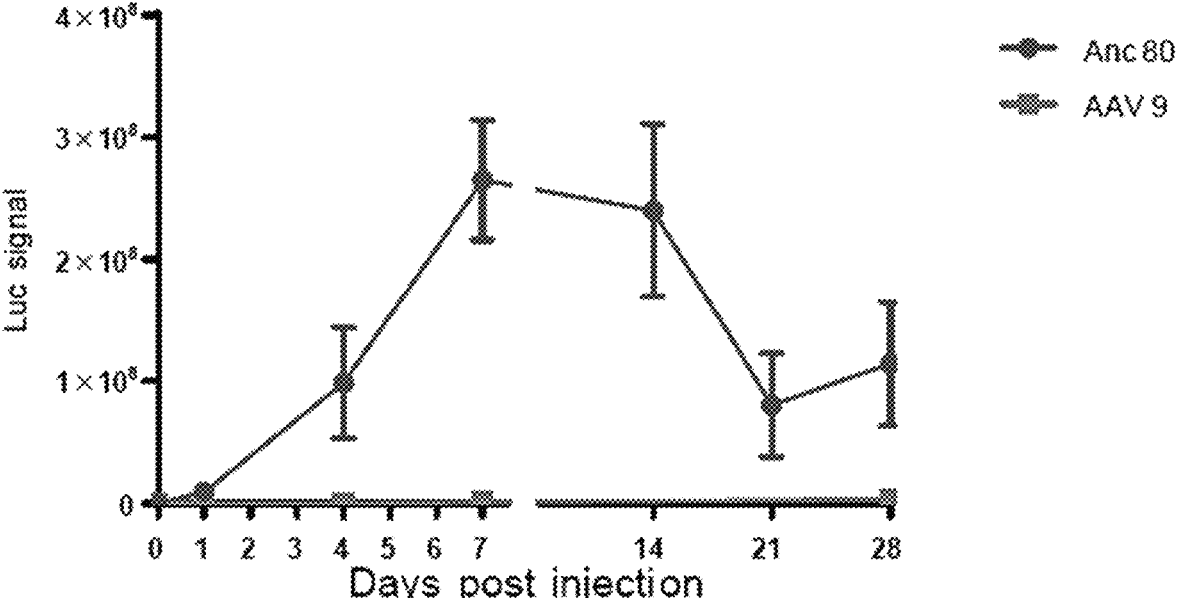

For cell death assessment the hearts were harvested at 1, 2, 4, and 28 days post MI and from sham operated mice. TUNEL stain was used to assess DNA fragmentation in cardiac cells. Troponin-I immunostaining was used to distinguish between cardiomyocytes and non-cardiomyocytes (FIG. 1A). The highest level of DNA fragmentation was found 24 h post MI with 9±2% of total cells in LV having fragmented DNA, 15±3% of CM and 4±0.2% of non CM. The levels of DNA fragmentation two days post MI reduced both in CM and non CM and reached to basal levels 28 d post MI with 0.1±0.1% of total cells 0.07±0.08% of CM and 0.12±0.1% of non CM comparable to the levels in the hearts of control mice. Cleaved Caspase3 immunoblotting 24 h post MI confirmed high levels of cell death in the infarcted area (FIG. 5C).

Figure 5:
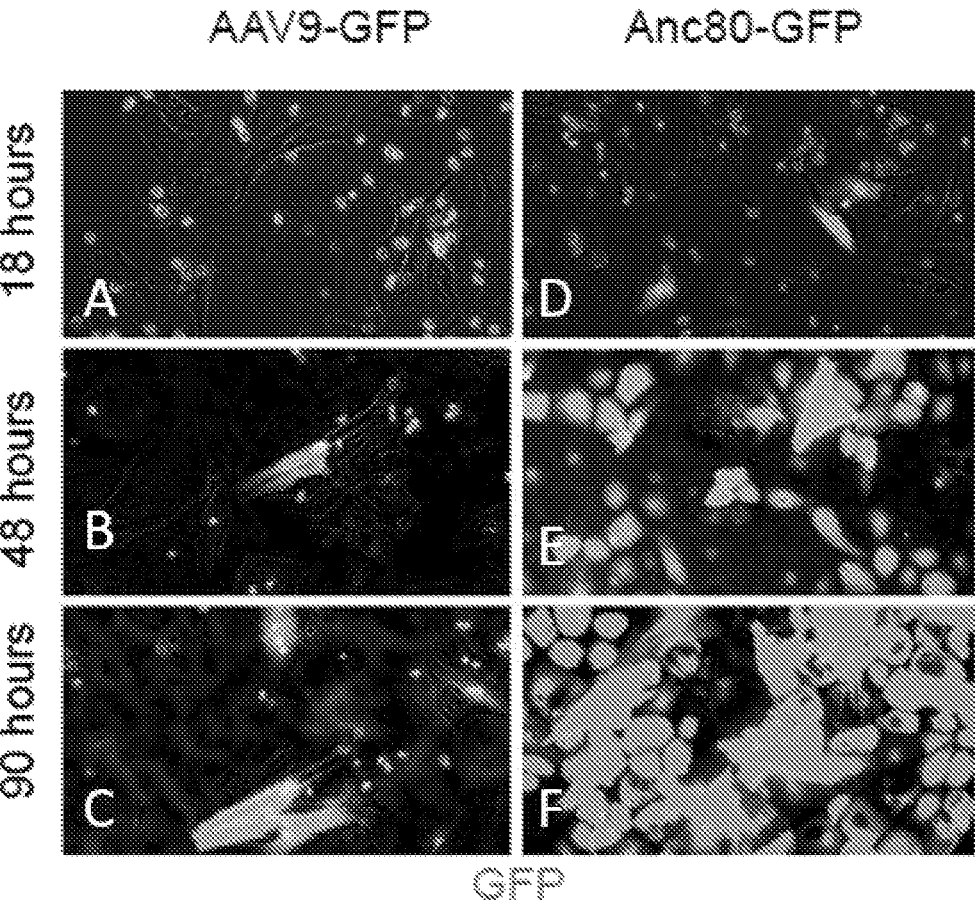
FIG. 5 shows EGFP expression dynamics post infection with $1 \times 10^{10}$ GC/$1 \times 10^{6}$ cells of Anc80 or AAV9 encoding EGFP. Neonatal rat cardiomyocytes were infected with $1.25 \times 10^{10}$ GC of Anc80 (A, B, C) or AAV9 (D, E, F) encoding EGFP. The cells were imaged using a fluorescence microscope 18 hours (A, D) 48 hours (B, E) and 96 hours (C, F) post infection.
Figure 6:
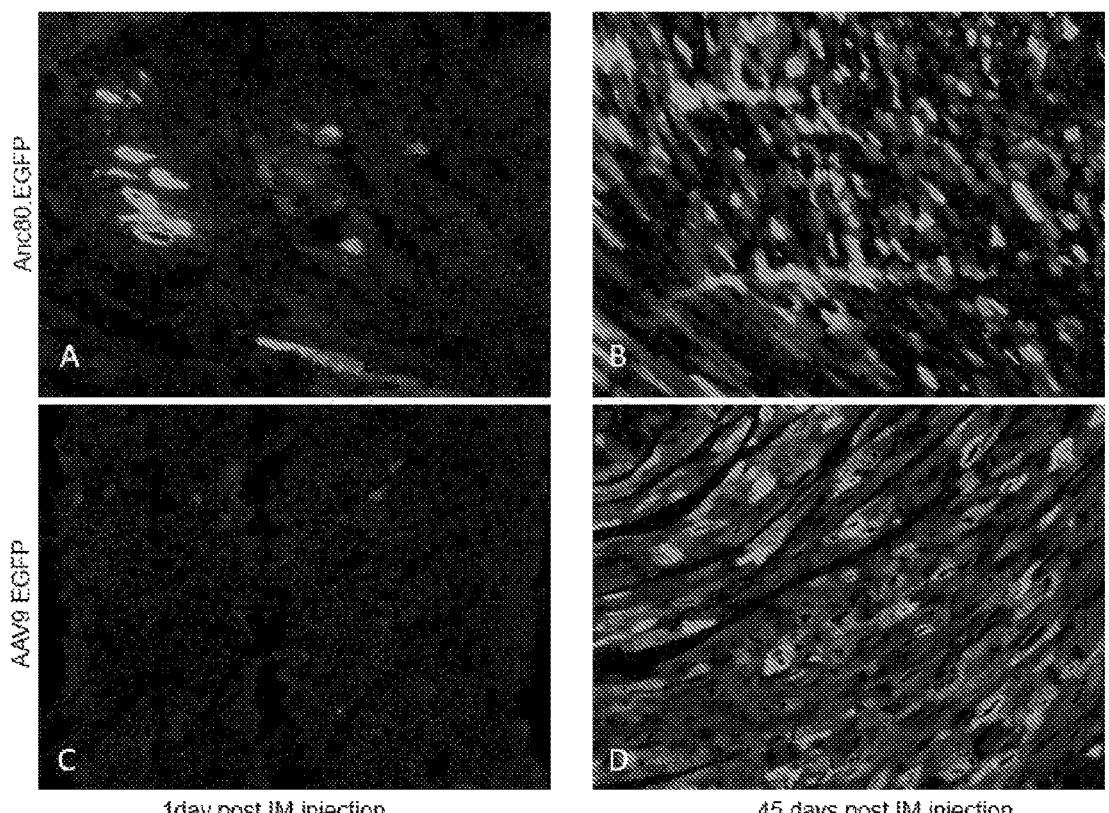
FIG. 6 show EGFP expression dynamics after IM injection of $2.5 \times 10^{11}$ GC of Anc80 or AAV9 encoding EGFP. Adult rat hearts were injected intramyocardially (IM) with $2.5 \times 10^{11}$ GC of Anc80 (A, B) or AAV9 (C, D) encoding EGFP. The hearts were collected 1 day (A, C) and 45 days (B, D) post injection. Heart sections were imaged using a fluorescence microscope.
Figure 7:
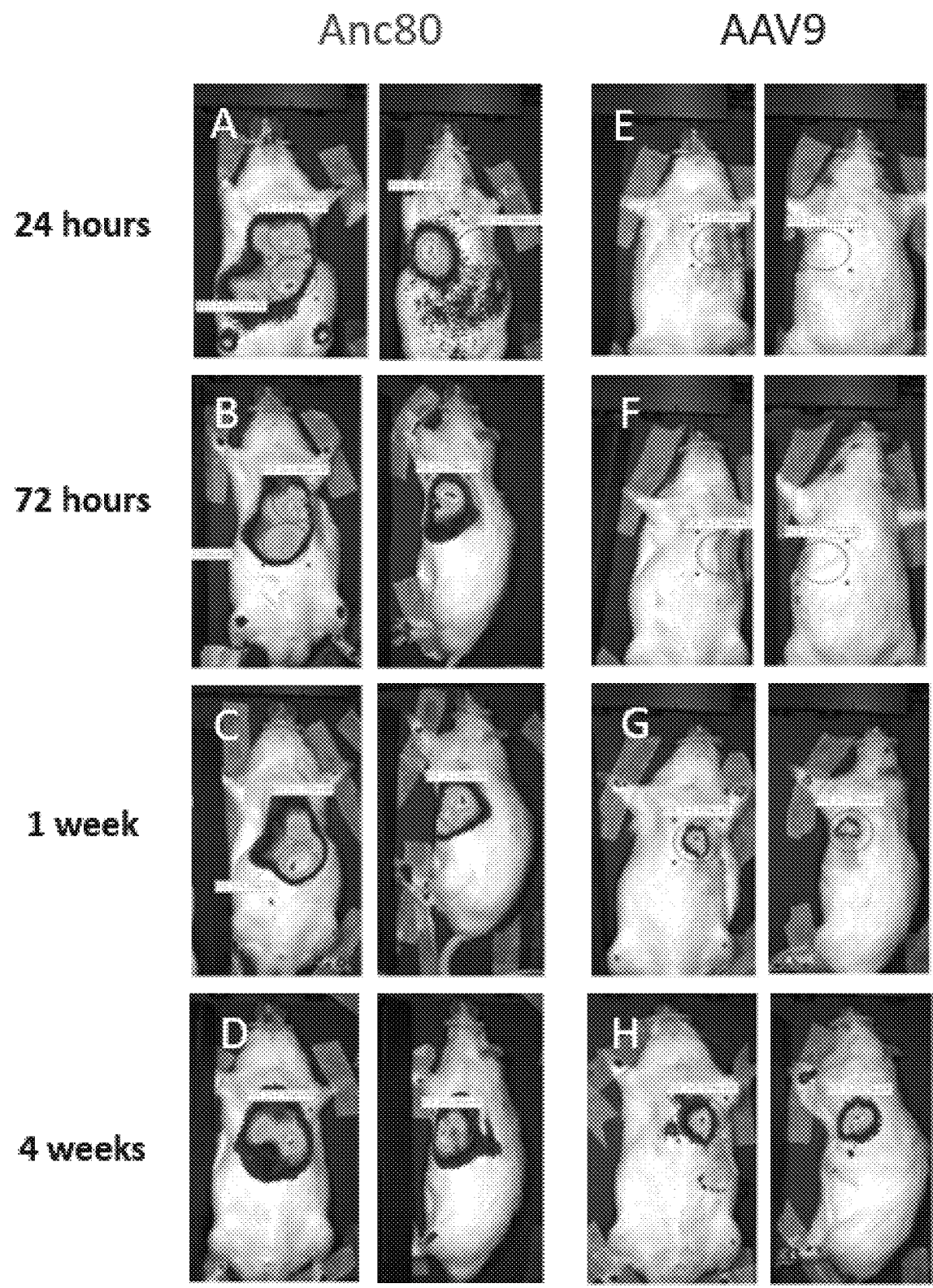
FIG. 7 shows the biodistribution of Anc80 and AAV9 in a rat model (IVIS). Adult rat hearts were injected intramyocardially (IM) with $7.5 \times 10^{10}$ GC of Anc80 (A, B, C, D) or AAV9 (E, F, G, H) encoding to firefly luciferase. Bioluminescence was measured using a IVIS machine 24 hours (A, E), 72 hours (B, F) 1 week (C, G) and 4 weeks (D, H) post injection. I) Luciferase activity kinetics as measured using an IVIS machine.
Figure 8:
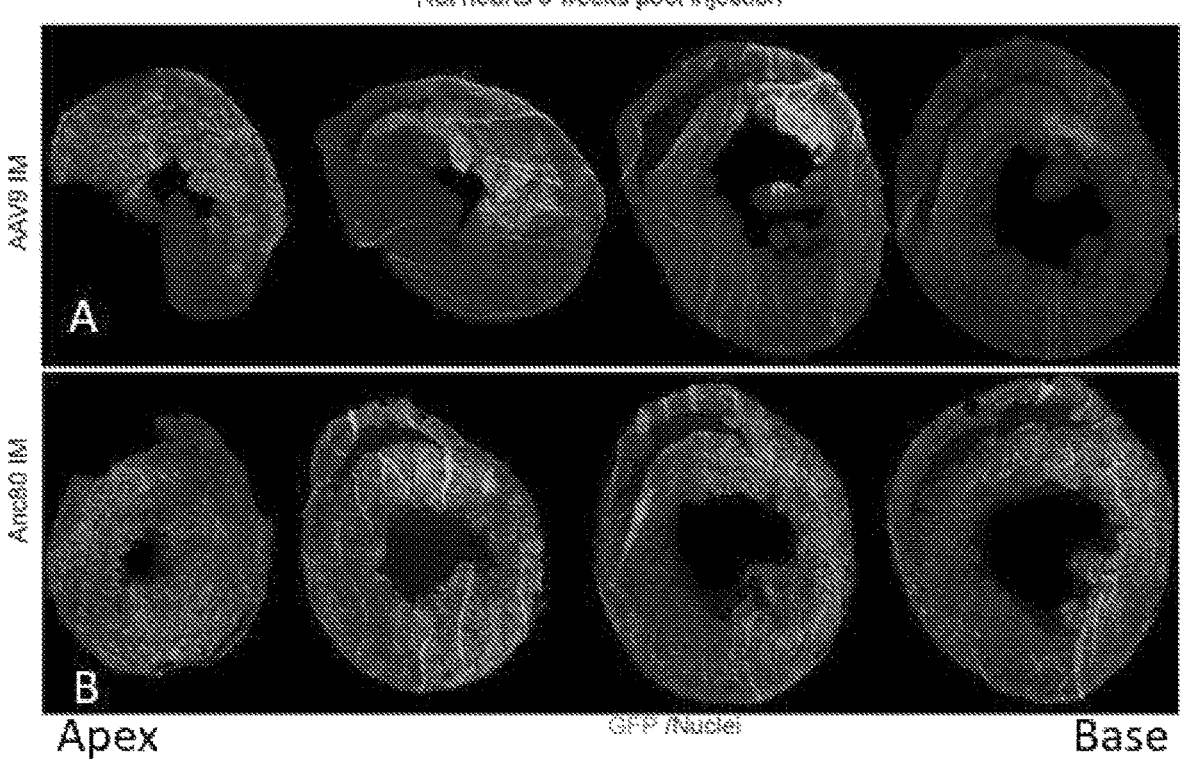

Sphingolipid metabolism and signaling pathway partial transcriptomes were studied in hearts of sham operated mice or mice 4 h and 24 h post MI. We focused on two partially overlapping sets of genes: Sphingolipid metabolism genes based on KEGG PATHWAY map00600 and Sphingolipid signaling pathway genes based on KEGG PATHWAY map04071 [11]. In the Sphingolipid metabolism transcriptome 4 h post ligation, 2 genes were significantly upregulated by more than 2 fold and one was downregulated by less than −2 fold. 24 h post MI, 10 genes were significantly upregulated by more than 2 fold and 2 were downregulated by less than −2 fold. A total of 12 out of 39 genes (not shown) related to sphingolipid metabolism were significantly upregulated. In the Sphingolipids signaling pathway transcriptome 4 h post ligation 5 genes were significantly upregulated by more than 2 fold and 2 were downregulated by less than −2 fold. 24 h post MI, 28 genes were significantly upregulated by more than 2 fold and 10 were downregulated by less than −2 fold totals of 38 out of 82 genes (FIG. 1B and FIG. 5)

The dendrograms of both transcriptomes (FIG. 1B and FIG. 5A) shows that the control group and the 4 h post MI group are clustered together while the 24 h post MI is clustered as a separate group suggesting that the major alterations in sphingolipids metabolism and signaling pathway related genes expression occurs more than 4 h post MI.

In order to study the role of ceramide metabolites on cell death and heart function post MI we chose to alter ceramide metabolism and signaling pathway by enhancing ceramide hydrolysis and S1P formation. First we confirm the RNA-seq DATA for the main genes that are involved in this process namely: Acid ceramidase (AC), Sphingosine Kinase 1 (Sphk1) and Sphingosine-1-Phosphate Receptor 2 (S1PR2) by qPCR and western blot analysis of hearts from an independent experiment. In agreement with the results of the RNAseq analysis, the relative levels of AC mRNA didn't change significantly (FIG. 1B). The levels of AC precursor did not change however, the levels of AC α subunit and β subunit gradually increased during infarct development (FIG. 1C) The increase in α and β subunits is accompanied by an increase in the activity level of AC (FIG. 1D). The mRNA levels of Sphk1 increased by 6 times at 4 h and by 35 times at 24 h. Western blot analysis revealed a dramatic increase in the levels of Sphk1 protein 4 h and 24 h post MI (FIGS. 1B and C and FIG. 5D). The relative levels of S1PR2 mRNA declined by 50% 4 h post MI and returned to normal after 24 h. The levels of S1PR2 did not change 4 h or 24 h post MI (FIG. 1B and FIG. 5E).

Acid ceramidase catalyzes the hydrolysis of ceramide into sphingosine and free fatty acid [18]. While it has been reported that sphingosine is capable of disassembling mitochondrial ceramide channels suggesting the existence of an anti-apoptotic property of sphingosine [19, 20] other evidence support a positive role of sphingosine in the execution of apoptotic or necrotic cell death [21]. Moreover, it was suggested by Benaim et al [22] that sphingosine can disturb the homeostasis of cellular calcium by inhibiting the activity of sarco(endo)plasmic reticulum Ca(2+)-ATPase (SERCA) which has a pivotal role in proper cardiac function [23, 24]. The two genes that encode sphingosine kinase, Sphk1 and Sphk2, catalyze the phosphorylation of sphingosine to S1P and have shown to possess cardioprotective properties [25]. Duan et al reported that adenoviral mediated overexpression of Sphk1 in rat hearts can protect the treated hearts from ischemia and reperfusion injury [26]. Our transcriptome analysis shows that the expression levels of Sphk1 are elevated by 12 and 67 fold 4 and 24 hours post-MI respectively. A similar trend was found with qPCR analyzed of Sphk1 levels in an independent experiment. This was accompanied by a significant elevation in Sphk1 protein levels as measured by western blot analysis. The pathway analysis of sphingosine signal transduction revealed up regulation of all the components in the TNF signaling pathway including TNF alpha, TNFR, TRADD, and TRAF2. Interestingly, Xia et al showed that TRAF2 can interact with Sphk1 and that this interaction is necessary for the anti-apoptotic activity of TRAF2 [27]. Recently Guo et al reported a cardioprotective role of TRAF2 [28].

Sphingosine 1 phosphate exerts its activity on cells by activating a family of five G protein-coupled receptors: S1pr1-5. The levels of the two most abundant receptors in the heart namely S1pr1 and 3 are moderately but significantly elevated after MI. In contrast, the levels of S1pr2 4 h after MI are reduced and 24 h post MI the levels are back to normal. The role of S1pr1 and S1pr3 in cardio protection is well established [25] however the role of S1p2 in heart function is less clear. Or results suggest that overexpression of S1p2 in cells and in heart have a neglected effect on cells survival.

Cell Senescence

Senescence is the major cause of suffering, disease, and death in modern times. Senescence, or biological aging, is the slow drop of functional characteristics. Senescence can refer either to cellular senescence or to the senescence of organs or a whole organism. In addition to induced senescence such as aging, there is stress-induced senescence, which is a broad concept including a variety of stress conditions such as oxidative stress, injury, noise exposure, and other sources of damage to cells. These stresses act via intracellular pathways to a state of non-proliferation. Cellular senescence described by Hayflick and Moorhead in the 1960s, is the irreversible arrest of cells following long culture. Telomere shortening is the key mechanism driving replicative senescence in human fibroblasts. Apart from cell cycle arrest, senescent cells have been shown to experience dramatic changes in terms of gene expression, combination of CDK1 activity, heterochromatin formation, metabolism including (sphingolipids metabolism), epigenetics, and a distinct secretion profile known as the Senescence-Associated Secretory Phenotype (SASP) (Copp'e et al., 2014). Senescent cells use the SASP to communicate with the immune system, potentially to facilitate their own clearance (for example pro-inflammatory cytokines) and contribute to disruption of cell and tissue homeostasis and function (Shay and Wright, 2010). It has been shown that "chronic" SASP is able to induce senescence in adjacent young cells, contributing to tissue dysfunction (Acosta et al., 2013, Jurk et al., 2014). Senescent cells also show mitochondrial dysfunction (Passos et al., 2010).

Oxidative stress-induced senescence in the heart caused by myocardial infarction (MI) can trigger cardiomyocyte death or senescence (Huitong et al., 2018). Moreover, senescence can have deleterious effects with chronic, worsening pathologies such as type 2 diabetes (Palmer et al., 2015), atherosclerosis (Gorenne et al., 2006; Wang et al., 2015), Multiple Sclerosis (MS) (Oost et al., 2019), and other chronic diseases.

The involvement of sphingolipids has been studied in multiple organisms and cell types for the regulation of aging and senescence, especially ceramide and sphingosine-1-phosphate (S1P) for induced cellular senescence, distinct from their effect on survival. Significant and wide-ranging evidence defines critical roles of sphingolipid enzymes and pathways in aging and organ injury leading to tissue senescence (Trayssac et al., 2018), including regulation by stress stimuli, p53, participation in growth arrest, SASP, and other aspects of the senescence response. Acid ceramidase is the only protein that can balance the level of ceramide vs S1P by hydrolyzing ceramide to a product that can be phosphorylated to form S1P. The present invention is based on the further discovery that in addition to its role in protecting cells from apoptosis, administration of AC decreased the rate of senescence in vitro, and in vivo, in different cell types and tissues.

Blockage in the coronary arteries reduces the supply of blood to heart muscle and causes dynamic effects within the infarction risk area and around the ischemic border zone. Tissues in the infarction risk area exhibit distinct metabolic changes within a few minutes. Nearly the entire risk area tissues become irreversibly injured during a severe hypoperfusion of 6 hours. On the other hand, the border zone tissues exhibit only moderate metabolic changes due to greater collateral perfusion, including from 45-80% of blood flow regionally in the non-ischemic vascular bed. The ischemic border zone tissues are from the lateral edges of infarct, are approximately 2 mm wide, and increase in width along the subepicardium. Over time, the subepicardial margins of border zone widen due to improved collateral blood flow. The tissues in the border zone region are in, or entering into, senescence.

We tested the effect of AC gene therapy on induced cardiomyocyte senescence in sheep hearts post ischemic injury, using an Anc80 vector encoding AC. Proteomic analysis of the sheep hearts post ischemic injury detected expression of over 4000 genes. These were refined to ~1500 genes by known senescence and age-related gene databases. Functional analysis of the heart post the ischemic stress revealed that there are changes in expression of gene related to senescence mainly in the boarder zone area. Significant changes were observed to 11 out of 25 genes with known roles in the KEGG cellular senescence pathways. Treatment with AC-Anc80 post ischemic injury presented expression levels consistent with control hearts (no ischemic injury) in 10 out of the 11 detected senescence genes. For example, TXN, a major transcription factor involved in senescence and up-regulation of the p53/p21 and p16 tumor suppressor pathways, was differentially expressed. In addition, TP53BP1, a major messenger in DNA damage responses, along with TP53, ATM and other ageing-associated players, was up-regulated post ischemic injury and presented normal levels post treatment with AC-Anc80.

Also, 6 of 8 detected collagen genes that are down-regulated during senescence, were highly elevated above the level of control post AC-Anc80 treatment. These results suggest that AC can be used to prevent senescence\aging in skin cells. PRELP deficiency has been reported to account for many symptoms of Hutchinson-Gilford progeria (HGP). Interestingly PRELP was highly up-regulated post AC-Anc80 treatment. We propose testing the possibility of using AC-Anc80 gene therapy for HGP disease. Moreover, inhibition of FABP4 was recently shown to induce senescence of endothelial cells such as insulin resistance, diabetes mellitus, atherosclerosis, hypertension, cardiac dysfunction (Furuhashi, et al, 2014). FABP4 was down regulated post ischemia and up regulated post AC-Anc80 treatment. Base on these results AC treatments can be applied to prevent senescence in different types of tissues composed of endothelial cells.

Examples

Mice

All animal procedures were performed under protocols approved by the Icahn School of Medicine at Mount Sinai Institutional Care and Use Committee. CFW mice strains, male and female, were used for studies on heart function following myocardial infarction. Before surgery mice were anaesthetized with ketamine 100 mg/kg and xylazine 10 mg/kg cocktail.

hPSC Differentiation

For heart function following myocardial infarction studies, hematoPoietic Stem Cells (hPSCs) (H9) were differentiated along a cardiac lineage as previously described. Briefly, hPSCs were maintained in E8 media and passaged every 4-5 days onto matrigel-coated plates. To generate embryonic bodies (EBs), hPSCs were treated with 1 mg/ml collagenase B (Roche) for 30 min or until cells dissociated from plates. Cells were collected and centrifuged at 1,300 rpm for 3 min, and they were resuspended into small clusters of 50-100 cells by gentle pipetting in differentiation media containing RPMI (Gibco), 2 mmol/L L-glutamine (Invitrogen), 4×10 monothioglycerol (MTG, Sigma), 50 mg/mL ascorbic acid (Sigma), and 150 mg/mL transferrin (Roche). Differentiation media were supplemented with 2 ng/mL BMP4 and 3 mmol Thiazovivin (Millipore) (day 0). EBs were maintained in six-well ultra-low attachment plates (Corning) at 37° C. in 5% CO2, 5% O2, and 90% N2. On day 1, media were changed to differentiation media supplemented with 20 ng/mL BMP4 (R&D Systems) and 20 ng/mL Activin A (R&D Systems). On day 4, media were changed to differentiation media supplemented with 5 ng/mL VEGF (R&D Systems) and 5 mmol/L XAV (Stemgent). After day 8, media were changed every 5 days to differentiation media without supplements.

Synthesis of Anc80.AC

The nucleotide sequence for an embodiment of the Anc80 plasmid described herein is shown below. A map of the vector is also shown in FIG. 16.

Anc80 Plasmid Sequence

| pAAV.CMV. | CTGCGCGCTCGCTCGCTCACTGAGGCCGCCCGGGCAAAGCCCGGGCGTCG |
|---|---|
| WPRE.bGH.d | GGCGACCTTTGGTCGCCCGGCCTCAGTGAGCGAGCGAGCGCGCAGAGAGG |
| na | GAGTGGCCAACTCCATCACTAGGGGTTCCTTGTAGTTAATGATTAACCCGCC |
| | ATGCTACTTATCTACGTAGCCATGCTCTAGGAAGATCGGAATTCGCCCTTAAG |
| | CTAGCTAGTTATTAATAGTAATCAATTACGGGGTCATTAGTTCATAGCCCATAT |
| | ATGGAGTTCCGCGTTACATAACTTACGGTAAATGGCCCGCCTGGCTGACCGC |
| | CCAACGACCCCCGCCCATTGACGTCAATAATGACGTATGTTCCCATAGTAAC |
| | GCCAATAGGGACTTTCCATTGACGTCAATGGGTGGAGTATTTACGGTAAACT |
| | GCCCACTTGGCAGTACATCAAGTGTATCATATGCCAAGTACGCCCCCTATTG |
| | ACGTCAATGACGGTAAATGGCCCGCCTGGCATTATGCCCAGTACATGACCTT |
| | ATGGGACTTTCCTACTTGGCAGTACATCTACGTATTAGTCATCGCTATTACCA |
| | TGGTGATGCGGTTTTGGCAGTACATCAATGGGCGTGGATAGCGGTTTGACTC |
| | ACGGGGATTTCCAAGTCTCCACCCCATTGACGTCAATGGGAGTTTGTTTTGG |
| | CACCAAAATCAACGGGACTTTCCAAAATGTCGTAACAACTCCGCCCCATTGAC |
| | GCAAATGGGCGGTAGGCGTGTACGGTGGGAGGTCTATATAAGCAGAGCTGG |
| | TTTAGTGAACCGTCAGATCCTGCAGAAGTTGGTCGTGAGGCACTGGGCAGGT |
| | AAGTATCAAGGTTACAAGACAGGTTTAAGGAGACCAATAGAAACTGGGCTTG |
| | TCGAGACAGAGAAGACTCTTGCGTTTCTGATAGGCACCTATTGGTCTTACTGA |
| | CATCCACTTTGCCTTTCTCTCCACAGGTGTCCAGGCGGCCGCNNNGGATCCA |
| | ATCAACCTCTGGATTACAAAATTTGTGAAAGATTGACTGGTATTCTTAACTATG |
| | TTGCTCCTTTTACGCTATGTGGATACGCTGCTTTAATGCCTTTGTATCATGCTA |
| | TTGCTTCCCGTATGGCTTTCATTTTCTCCTCCTTGTATAAATCCTGGTTGCTGT |
| | CTCTTTATGAGGAGTTGTGGCCCGTTGTCAGGCAACGTGGCGTGGTGTGCAC |
| | TGTGTTTGCTGACGCAACCCCCACTGGTTGGGGCATTGCCACCACCTGTCAG |
| | CTCCTTTCCGGGACTTTCGCTTTCCCCCTCCCTATTGCCACGGCGGAACTCA |
| | TCGCCGCCTGCCTTGCCCGCTGCTGGACAGGGGCTCGGCTGTTGGGCACTG |
| | ACAATTCCGTGGTGTTGTCGGGGAAATCATCGTCCTTTCCTTGGCTGCTCGC |
| | CTGTGTTGCCACCTGGATTCTGCGCGGGACGTCCTTCTGCTACGTCCCTTCG |
| | GCCCTCAATCCAGCGGACCTTCCTTCCCGCGGCCTGCTGCCGGCTCTGCGG |
| | CCTCTTCCGCGTCTTCGAGATCTGCCTCGACTGTGCCTTCTAGTTGCCAGCC |
| | ATCTGTTGTTTGCCCCTCCCCCGTGCCTTCCTTGACCCTGGAAGGTGCCACT |
| | CCCACTGTCCTTTCCTAATAAAATGAGGAAATTGCATCGCATTGTCTGAGTAG |
| | GTGTCATTCTATTCTGGGGGGTGGGGTGGGGCAGGACAGCAAGGGGGAGG |
| | ATTGGGAAGACAATAGCAGGCATGCTGGGGACTCGAGTTAAGGGCGAATTC |
| | CCGATAAGGATCTTCCTAGAGCATGGCTACGTAGATAAGTAGCATGGCGGGT |
| | TAATCATTAACTACAAGGAACCCCTAGTGATGGAGTTGGCCACTCCCTCTCTG |
| | CGCGCTCGCTCGCTCACTGAGGCCGGGCGACCAAAGGTCGCCCGACGCCC |
| | GGGCTTTGCCCGGGCGGCCTCAGTGAGCGAGCGAGCGCGCAGCCTTAATTA |
| | ACCTAATTCACTGGCCGTCGTTTTACAACGTCGTGACTGGGAAAACCCTGGC |
| | GTTACCCAACTTAATCGCCTTGCAGCACATCCCCCTTTCGCCAGCTGGCGTA |
| | ATAGCGAAGAGGCCCGCACCGATCGCCCTTCCCAACAGTTGCGCAGCCTGA |
| | ATGGCGAATGGGACGCGCCCTGTAGCGGCGCATTAAGCGCGGCGGGTGTG |
| | GTGGTTACGCGCAGCGTGACCGCTACACTTGCCAGCGCCCTAGCGCCCGCT |
| | CCTTTCGCTTTCTTCCCTTCCTTTCTCGCCACGTTCGCCGGCTTTCCCCGTCA |
| | AGCTCTAAATCGGGGGCTCCCTTTAGGGTTCCGATTTAGTGCTTTACGGCAC |
| | CTCGACCCCAAAAAACTTGATTAGGGTGATGGTTCACGTAGTGGGCCATCGC |
| | CCTGATAGACGGTTTTTCGCCCTTTGACGTTGGAGTCCACGTTCTTTAATAGT |
| | GGACTCTTGTTCCAAACTGGAACAACACTCAACCCTATCTCGGTCTATTCTTT |
| | TGATTTATAAGGGATTTTGCCGATTTCGGCCTATTGGTTAAAAAATGAGCTGA |
| | TTTAACAAAAATTTAACGCGAATTTTAACAAAATATTAACGTTTATAATTTCAGG |
| | TGGCATCTTTCGGGGAAATGTGCGCGGAACCCCTATTTGTTTATTTTTCTAAA |
| | TACATTCAAATATGTATCCGCTCATGAGACAATAACCCTGATAAATGCTTCAAT |
| | AATATTGAAAAAGGAAGAGTATGAGTATTCAACATTTCCGTGTCGCCCTTATT |
| | CCCTTTTTTGCGGCATTTTGCCTTCCTGTTTTTGCTCACCCAGAAACGCTGGT |
| | GAAAGTAAAAGATGCTGAAGATCAGTTGGGTGCACGAGTGGGTTACATCGAA |
| | CTGGATCTCAATAGTGGTAAGATCCTTGAGAGTTTTCGCCCCGAAGAACGTTT |
| | TCCAATGATGAGCACTTTTAAAGTTCTGCTATGTGGCGCGGTATTATCCCGTA |
| | TTGACGCCGGGCAAGAGCAACTCGGTCGCCGCATACACTATTCTCAGAATGA |
| | CTTGGTTGAGTACTCACCAGTCACAGAAAAGCATCTTACGGATGGCATGACA |
| | GTAAGAGAATTATGCAGTGCTGCCATAACCATGAGTGATAACACTGCGGCCA |
| | ACTTACTTCTGACAACGATCGGAGGACCGAAGGAGCTAACCGCTTTTTTGCA |
| | CAACATGGGGGATCATGTAACTCGCCTTGATCGTTGGGAACCGGAGCTGAAT |
| | GAAGCCATACCAAACGACGAGCGTGACACCACGATGCCTGTAGTAATGGTAA |
| | CAACGTTGCGCAAACTATTAACTGGCGAACTACTTACTCTAGCTTCCCGGCAA |
| | CAATTAATAGACTGGATGGAGGCGGATAAAGTTGCAGGACCACTTCTGCGCT |
| | CGGCCCTTCCGGCTGGCTGGTTTATTGCTGATAAATCTGGAGCCGGTGAGC |
| | GTGGGTCTCGCGGTATCATTGCAGCACTGGGGCCAGATGGTAAGCCCTCCC |
| | GTATCGTAGTTATCTACACGACGGGGAGTCAGGCAACTATGGATGAACGAAA |
| | TAGACAGATCGCTGAGATAGGTGCCTCACTGATTAAGCATTGGTAACTGTCA |
| | GACCAAGTTTACTCATATATACTTTAGATTGATTTAAAACTTCATTTTTAATTTA |
| | AAAGGATCTAGGTGAAGATCCTTTTTGATAATCTCATGACCAAAATCCCTTAA |
| | CGTGAGTTTTCGTTCCACTGAGCGTCAGACCCCGTAGAAAAGATCAAAGGAT |
| | CTTCTTGAGATCCTTTTTTTTCTGCGCGTAATCTGCTGCTTGCAAACAAAAAAAC |
| | CACCGCTACCAGCGGTGGTTTGTTTGCCGGATCAAGAGCTACCAACTCTTTT |
| | TCCGAAGGTAACTGGCTTCAGCAGAGCGCAGATACCAAATACTGTCCTTCTA |
| | GTGTAGCCGTAGTTAGGCCACCACTTCAAGAACTCTGTAGCACCGCCTACAT |
| | ACCTCGCTCTGCTAATCCTGTTACCAGTGGCTGCTGCCAGTGGCGATAAGTC |
| | GTGTCTTACCGGGTTGGACTCAAGACGATAGTTACCGGATAAGGCGCAGCG |
| | GTCGGGCTGAACGGGGGGTTCGTGCACACAGCCCAGCTTGGAGCGAACGA |

-continued

```
CCTACACCGAACTGAGATACCTACAGCGTGAGCTATGAGAAAGCGCCACGCT
TCCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTATA
GTCCTGTCGGGTTTCGCCACCTCTGACTTGAGCGTCGATTTTTGTGATGCTC
GTCAGGGGGGCGGAGCCTATGGAAAAACGCCAGCAACGCGGCCTTTTTACG
GTTCCTGGCCTTTTGCTGCGGTTTTGCTCACATGTTCTTTCCTGCGTTATCCC
CTGATTCTGTGGATAACCGTATTACCGCCTTTGAGTGAGCTGATACCGCTCG
CCGCAGCCGAACGACCGAGCGCAGCGAGTCAGTGAGCGAGGAAGCGGAAG
AGCGCCCAATACGCAAACCGCCTCTCCCCGCGCGTTGGCCGATTCATTAATG
CAGCTGGCACGACAGGTTTCCCGACTGGAAAGCGGGCAGTGAGCGCAACGC
AATTAATGTGAGTTAGCTCACTCATTAGGCACCCCAGGCTTTACACTTTATGC
TTCCGGCTCGTATGTTGTGTGGAATTGTGAGCGGATAACAATTTCACACAGG
AAACAGCTATGACCATGATTACGCCAGATTTAATTAAGG (SEQ ID NO: 20)
```

Sheep Model of Myocardial Infarction and Gene Delivery with Anc80

All work was approved by the IACUC at the Mount Sinai School of Medicine. Male sheep were subjected to left surgical thoracotomy to expose the heart. To induce severe myocardial infarction, two select arteries of the coronary artery tree off the main circumflex artery were ligated closed with 7.0 prolene suture to occlude blood flow. The lateral to posterolateral wall region was visibly demarcated with hypoxia indication below the ligations. Confirmation of ST segment elevation confirmed infarct for each procedure. For gene therapy, 1.5 mL of Anc80.AC gene was prepared in two 1 cc syringes with a 26 gauge needle. A total of 15 injections each containing 100 µL was performed directly inside the discolored, infarcted myocardium in the upper basal and middle slices where the majority of myocardium at risk presented. The lower portion apical area was not injected. The animal was closed, recovered and sent for MRI evaluation at 4 weeks and 3 months post infarction.

Total RNA was isolated using the RNeasy mini kit (QIAGEN) and reverse transcribed using Superscript III reverse transcriptase (Invitrogen), according to the manufacturer's instructions. Real-time qPCR analyses were performed on a Mastercycler realplex 4 Sequence Detector (Eppendoff) using SYBR Green (Quantitect™ SYBR Green PCR Kit, QIAGEN). Data were normalized to 18srRNA expression where appropriate (endogenous controls). Fold changes of gene expression were determined by the ddCT method. PCR primer sequences are summarized in Table 2.

(Invitrogen, Carlsbad, CA, USA) under reducing conditions and MES running buffer (Invitrogen), and transferred onto a nitrocellulose membrane (Bio-Rad) using a semidry transfer apparatus and Nupage-MOPS transfer buffer (Invitrogen). The membrane was block with TBS/Tween containing 5% dry milk and incubated with specific primary antibodies over night at 4° C. washed with TBS/Tween and incubated with rabbit or goat antibodies conjugated to horseradish peroxidase for 1 hour at room temperature. Detection was performed by an enhanced chemiluminecence (ECL) detection system (Pierce, Rockford, IL). For molecular weight determination prestained protein standards (Amersham, Buckinghamshire, UK) were used.

Immunohistochemistry

The mouse hearts were harvested and perfused using perfusion buffer (2 g/l butanedione, monoxime and 7.4 g/l KCl in PBSx1) and 4% paraformaldehyde (PFA). Hearts were fixed in 4% PFA/PBS overnight on shaker and then washed with PBS for 1 hr and incubated in 30% sucrose/ PBS at 40 C overnight. Before freezing, hearts were mounted in OCT for 30 min and frozen at −80° C. Transverse heart sections of 10 µM were made by cryostat. Cryosections were washed in PBST and blocked for 1 h with 5% donkey serum in PBST. Sections were incubated over night at 4° C. using primary antibodies for Troponin I, Sphk1, S1p2. Secondary antibodies were used for fluorescent labeling (Jackson ImmunoResearch Laboratories). TUNEL staining was performed according to manufacturer's recommendations (In-Situ Cell Death Detection Kit,

TABLE 2

| Gene | Forward | SEQ ID NO. | Reverse | SEQ ID NO. |
|---|---|---|---|---|
| AC | ACAGGATTCAAACCAGGACTGT | 21 | TGGGCATCTTTCCTTCCGAA | 22 |
| AC | TGACAGGATTCAAACCAGGACT | 23 | CTGGGCATCTTTCCTTCCGA | 24 |
| Sphk1 | ATACTCACCGAACGGAAGAACC | 25 | CCATTAGCCCATTCACCACCTC | 26 |
| Sphk1 | ACTGATACTCACCGAACGGAA | 27 | CATTAGCCCATTCACCACCTC | 28 |
| S1PR2 | CACAGCCAACAGTCTCCAAA | 29 | TCTGAGTATAAGCCGCCCA | 30 |
| S1PR2 | ATAGACCGAGCACAGCCAA | 31 | GAACCTTCTCAGGATTGAGGT | 32 |
| 18s rRNA* | TAACGAACGAGACTCTGGCAT | 33 | CGGACATCTAAGGGCATCACA G | 34 |

*Genetic Vaccines and Therapy 2004, 2:5

Western Blot

Upon thawing, hearts lysates' were subjected to separation by SDS-PAGE using 12% precast Nupage Bis/Tris gels Fluorescein, Cat #11684795910, Roche). Stained sections were imaged using a Zeiss Slide Scanner Axio Scan or Zeiss mic. Quantification of TUNEL in cardiac sections was performed using ImageJ software. For cell immunocyto-chemistry, Hek293 and isolated CMs were fixed on cover-slips with 4% PFA for 10 min at room temperature. Follow-ing permeabilization with 0.1% TRITON® X100 in PBS for 10 min at room temperature, cells were blocked with 5% Donkey serum+0.1% TRITON® X100 in PBS for 30 min-utes. Coverslips were incubated with primary antibodies in humidity chamber for 1 hour at room temperature followed by incubation with corresponding secondary antibodies con-jugated to Alexa Fluor 488, Alexa Fluor 647 and Alexa Fluor 555, and Hoechst 33342 staining for nuclei visualization (all from Invitrogene). The fluorescent images were taken on a Zeiss fluorescent microscope at 20× magnification.

Cardiac MRI Background

Cardiac magnetic resonance imaging (CMRI) is gold standard for the evaluation of volume, dimensions, structure and complete diagnostic profile of myocardium. The advan-tages of MRI over all other imaging modalities including echocardiography and CT are well established and are: (1) non user dependency (2) high reproducibility (3) averaging of several hundred heartbeats (4) high spatial/temporal reso-lution programmed without inter or intra subject variability (5) non-invasive means to analyze viability, inflammation and metabolic profile without using probes or invasive lines. CMRI is acquired over the course of a 1 hour exam inside a standard magnet with clinical protocol. In these experi-ments: 45 kg male sheep were intubated, maintained on anesthesia and placed into a Siemens Skyra 3T magnet. Standard long axis, short axis, and t2 weighted maps along with contrast to determine infarct size were performed on baseline and follow up studies. 15 mL of gadolinium con-trast was used to assess myocardial infarction size and tissue characteristics per standard clinical protocols. An experi-enced, blinded user analyzed the DICOM files offline.

Injection of Anc80.AC into rat hearts shows higher AC activity in the heart tissue when compared to untreated hearts (control 34 nM vs Anc80.AC 12 nM).

Results in sheep demonstrate that treatment with Anc80.AC immediately after myocardial infarction (MI) leads to complete rescue of the MI injected area with very robust contractility. The heart function results are excellent, greater than 60%, which is in the range for baseline animals. Only very minor scarring was detected in the non-injected area. No effect on heart rate and no indication of myocarditis was observed.

These findings suggest that by modulating ceramide lev-els from stressed cells and elevating S1P, the cell death pathway is inhibited and cell survival is initiated, in vivo.

In vivo applications include administration of recombi-nant AC variant 1 (rACv1). In one embodiment, 0.005 µg/µl of rACV1 is admixed into a gel or cream to be administered to the skin in order to prevent cell death or reverse senes-cence/aging of epithelial skin cells.

In another embodiment, 0.005 µg/µl of rACV1 is admixed into a suitable eye drop preparation in order to prevent cell death or reverse senescence/aging of cone cells post stress-related reaction.

More than 90 percent of hearing loss occurs when either hair cells or auditory nerve cells are destroyed. The present method provides an opportunity to prevent or reduce the loss of hair cells, thereby reducing the likelihood of hearing loss.

It is to be understood that, while the methods and com-positions of matter have been described herein in conjunc-tion with a number of different aspects, the forgoing descrip-tion of the various aspects is intended to illustrate and not limit the scope of the methods and compositions of matter. Other aspects, advantages, and modifications are within the scope of the following claims.

REFERENCES

Perez G I, Tao X J, Tilly J L. Fragmentation and death (a.k.a. apoptosis) of ovulated oocytes. Mol Hum Reprod. 1999; 5(5):414-20.

Eliyahu E, Park J H, Shtraizent N, He X, Schuchman E H. Acid ceramidase is a novel factor required for early embryo survival. FASEB J. 2007; 21(7):1403-9.

Eliyahu E, Shtraizent N, Martinuzzi K, Barritt J, He X, Wei H, Chaubal S, Copperman A B, Schuchman E H. Acid ceramidase improves the quality of oocytes and embryos and the outcome of in vitro fertilization. FASEB J. 2010; 24(4):1229-38.

Katalin Karikó, Hiromi Muramatsu, Frank A Welsh, János Ludwig, Hiroki Kato, Shizuo Akira, Drew Weissman. Incorporation of Pseudouridine Into mRNA Yields Supe-rior Nonimmunogenic Vector With Increased Transla-tional Capacity and Biological Stability. Mol Ther. 2008; 16(11): 1833-1840.

Yang H, Wang H, Shivalila C S, Cheng A W, Shi L, Jaenisch R. One-step generation of mice carrying reporter and conditional alleles by CRISPR/Cas-mediated genome engineering. Cell. 2013; 154(6):1370-9.

Wu Y, Liang D, Wang Y, Bai M, Tang W, Bao S, Yan Z, Li D, Li J. Correction of a genetic disease in mouse via use of CRISPR-Cas9. Cell Stem Cell. 2013; 13(6):659-62.

Ruzo A, Brivanlou A H. At Last: Gene Editing in Human Embryos to Understand Human Development. Cell Stem Cell. 2017; 21(5):564-565.

Frumkin T, Peleg S, Gold V, Reches A, Asaf S, Azem F, Ben-Yosef D, Malcov M. Complex chromosomal rear-rangement—a lesson learned from PGS. J Assist Reprod Genet. 2017; 34(8):1095-1100.

Zinn et al. In *Silico Reconstruction of the Viral Evolutionary Lineage Yields a Potent Gene Therapy Vector, Cell Reports* 12. 1056-1068 (2015)

---

We claim:

1. A method to restore heart function in a subject following ischemia, reperfusion injury or myocardial infarction (MI), the method comprising:

directly administering a therapeutically effective amount of an Anc80 viral vector comprising a nucleotide sequence encoding an acid ceramidase protein to cardiac cells of the subject in vivo, wherein the nucleotide sequence encoding the acid ceramidase is operatively linked to an expression control sequence.

2. The method of claim 1, wherein the nucleotide sequence encoding the acid ceramidase is as set out in one of SEQ ID NO: 1, SEQ ID NO: 6 and SEQ ID NO: 7.

3. The method of claim 1, wherein the nucleotide sequence encoding the acid ceramidase is as set out in SEQ ID NO: 1.

4. The method of claim 1, wherein the nucleotide sequence encoding the acid ceramidase is as set out in SEQ ID NO: 6.

5. The method of claim 1, wherein the nucleotide sequence encoding the acid ceramidase is as set out in SEQ ID NO: 7.

* * * * *